United States Patent
Bramucci et al.

(10) Patent No.: US 6,548,292 B1
(45) Date of Patent: Apr. 15, 2003

(54) BACTERIAL PLASMID HAVING GENES ENCODING ENZYMES FOR THE DEGRADATION OF AROMATIC COMPOUNDS

(75) Inventors: Michael G. Bramucci, Folsom, PA (US); Mario W. Chen, Chadds Ford, PA (US); Vasantha Nagarajan, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/716,865

(22) Filed: Nov. 20, 2000

Related U.S. Application Data

(60) Provisional application No. 60/167,062, filed on Nov. 23, 1999.

(51) Int. Cl.$^7$ .............................. C12N 9/00; C12N 1/00; C12N 15/00; C12N 1/20; C07H 21/04
(52) U.S. Cl. ............... 435/252.3; 435/243; 435/252.34; 435/262; 435/262.1; 435/183; 435/320.1; 536/23.2; 536/23.4; 536/23.7
(58) Field of Search ............................... 536/23.2, 23.4, 536/23.7; 435/243, 252.3, 252.34, 262, 183, 320.1, 262.5

(56) References Cited

PUBLICATIONS

Actis et al., Front, Biosci. 4:D43–62 (1999).
del Solar et al., Microbiol. Mol. Biol. Rev. 62:434–464 (1998).
Fu et al., (Mol. Gene. Genet 250:699–704 (1996).
Jen–Fen Fu et al., Plasmid 38:141–147 (1997).
Assinder and Williams, Adv. Microb. Physiol. 31:2–69 (1990).
Williams and Sayers, Biodegradation 5:195–217 (1994).
Ngai et al., Meth Enzymol. 188:122–126 (1990).
Kataeva and Golovleva, Meth. Enzymol. 188:115–121 (1990).
Mars et al. Genbank Accession No.: AAD05249, GI: 4160463, Mar. 18, 1999.
Mars et al. Genbank Accession No.: AAD05250, GI: 4160464, Mar. 18, 1999.
Bosch et al. Genbank Accession No.: AAD02149, GI: 4104767, Mar. 23, 2000.
Bosch et al. Genbank Accession No.: AAD02151, GI: 4104769, Mar. 23, 2000.
Winans S.C. Genbank Accession No.: AAB97287, GI: 1163228, Jan. 21, 1998.
Woodgate R. Genbank Accession No.: AAB58712, GI: 2145308, Jun. 2, 1997.
Hofer et al., Gene 144 (1), 9–16 (1994).
Paterson et al., J. Bacteriol 181:2572–2583, 1999.
Pullinger and Lax Mol. Microbiol 6:1631–1543 (1992).
Fu et al., Plasmid 34: 75–84 (1995).

*Primary Examiner*—Rebecca E. Prouty
*Assistant Examiner*—Manjunath N. Rao

(57) ABSTRACT

A bacterial plasmid has been isolated from Pseudomonas CT14 comprising genes encoding enzymes implicated in aromatic ring cleavage. Additionally, the novel genes encoding proteins involved in mercury tolerance and plasmid stability and replication have been identified. The strain from which the plasmid was isolated is useful in a variety of methods including methods for the degradation of aromatic compounds, particularly catechols.

4 Claims, 3 Drawing Sheets

- Filtered air passes through the inlet
- Vacuum siphons DNA up the tube
- Sample is atomized, shearing DNA
- Sample is recycled
- 30-60 sec is usually enough to shear
- Remove sample

Figure 2. Map of ORFs for pCT14

SEQUENCE LISTING

<160> NUMBER OF SEQ ID NOS: 26

<210> SEQ ID NO 1
<211> LENGTH: 360
<212> TYPE: DNA
<213> ORGANISM: Pseudomonas CT14

<400> SEQUENCE: 1

```
atgttcttcg acaccgccc caaggtcagc gtgcatgtca tgcaaaccgg tgaaacctt      60 ccctgcgcca cggatgagag tctgctgcaa ggcatgctgc gcctgggccg caagggcatc    120
ccggtgggct gcgtcaacgg cggctgtggg gtctgcaagg tccatgttat tgagggtcaa    180
tgccggcctc tgggtcctgt tagccgcgcg catgtcagtg ccgcagagga agcacgcggc    240
ttcaccctgg cctgccgtgt ggcgccggtc accccggttc aactggaggt ggtgggcaag    300
tttgaaaagg tttttcaaa agggttcgtt tcatcaacga acgagattat taacaaatga    360
```

<210> SEQ ID NO 2
<211> LENGTH: 119
<212> TYPE: PRT
<213> ORGANISM: Pseudomonas CT14

<400> SEQUENCE: 2

```
Met Phe Phe Asp Thr Arg Pro Lys Val Ser Val His Val Met Gln Thr
  1               5                  10                  15
```

```
Gly Glu Thr Phe Pro Cys Ala Thr Asp Glu Ser Leu Leu Gln Gly Met
             20                  25                  30

Leu Arg Leu Gly Arg Lys Gly Ile Pro Val Gly Cys Val Asn Gly Gly
         35                  40                  45

Cys Gly Val Cys Lys Val His Val Ile Glu Gly Gln Cys Arg Pro Leu
     50                  55                  60

Gly Pro Val Ser Arg Ala His Ser Ala Ala Glu Glu Ala Arg Gly
 65                  70                  75                  80

Phe Thr Leu Ala Cys Arg Val Ala Pro Val Thr Pro Val Gln Leu Glu
                 85                  90                  95

Val Val Gly Lys Phe Glu Lys Val Phe Ser Lys Gly Phe Val Ser Ser
             100                 105                 110

Thr Asn Glu Ile Ile Asn Lys
         115

<210> SEQ ID NO 3
<211> LENGTH: 945
<212> TYPE: DNA
<213> ORGANISM: Pseudomonas CT14

<400> SEQUENCE: 3
atgagtatta tgagagttgg ccacgtcagc atcaacgtga tggacatggc cgcagcagtg      60
aagcactacg aaaacgtgct gggcctaaag acgaccatgc aggacaatgc cgggaacgtg     120
tacctgaaat gttgggacga gtgggataaa tattccctta tcctcacccc atcggacagg     180
gctggaatga accacgtcgc ctacaaggtt accaaagaca gtgatctgga cgccttccaa     240
gctaggattg aagccgctgg caccaagacc accatgatgc ccgagggcac gctgccatcc     300
acggggcgca tgctggtgtt taaattgcca agcacgcacg aaatgcgtct ttacgccatg     360
aaagaaaacg tcggcaccga ggtgggtagc atcaatcccg atccgtggcc agacagcatc     420
aagggtgccg gggcgcactg gttggatcac gtactactga tgtgtgagtt cgatccgggc     480
actggtgtca atagggtggc cgacaacaca cggttcttca ttgatgtgct ggatttttc      540 ctgaccgagc aattgaccgt cggccccgat ggctcattcc agtcggcatc gttcctgtcg     600
tgctcgagca agccgcatga cattgcgttt gttggtgcgc cgactcccgg cctgcaccat     660
atttcgtatt tcctggactc gtggcacgac attctcaagg cgggcgatgt catggccaag     720
aacaaggtac gtattgatgc gtcacctaca cgccatggct tcacgcgcgg cgagacgatc     780
tatttcttcg accctagcgg caaccgcaat gagacctttg caggactggg gtaccaggcg     840
cagcgggacc gcccggtgac gacttggacc gaagatcaag cgggtcgcgc aattttcttc     900
cacaccggcg agatggtgtc gtcgttcaca gatgtgtaca catga                     945

<210> SEQ ID NO 4
<211> LENGTH: 314
<212> TYPE: PRT
<213> ORGANISM: Pseudomonas CT14

<400> SEQUENCE: 4

Met Ser Ile Met Arg Val Gly His Val Ser Ile Asn Val Met Asp Met
 1               5                  10                  15

Ala Ala Ala Val Lys His Tyr Glu Asn Val Leu Gly Leu Lys Thr Thr
             20                  25                  30

Met Gln Asp Asn Ala Gly Asn Val Tyr Leu Lys Cys Trp Asp Glu Trp
         35                  40                  45

Asp Lys Tyr Ser Leu Ile Leu Thr Pro Ser Asp Arg Ala Gly Met Asn
```

```
              50                  55                  60
His Val Ala Tyr Lys Val Thr Lys Asp Ser Asp Leu Asp Ala Phe Gln
 65                  70                  75                  80

Ala Arg Ile Glu Ala Ala Gly Thr Lys Thr Thr Met Met Pro Glu Gly
                 85                  90                  95

Thr Leu Pro Ser Thr Gly Arg Met Leu Val Phe Lys Leu Pro Ser Thr
            100                 105                 110

His Glu Met Arg Leu Tyr Ala Met Lys Glu Asn Val Gly Thr Glu Val
        115                 120                 125

Gly Ser Ile Asn Pro Asp Pro Trp Pro Asp Ser Ile Lys Gly Ala Gly
    130                 135                 140

Ala His Trp Leu Asp His Val Leu Leu Met Cys Glu Phe Asp Pro Gly
145                 150                 155                 160

Thr Gly Val Asn Arg Val Ala Asp Asn Thr Arg Phe Phe Ile Asp Val
                165                 170                 175

Leu Asp Phe Phe Leu Thr Glu Gln Leu Thr Val Gly Pro Asp Gly Ser
            180                 185                 190

Phe Gln Ser Ala Ser Phe Leu Ser Cys Ser Ser Lys Pro His Asp Ile
        195                 200                 205

Ala Phe Val Gly Ala Pro Thr Pro Gly Leu His His Ile Ser Tyr Phe
    210                 215                 220

Leu Asp Ser Trp His Asp Ile Leu Lys Ala Gly Asp Val Met Ala Lys
225                 230                 235                 240

Asn Lys Val Arg Ile Asp Ala Ser Pro Thr Arg His Gly Phe Thr Arg
                245                 250                 255

Gly Glu Thr Ile Tyr Phe Phe Asp Pro Ser Gly Asn Arg Asn Glu Thr
            260                 265                 270

Phe Ala Gly Leu Gly Tyr Gln Ala Gln Arg Asp Arg Pro Val Thr Thr
        275                 280                 285

Trp Thr Glu Asp Gln Ala Gly Arg Ala Ile Phe Phe His Thr Gly Glu
    290                 295                 300

Met Val Ser Ser Phe Thr Asp Val Tyr Thr
305                 310

<210> SEQ ID NO 5
<211> LENGTH: 1461
<212> TYPE: DNA
<213> ORGANISM: Pseudomonas CT14

<400> SEQUENCE: 5
atgaaagaca tcaggaactt catcaacggt gaatacgtca ccaatgtcag cggcaagacc      60
tacgagaagc gcaacccggt tgataacagc ctaatcggca tggtccatga agctggtcag     120
cccgaggtgg atgcggcggt ggccgccgcg cgcgcggcac tgaacgggcc tggggcaag     180 ctctcggtgg tcgaccgctg cgccatgctc gatggtgtgg ttgccgagat caaccgccgg     240
tttgatgatt ttctgcaggc cgaaattgcc gataccggca agcccgcgca cctggcatcg     300
cacatcgaca tcccgcgcgg tgccgccaac ttcaagatat tcaccgacac catcaaaaac     360
gtctcgaccg aatcctttga gatgcgcacc ccgacggta aaacagcgcg cagctacggc      420
gtgcgcaccc cgcgtggcgt cattgccatc atctgcccat ggaatttgcc gctgctgctg     480
atgacctgga atgtggcccg gccatggctg tgcggcaaca ctgtggtcgt caagccatca     540
gaggccactc ccagcaccgc cacgctgttg ggcgaagtca tgaacaaggt cggcgtaccg     600
cccggcgtct acaacgtggt gaacggcttt ggcgtcaact cggcgggctc cttcctgacc     660
```

-continued

```
gcgcaccagg gcgtcaacgg catcaccttc accggtgaaa ccaagactgg caccgccatc    720
atgaaagccg gtgccgacgg catccgcccg gtgtcactcg aattgggcgg caaaaacgcg    780
gccgtggtgt ttgccgactg cgattttgaa aacgctctgg ccaccgtgac ccgctctgcc    840
tttgagaact gcggccaggt ctgtctgggc actgagcgcg tgtatgtgga gcgaccgatt    900
tttgacaaat tcgtcagcgc cctgaaagag cgcgccgcgg ccatcaagcc cggccgtccg    960
tttgatgccg ataccaaaat tggcccgctg gtgagcaaaa tccaccagaa aaaggtgctg   1020
tcttactacc caaagccaa agcagaaggt gccaatattg ttcttggtgg cggcgttccc    1080
aatatgccag atgacctgaa agacggctgc tgggtcgaac ccaccatctg gactggcctg   1140
cccgagagtt cacctattgt tcgtgaagaa atttttggcc catgctgcca tatccagccg   1200
tttgacaccg aagaagaggt gctgaatatg gtcaacgaca gccctacgg cctggccact    1260 tctattcaca cccaggatat cagccgagcc agccgtcttg caacgcaaat cgaggtgggt   1320
ctgtgctgga tcaacagctg gttcctgcgt gatttgcgca cccctttgg cggctccaag   1380 cagtcgggta tcgggcgtga aggtggcctg cattcgctgg agttctacac cgaactgcgc   1440
aacgtgatga tcaagtattg a                                             1461
```

<210> SEQ ID NO 6
<211> LENGTH: 486
<212> TYPE: PRT
<213> ORGANISM: Pseudomonas CT14

<400> SEQUENCE: 6

```
Met Lys Asp Ile Arg Asn Phe Ile Asn Gly Glu Tyr Val Thr Asn Val
  1               5                  10                  15

Ser Gly Lys Thr Tyr Glu Lys Arg Asn Pro Val Asp Asn Ser Leu Ile
             20                  25                  30

Gly Met Val His Glu Ala Gly Gln Pro Glu Val Asp Ala Ala Val Ala
         35                  40                  45

Ala Ala Arg Ala Ala Leu Asn Gly Pro Trp Gly Lys Leu Ser Val Val
     50                  55                  60

Asp Arg Cys Ala Met Leu Asp Gly Val Val Ala Glu Ile Asn Arg Arg
 65                  70                  75                  80

Phe Asp Asp Phe Leu Gln Ala Glu Ile Ala Asp Thr Gly Lys Pro Ala
                 85                  90                  95

His Leu Ala Ser His Ile Asp Ile Pro Arg Gly Ala Ala Asn Phe Lys
            100                 105                 110

Ile Phe Thr Asp Thr Ile Lys Asn Val Ser Thr Glu Ser Phe Glu Met
        115                 120                 125

Arg Thr Pro Asp Gly Lys Thr Ala Arg Ser Tyr Gly Val Arg Thr Pro
    130                 135                 140

Arg Gly Val Ile Ala Ile Ile Cys Pro Trp Asn Leu Pro Leu Leu Leu
145                 150                 155                 160

Met Thr Trp Lys Cys Gly Pro Ala Met Ala Cys Gly Asn Thr Val Val
                165                 170                 175

Val Lys Pro Ser Glu Ala Thr Pro Ser Thr Ala Thr Leu Leu Gly Glu
            180                 185                 190

Val Met Asn Lys Val Gly Val Pro Pro Gly Val Tyr Asn Val Val Asn
        195                 200                 205

Gly Phe Gly Val Asn Ser Ala Gly Ser Phe Leu Thr Ala His Gln Gly
    210                 215                 220
```

-continued

```
Val Asn Gly Ile Thr Phe Thr Gly Glu Thr Lys Thr Gly Thr Ala Ile
225                 230                 235                 240

Met Lys Ala Gly Ala Asp Gly Ile Arg Pro Val Ser Leu Glu Leu Gly
            245                 250                 255

Gly Lys Asn Ala Ala Val Val Phe Ala Asp Cys Asp Phe Glu Asn Ala
            260                 265                 270

Leu Ala Thr Val Thr Arg Ser Ala Phe Glu Asn Cys Gly Gln Val Cys
            275                 280                 285

Leu Gly Thr Glu Arg Val Tyr Val Glu Arg Pro Ile Phe Asp Lys Phe
            290                 295                 300

Val Ser Ala Leu Lys Glu Arg Ala Ala Ile Lys Pro Gly Arg Pro
305                 310                 315                 320

Phe Asp Ala Asp Thr Lys Ile Gly Pro Leu Val Ser Lys Ile His Gln
                325                 330                 335

Lys Lys Val Leu Ser Tyr Tyr Ala Lys Ala Lys Ala Glu Gly Ala Asn
            340                 345                 350

Ile Val Leu Gly Gly Gly Val Pro Asn Met Pro Asp Asp Leu Lys Asp
            355                 360                 365

Gly Cys Trp Val Glu Pro Thr Ile Trp Thr Gly Leu Pro Glu Ser Ser
370                 375                 380

Pro Ile Val Arg Glu Glu Ile Phe Gly Pro Cys Cys His Ile Gln Pro
385                 390                 395                 400

Phe Asp Thr Glu Glu Glu Val Leu Asn Met Val Asn Asp Ser Pro Tyr
                405                 410                 415

Gly Leu Ala Thr Ser Ile His Thr Gln Asp Ile Ser Arg Ala Ser Arg
            420                 425                 430

Leu Ala Thr Gln Ile Glu Val Gly Leu Cys Trp Ile Asn Ser Trp Phe
            435                 440                 445

Leu Arg Asp Leu Arg Thr Pro Phe Gly Gly Ser Lys Gln Ser Gly Ile
            450                 455                 460

Gly Arg Glu Gly Gly Leu His Ser Leu Glu Phe Tyr Thr Glu Leu Arg
465                 470                 475                 480

Asn Val Met Ile Lys Tyr
                485

<210> SEQ ID NO 7
<211> LENGTH: 612
<212> TYPE: DNA
<213> ORGANISM: Pseudomonas CT14

<400> SEQUENCE: 7
atgaagcttt attactctcc tggcgcttgc tcgctgtcac cccacattgc cctgcgcgaa      60
gccggtctgg actttgactt ggtcaaggtc gatctcaaaa ccaagaaaac cgatgctggt     120
gacgattact ttgcagtgaa ccccagcggc tatgtgccct gtttgcagat cgacgatggt     180
cgcatgctca ccgaaggccc cgccatcgtg caatacatcg ctgaccaagc ggctggcaaa     240
aaacttgcgc cgctcaacgg cacgtttgag cgctatcaac tacagcagtg gcttaacttt     300
atttccaccg agattcataa aagttttttcc ccgctgttca accccgatgc cagcgctgac     360
tccaaggcta cggcgcgcaa gactttggat gcccgcttgg cgacagcagc agcacaactt     420
tccaagacac cctatttgct tggagagagc tactctgtcg ccgacatcta cctgttttgtt     480 accttgggct gggctggcta tgtgggtgtg gacttggcgc catggcctgc gttgcaacac     540
ttttcggccc gggtggcctc ccgcgatgcc gttcaggcca ccttgcgcgc agaaggtttg     600
```
attcaggcct ga    612

<210> SEQ ID NO 8
<211> LENGTH: 203
<212> TYPE: PRT
<213> ORGANISM: Pseudomonas CT14

<400> SEQUENCE: 8

```
Met Lys Leu Tyr Tyr Ser Pro Gly Ala Cys Ser Leu Ser Pro His Ile
 1               5                  10                  15

Ala Leu Arg Glu Ala Gly Leu Asp Phe Asp Leu Val Lys Val Asp Leu
            20                  25                  30

Lys Thr Lys Lys Thr Asp Ala Gly Asp Asp Tyr Phe Ala Val Asn Pro
        35                  40                  45

Ser Gly Tyr Val Pro Cys Leu Gln Ile Asp Asp Gly Arg Met Leu Thr
    50                  55                  60

Glu Gly Pro Ala Ile Val Gln Tyr Ile Ala Asp Gln Ala Gly Lys
 65                  70                  75                  80

Lys Leu Ala Pro Leu Asn Gly Thr Phe Glu Arg Tyr Gln Leu Gln Gln
                85                  90                  95

Trp Leu Asn Phe Ile Ser Thr Glu Ile His Lys Ser Phe Ser Pro Leu
            100                 105                 110

Phe Asn Pro Asp Ala Ser Ala Asp Ser Lys Ala Thr Ala Arg Lys Thr
        115                 120                 125

Leu Asp Ala Arg Leu Ala Thr Ala Ala Gln Leu Ser Lys Thr Pro
    130                 135                 140

Tyr Leu Leu Gly Glu Ser Tyr Ser Val Ala Asp Ile Tyr Leu Phe Val
145                 150                 155                 160

Thr Leu Gly Trp Ala Gly Tyr Val Gly Val Asp Leu Ala Pro Trp Pro
                165                 170                 175

Ala Leu Gln His Phe Ser Ala Arg Val Ala Ser Arg Asp Ala Val Gln
            180                 185                 190

Ala Thr Leu Arg Ala Glu Gly Leu Ile Gln Ala
        195                 200
```

<210> SEQ ID NO 9
<211> LENGTH: 795
<212> TYPE: DNA
<213> ORGANISM: Pseudomonas CT14

<400> SEQUENCE: 9

```
atgacccaga cgcccaacca actcgccgaa gcgatctggg ccgcccgcca ggccggtcgg    60
acactggacg ccgcagccac catcggcacg cccgacctcg ccaccgccta cgccatccag   120
cgcgcgctgc tcggcctgcg cctggccgcc ggcgagcgcg tggtcgggtg aagctgggt   180
tacacgtcgg aagtgatgcg ccgccagatg ggcatagccc ggcccaacat cgggccgctg   240
accgaccgga tgctgctgaa ctcgggcgac gcggtgcacg agcgcctggt gcagccgcgg   300
gtcgaacccg agatcgggct cgccctccaa accgccctcg acgcgcggca cgcgcccgtc   360
gaccgccaca ccgtggtcgc cgccgtggag ggcgcctacg cctgcctcga agtcgtgcac   420
tccacctgga caggctaccg cttcaacctc gaacagaaca ccgccgacaa ctcgtccgcc   480
ggccaggtcg tcgtcgggcc acgcctgccg gtgaccgacc tgatggcggc gggcaccgtg   540
gcggtgcgcc tgcacgacgg cagccaccac acgctgggac agggcgtggg cgccgatgcc   600
gacggccacc ccctggacgc ggtggcgcgg ctggcgcggg agctggccgc gtttggtcag   660
```

```
cggctggagg cgggtgatct ggtgatcacg ggtgggctga caaaggcttg tgagctggag    720 gtgggggga  ggttgacggg agtgttttcg tttggggacg cttggtcggt agatgtgact    780
gtgcggcgtc tgtga                                                     795
```

<210> SEQ ID NO 10
<211> LENGTH: 264
<212> TYPE: PRT
<213> ORGANISM: Pseudomonas CT14

<400> SEQUENCE: 10

```
Met Thr Gln Thr Pro Asn Gln Leu Ala Glu Ala Ile Trp Ala Ala Arg
 1               5                  10                  15

Gln Ala Gly Arg Thr Leu Asp Ala Ala Thr Ile Gly Thr Pro Asp
            20                  25                  30

Leu Ala Thr Ala Tyr Ala Ile Gln Arg Ala Leu Leu Gly Leu Arg Leu
        35                  40                  45

Ala Ala Gly Glu Arg Val Val Gly Trp Lys Leu Gly Tyr Thr Ser Glu
    50                  55                  60

Val Met Arg Arg Gln Met Gly Ile Ala Arg Pro Asn Ile Gly Pro Leu
65                  70                  75                  80

Thr Asp Arg Met Leu Leu Asn Ser Gly Asp Ala Val His Glu Arg Leu
                85                  90                  95

Val Gln Pro Arg Val Glu Pro Glu Ile Gly Leu Arg Leu Gln Thr Ala
            100                 105                 110

Leu Asp Ala Arg His Ala Pro Val Asp Arg His Thr Val Val Ala Ala
        115                 120                 125

Val Glu Gly Ala Tyr Ala Cys Leu Glu Val Val His Ser Thr Trp Thr
    130                 135                 140

Gly Tyr Arg Phe Asn Leu Glu Gln Asn Thr Ala Asp Asn Ser Ser Ala
145                 150                 155                 160

Gly Gln Val Val Val Gly Pro Arg Leu Pro Val Thr Asp Leu Met Ala
                165                 170                 175

Ala Gly Thr Val Ala Val Arg Leu His Asp Gly Ser His His Thr Leu
            180                 185                 190

Gly Gln Gly Val Gly Ala Asp Ala Asp Gly His Pro Leu Asp Ala Val
        195                 200                 205

Ala Arg Leu Ala Arg Glu Leu Ala Ala Phe Gly Gln Arg Leu Glu Ala
    210                 215                 220

Gly Asp Leu Val Ile Thr Gly Gly Leu Thr Lys Ala Cys Glu Leu Glu
225                 230                 235                 240

Val Gly Gly Arg Leu Thr Gly Val Phe Ser Phe Gly Asp Ala Trp Ser
                245                 250                 255

Val Asp Val Thr Val Arg Arg Leu
            260
```

<210> SEQ ID NO 11
<211> LENGTH: 2955
<212> TYPE: DNA
<213> ORGANISM: Pseudomonas CT14

<400> SEQUENCE: 11

```
atgctcgata tcacgaccat ttctcggcaa tcactgggca aagtcgtgtc gtactacgcg    60
gatggtgcgg atgactacta cgcaaaagac ggcggcgcca tgcaatggca aggtgccggc   120
gccgaggcat tgggcctgtc cggggaagta gagcaggccc gattccgcga gctattggat   180
```

-continued

| | |
|---|---|
| ggccgaatta gcgacagcac gaagctcatg cgcactgtca aagaggctga tggcaaagtg | 240 |
| gtcagcaagg aaaggcttgg gtatgacctc acctttcag cgcccaaagg tgtgtcgctc | 300 |
| caggccttgg tccacggtga cgccagcatt atcgaagccc acgataaggc ggtggcagca | 360 |
| gccattcgcg aggctgaacg gttgtcccag gcccgaataa cggtcaacaa gaagaccggt | 420 |
| accgagaaca ccaacaactt ggtggtggcc aagttccgac acgaaacctc acgcgccctg | 480 |
| gaccccgacc tgcatacca tgcgttcgtg ctgaacatga cccagcgtag cgacggcgaa | 540 |
| tggcgggcac tgaaaaatga cggtgtgttc aattcgtcca tgttcctggg caacgtctac | 600 |
| aaggcggaac tggcccgcga gctggaaaag gccggcttcc agttgcgcta tgagcgcaac | 660 |
| ggtacattcg acctgcgca tttctccgac gagcagatcc gcgaattcag ttcgcgcagc | 720 |
| cagcagatcg aggcagcgct agcggcgaaa ggcctggacc gcagcacagc gtcgtatgct | 780 |
| gaaaagaacc aggccgcgct ggccacccgc gacaaaaagc agggtggaat cgaccgcgaa | 840 |
| gaattgcgcc aggtttggct tgaacggtcg agggctttgg gtatcgacta ccacagccgc | 900 |
| gagtgggccg gcgtcggcgc cgatgcgcaa ggcggcaggg agcgaaacag cgccgccact | 960 |
| ccgcagatcg agaagcccct ggagtaccgt gccgaccagg tgatcgaatt cgcgatcaag | 1020 |
| agtctgaccg agcgccaggc ggttatcggt cagaaggagc tgatggatac cgcgctgcgc | 1080 |
| cacgggtacg gcgccctcac catcgacgac gtgcgcgccg gcatcgagcg gcgtgccgca | 1140 |
| tctggccacc tgatccgcga ggaaccgctt tactcttcac aaaaccctgc cgatggaaag | 1200 |
| aaggggaagg ccgccgagaa ggcccgcgaa gaggcgccac agctcagccg caaggaatgg | 1260 |
| gtggcaaccc ttgtccgcgc cggcaaatcg cgctcagagg ccgccaggct cgttgatgag | 1320 |
| ggcatccgca ccgacggct gcgccaggt gaaaaccgtt ttaccacgca catcgcgcag | 1380 |
| aagcgcgaac gcgaggtgct gcaaatcgag cgaatggggc gcggtacggt tgagccacgg | 1440 |
| atctctaaag aagccgccga agccttcctt gccgatcggg gcttgaaggc ggaacagcag | 1500 |
| gcctcggtga tgcggatcgc ccgcacacaa aaccagttca tcggcgtcca gggctttgcc | 1560 |
| ggcgtcggca aaagctacat gactgtagcg gccaaggatc tgctggaggc gaacggatac | 1620 |
| cgtgtcacca gcctggcgcc ctatggtagc caggtgaagg cgctccaggc cgagggtctg | 1680 |
| gaggctcgta ctctgcaatc gttcctcaag gcccgcgata gaagatcga cagcaacacc | 1740 |
| gtcgtgttca tcgacgaggc cggcgtaata cctgcgcggc agatgcacga agccatgaaa | 1800 |
| accatcgagc tgccggcgc ccgcgtggtc ttcctgggcg acgtagcaca aaccaaagcc | 1860 |
| atcgaggccg gcaaacccttt cgagcagctg atgaaagccg gcatggaaac gtcccggctg | 1920 |
| accgacattc agcggcagaa ggacccgcaa ttgctgaggg cggtgaagct ggccgccgag | 1980 |
| ggtaaagcca agcaatcgct gccactggtg aacgagatac gcgagatcaa ggaagacggg | 2040 |
| gcacgctacc aggcgattgt cgacgcctac gccaaaatga cgaaggccga gcgtgaccag | 2100 |
| gctctaatta tcaccggtac caacgccagt cggatccaaa tcaacgaagg cgtgcgggag | 2160 |
| gcgctgggac tgaaagggca gggcgcggag tatccattgc tcaaccgtct ggatacgacc | 2220 |
| caagccgagc gccggcacag taaatactac ggcaagggca gcattgtcgt ccccgaggtg | 2280 |
| gactataaga acgggctgca acgtggcgta cagtacgtgg tactcgacac cggccccggc | 2340 |
| aacaaactca ccgtgcgcgg gccagaaggc gagacgctgc aattcactcc agcccgttgt | 2400 |
| acaaagcttt cggtctacag cgtcgagaga acagagcttg tcgctgggga tcaggtgaaa | 2460 |
| atcacccgaa cgacgctga aaaggacttg gccaacggcg accgatttgt ggtgaaggag | 2520 |
| atccacagcg accgcgtggt gctcgaagga gacaaaggcc gccaggtcga gctggacaca | 2580 |

-continued

```
gcatcggcta tgttcgtcgg cctggcctat gcttcgaccg ttcacagcgc ccagggtctc    2640
acctgcgaca aggtgctcat caaccttgaa acccaatcgc gcaccaccgc caaggacgtg    2700
tactacgtgg ctatcagccg cgcccgtcat gcagcggaaa tcttcaccga taaccggcag    2760
aagctggggg atgcgatcag ccgcttgaac gccaaggccg cgccctgga tatcaagcag    2820 ctccagcggc atgcgctcga gcgcaaaggg cacgaccagg ctggcaaaca gaaggacgcc    2880
gtgcagaagc aacagcaagg ccagcaattg ccggccaaac agcccaaaga aaagggcagg    2940
gcattcggtc tgtaa                                                    2955
```

<210> SEQ ID NO 12
<211> LENGTH: 984
<212> TYPE: PRT
<213> ORGANISM: Pseudomonas CT14

<400> SEQUENCE: 12

```
Met Leu Asp Ile Thr Thr Ile Ser Arg Gln Ser Leu Gly Lys Val Val
 1               5                  10                  15

Ser Tyr Tyr Ala Asp Gly Ala Asp Tyr Tyr Ala Lys Asp Gly Gly
            20                  25                  30

Ala Met Gln Trp Gln Gly Ala Gly Ala Glu Ala Leu Gly Leu Ser Gly
        35                  40                  45

Glu Val Glu Gln Ala Arg Phe Arg Glu Leu Leu Asp Gly Arg Ile Ser
    50                  55                  60

Asp Ser Thr Lys Leu Met Arg Thr Val Lys Glu Ala Asp Gly Lys Val
65                  70                  75                  80

Val Ser Lys Glu Arg Leu Gly Tyr Asp Leu Thr Phe Ser Ala Pro Lys
                85                  90                  95

Gly Val Ser Leu Gln Ala Leu Val His Gly Asp Ala Ser Ile Ile Glu
            100                 105                 110

Ala His Asp Lys Ala Val Ala Ala Ile Arg Glu Ala Glu Arg Leu
        115                 120                 125

Ser Gln Ala Arg Ile Thr Val Asn Lys Lys Thr Gly Thr Glu Asn Thr
    130                 135                 140

Asn Asn Leu Val Val Ala Lys Phe Arg His Glu Thr Ser Arg Ala Leu
145                 150                 155                 160

Asp Pro Asp Leu His Thr His Ala Phe Val Leu Asn Met Thr Gln Arg
                165                 170                 175

Ser Asp Gly Glu Trp Arg Ala Leu Lys Asn Asp Gly Val Phe Asn Ser
            180                 185                 190

Ser Met Phe Leu Gly Asn Val Tyr Lys Ala Glu Leu Ala Arg Glu Leu
        195                 200                 205

Glu Lys Ala Gly Phe Gln Leu Arg Tyr Glu Arg Asn Gly Thr Phe Asp
    210                 215                 220

Leu Ala His Phe Ser Asp Glu Gln Ile Arg Glu Phe Ser Ser Arg Ser
225                 230                 235                 240

Gln Gln Ile Glu Ala Ala Leu Ala Ala Lys Gly Leu Asp Arg Ser Thr
                245                 250                 255

Ala Ser Tyr Ala Glu Lys Asn Gln Ala Ala Leu Ala Thr Arg Asp Lys
            260                 265                 270

Lys Gln Gly Gly Ile Asp Arg Glu Glu Leu Arg Gln Val Trp Leu Glu
        275                 280                 285

Arg Ser Arg Ala Leu Gly Ile Asp Tyr His Ser Arg Glu Trp Ala Gly
    290                 295                 300
```

-continued

```
Val Gly Ala Asp Ala Gln Gly Gly Arg Glu Arg Asn Ser Ala Ala Thr
305                 310                 315                 320

Pro Gln Ile Glu Lys Pro Leu Glu Tyr Arg Ala Asp Gln Val Ile Glu
            325                 330                 335

Phe Ala Ile Lys Ser Leu Thr Glu Arg Gln Ala Val Ile Gly Gln Lys
            340                 345                 350

Glu Leu Met Asp Thr Ala Leu Arg His Gly Tyr Gly Ala Leu Thr Ile
            355                 360                 365

Asp Asp Val Arg Ala Gly Ile Glu Arg Arg Ala Ser Gly His Leu
            370                 375                 380

Ile Arg Glu Glu Pro Leu Tyr Ser Ser Gln Asn Pro Ala Asp Gly Lys
385                 390                 395                 400

Lys Gly Lys Ala Ala Glu Lys Ala Arg Glu Glu Ala Pro Gln Leu Ser
                405                 410                 415

Arg Lys Glu Trp Val Ala Thr Leu Val Arg Ala Gly Lys Ser Arg Ser
            420                 425                 430

Glu Ala Ala Arg Leu Val Asp Glu Gly Ile Arg Thr Gly Arg Leu Arg
            435                 440                 445

Gln Gly Glu Asn Arg Phe Thr Thr His Ile Ala Gln Lys Arg Glu Arg
450                 455                 460

Glu Val Leu Gln Ile Glu Arg Met Gly Arg Gly Thr Val Glu Pro Arg
465                 470                 475                 480

Ile Ser Lys Glu Ala Ala Glu Ala Phe Leu Ala Asp Arg Gly Leu Lys
                485                 490                 495

Ala Glu Gln Gln Ala Ser Val Met Arg Ile Ala Arg Thr Gln Asn Gln
            500                 505                 510

Phe Ile Gly Val Gln Gly Phe Ala Gly Val Gly Lys Ser Tyr Met Thr
            515                 520                 525

Val Ala Ala Lys Asp Leu Leu Glu Ala Asn Gly Tyr Arg Val Thr Ser
            530                 535                 540

Leu Ala Pro Tyr Gly Ser Gln Val Lys Ala Leu Gln Ala Glu Gly Leu
545                 550                 555                 560

Glu Ala Arg Thr Leu Gln Ser Phe Leu Lys Ala Arg Asp Lys Lys Ile
            565                 570                 575

Asp Ser Asn Thr Val Val Phe Ile Asp Glu Ala Gly Val Ile Pro Ala
            580                 585                 590

Arg Gln Met His Glu Ala Met Lys Thr Ile Glu Ala Ala Gly Ala Arg
            595                 600                 605

Val Val Phe Leu Gly Asp Val Ala Gln Thr Lys Ala Ile Glu Ala Gly
            610                 615                 620

Lys Pro Phe Glu Gln Leu Met Lys Ala Gly Met Glu Thr Ser Arg Leu
625                 630                 635                 640

Thr Asp Ile Gln Arg Gln Lys Asp Pro Gln Leu Leu Glu Ala Val Lys
            645                 650                 655

Leu Ala Ala Glu Gly Lys Ala Lys Gln Ser Leu Pro Leu Val Asn Glu
            660                 665                 670

Ile Arg Glu Ile Lys Glu Asp Gly Ala Arg Tyr Gln Ala Ile Val Asp
            675                 680                 685

Ala Tyr Ala Lys Met Thr Lys Ala Glu Arg Asp Gln Ala Leu Ile Ile
            690                 695                 700

Thr Gly Thr Asn Ala Ser Arg Ile Gln Ile Asn Glu Gly Val Arg Glu
705                 710                 715                 720
```

```
Ala Leu Gly Leu Lys Gly Gln Gly Ala Glu Tyr Pro Leu Leu Asn Arg
                725                 730                 735

Leu Asp Thr Thr Gln Ala Glu Arg Arg His Ser Lys Tyr Tyr Gly Lys
            740                 745                 750

Gly Ser Ile Val Val Pro Glu Val Asp Tyr Lys Asn Gly Leu Gln Arg
                755                 760                 765

Gly Val Gln Tyr Val Val Leu Asp Thr Gly Pro Gly Asn Lys Leu Thr
    770                 775                 780

Val Arg Gly Pro Glu Gly Glu Thr Leu Gln Phe Thr Pro Ala Arg Cys
785                 790                 795                 800

Thr Lys Leu Ser Val Tyr Ser Val Glu Arg Thr Glu Leu Val Ala Gly
                805                 810                 815

Asp Gln Val Lys Ile Thr Arg Asn Asp Ala Lys Asp Leu Ala Asn
                820                 825                 830

Gly Asp Arg Phe Val Val Lys Glu Ile His Ser Asp Arg Val Val Leu
            835                 840                 845

Glu Gly Asp Lys Gly Arg Gln Val Glu Leu Asp Thr Ala Ser Ala Met
850                 855                 860

Phe Val Gly Leu Ala Tyr Ala Ser Thr Val His Ser Ala Gln Gly Leu
865                 870                 875                 880

Thr Cys Asp Lys Val Leu Ile Asn Leu Glu Thr Gln Ser Arg Thr Thr
                885                 890                 895

Ala Lys Asp Val Tyr Tyr Val Ala Ile Ser Arg Ala Arg His Ala Ala
                900                 905                 910

Glu Ile Phe Thr Asp Asn Arg Gln Lys Leu Gly Asp Ala Ile Ser Arg
            915                 920                 925

Leu Asn Ala Lys Ala Gly Ala Leu Asp Ile Lys Gln Leu Gln Arg His
    930                 935                 940

Ala Leu Glu Arg Lys Gly His Asp Gln Ala Gly Lys Gln Lys Asp Ala
945                 950                 955                 960

Val Gln Lys Gln Gln Gln Gly Gln Gln Leu Pro Ala Lys Gln Pro Lys
                965                 970                 975

Glu Lys Gly Arg Ala Phe Gly Leu
            980
```

<210> SEQ ID NO 13
<211> LENGTH: 1539
<212> TYPE: DNA
<213> ORGANISM: Pseudomonas CT14

<400> SEQUENCE: 13

```
atgaacgagc gccaacgatc tcaaatctgc ctcgccgtca tggtgctggt gccactgttc      60
gcgtggttct ttaccgccaa gctgatgtat ggaattgaaa agcaaggcgc ccgagacagg     120
gtgttctacc tggcgaaaaa cacgttcacc ttgtggccgc ttgcggttgc tttagttggt     180
gggctgatac tcgcgattgc gttgtgcgtg cttatcgtga agttgagcaa gaccactttt     240
gccggcgctc actttgataa gtatttccgt ggtagccaac ttgtctccca gcgtgagctt     300
aaacgactga caaaggagaa agaggaacaa ataactattg ccggggtgcc tgttcctatt     360
gctgccgagg cgacacactt tcagttggc ggggccacgg tacgggtaa gagtacgatt      420 ttccgcgaaa tgatgtatgg ctgcatgcag cggaaagatc gcatggtaat ccttgatccc     480
gatggagagt tccctatctac cttctaccgc aagggcgata aaatcctgaa tccatatgat     540
gccaggacgg aaggttggaa cttctataac gaaatccgta gtcactacga tttcgagcgc     600
```

-continued

```
tacgcaaaat ccattattca agtttcagac agtaacgact cggaagaatg gaaccagtat      660
ggccgtctgc tgttcgcaga ggtggccaag aagctgtata acaccacgcg caaccctggc      720
atgcgggaag tattccgatg gactaacgag tgcgactcgg aaactcttca ggcttttgta      780
aaaggcacaa gagccgtatc tttgtttact gaaaacgagc gcgctacagg cagcgtccgg      840
tttgtcctca gtaataaact acctgcgcat tttgatatgc caccaggcaa tttttcgctg      900
cgccagtggt gcgaagatcc taacggcggc aacttgttta tcacttggga cgagaacatg      960
cgcgaagcgc tgcgcccatt gattagttgc tgggtggata ccattttcac cagcattctt     1020
gggatgaagt ccaatcccaa cgccggatc tggaccttcc ttgacgagct ggaatcgctg      1080
caacgactgc ccaccctggg cgacatgttg actcggggcc ggaagaaggg cggttgcgtg     1140
gtatctggct accagtccta cacccagctc gaatccgtgt atggcgagaa actggctgaa     1200
acgatgctgg ccaaccaccg gacaatggtt gccctggccg ttggccgcat gggtacggca     1260
accgccgaac gcatgtccaa agccttgagc gagcatgaag tactgcgcac caaggaaggc     1320
cgcagctcgc gctggggtga ctggggcact cgcagcgaga acgaggatgt gaaacccgag     1380
cgcatcgtta tgtcgtcgga gatcatggct ttgaacaacc tcgaaggctt cctgtcgttc     1440
cccggaagca tcccgattgc gcgtgtgacc atcgacccga tcaacttcac ccgcacgaac     1500
ccggtaccgg gcatcgtccc aaaccttgag atcatctaa                             1539
```

<210> SEQ ID NO 14
<211> LENGTH: 512
<212> TYPE: PRT
<213> ORGANISM: Pseudomonas CT14

<400> SEQUENCE: 14

```
Met Asn Glu Arg Gln Arg Ser Gln Ile Cys Leu Ala Val Met Val Leu
  1               5                  10                  15

Val Pro Leu Phe Ala Trp Phe Thr Ala Lys Leu Met Tyr Gly Ile
                 20                  25                  30

Glu Lys Gln Gly Ala Arg Asp Arg Val Phe Tyr Leu Ala Lys Asn Thr
             35                  40                  45

Phe Thr Leu Trp Pro Leu Ala Val Ala Leu Val Gly Gly Leu Ile Leu
         50                  55                  60

Ala Ile Ala Leu Cys Val Leu Ile Val Lys Leu Ser Lys Thr Thr Phe
 65                  70                  75                  80

Ala Gly Ala His Phe Asp Lys Tyr Phe Arg Gly Ser Gln Leu Val Ser
                 85                  90                  95

Gln Arg Glu Leu Lys Arg Leu Thr Lys Glu Lys Glu Glu Gln Ile Thr
            100                 105                 110

Ile Ala Gly Val Pro Val Pro Ile Ala Ala Glu Ala Thr His Phe Ser
        115                 120                 125

Val Gly Gly Ala Thr Gly Thr Gly Lys Ser Thr Ile Phe Arg Glu Met
    130                 135                 140

Met Tyr Gly Cys Met Gln Arg Lys Asp Arg Met Val Ile Leu Asp Pro
145                 150                 155                 160

Asp Gly Glu Phe Leu Ser Thr Phe Tyr Arg Lys Gly Asp Lys Ile Leu
                165                 170                 175

Asn Pro Tyr Asp Ala Arg Thr Glu Gly Trp Asn Phe Tyr Asn Glu Ile
            180                 185                 190

Arg Ser His Tyr Asp Phe Glu Arg Tyr Ala Lys Ser Ile Ile Gln Val
        195                 200                 205
```

```
Ser Asp Ser Asn Asp Ser Glu Glu Trp Asn Gln Tyr Gly Arg Leu Leu
    210                 215                 220
Phe Ala Glu Val Ala Lys Lys Leu Tyr Asn Thr Thr Arg Asn Pro Gly
225                 230                 235                 240
Met Arg Glu Val Phe Arg Trp Thr Asn Glu Cys Asp Ser Glu Thr Leu
                245                 250                 255
Gln Ala Phe Val Lys Gly Thr Arg Ala Val Ser Leu Phe Thr Glu Asn
            260                 265                 270
Glu Arg Ala Thr Gly Ser Val Arg Phe Val Leu Ser Asn Lys Leu Pro
        275                 280                 285
Ala His Phe Asp Met Pro Pro Gly Asn Phe Ser Leu Arg Gln Trp Cys
    290                 295                 300
Glu Asp Pro Asn Gly Gly Asn Leu Phe Ile Thr Trp Asp Glu Asn Met
305                 310                 315                 320
Arg Glu Ala Leu Arg Pro Leu Ile Ser Cys Trp Val Asp Thr Ile Phe
                325                 330                 335
Thr Ser Ile Leu Gly Met Lys Ser Asn Pro Lys Arg Arg Ile Trp Thr
            340                 345                 350
Phe Leu Asp Glu Leu Glu Ser Leu Gln Arg Leu Pro Thr Leu Gly Asp
        355                 360                 365
Met Leu Thr Arg Gly Arg Lys Lys Gly Gly Cys Val Val Ser Gly Tyr
    370                 375                 380
Gln Ser Tyr Thr Gln Leu Glu Ser Val Tyr Gly Glu Lys Leu Ala Glu
385                 390                 395                 400
Thr Met Leu Ala Asn His Arg Thr Met Val Ala Leu Ala Val Gly Arg
                405                 410                 415
Met Gly Thr Ala Thr Ala Glu Arg Met Ser Lys Ala Leu Ser Glu His
            420                 425                 430
Glu Val Leu Arg Thr Lys Glu Gly Arg Ser Ser Arg Trp Gly Asp Trp
        435                 440                 445
Gly Thr Arg Ser Glu Asn Glu Asp Val Lys Pro Glu Arg Ile Val Met
    450                 455                 460
Ser Ser Glu Ile Met Ala Leu Asn Asn Leu Glu Gly Phe Leu Ser Phe
465                 470                 475                 480
Pro Gly Ser Ile Pro Ile Ala Arg Val Thr Ile Asp Pro Ile Asn Phe
                485                 490                 495
Thr Arg Thr Asn Pro Val Pro Gly Ile Val Pro Asn Leu Glu Ile Ile
            500                 505                 510
```

<210> SEQ ID NO 15
<211> LENGTH: 390
<212> TYPE: DNA
<213> ORGANISM: Pseudomonas CT14

<400> SEQUENCE: 15

```
gtgcaagccc tgattttgct gtattttgtg tctgacacac gtcagacaag gagaccatcc      60
gtgcccacag tgagctttcg atgcaccgaa acacagaaaa tcgagctgga agagcggtcc     120
cagggcgaca tttcggagta tgtacgccgg cagcttttcc ggcagatgga gcaggaggac     180
acgctagaaa tgatcctcca gcgcctcgat caacggcctg gcgtgacgg ccagccgacc      240
gctggaatcg accgccagtc gatggccatc ttgatcgagc tgctattgct tctgcgcacc     300
gcgtccaaac cggatgctaa gagggaagcc caggccgagg tcgagcgcct gggcttcgac     360
gtatgggatt catcaaagag ggatagctga                                      390
```

-continued

```
<210> SEQ ID NO 16
<211> LENGTH: 129
<212> TYPE: PRT
<213> ORGANISM: Pseudomonas CT14

<400> SEQUENCE: 16
```

Val Gln Ala Leu Ile Leu Leu Tyr Phe Val Ser Asp Thr Arg Gln Thr
1               5                   10                  15

Arg Arg Pro Ser Val Pro Thr Val Ser Phe Arg Cys Thr Glu Thr Gln
            20                  25                  30

Lys Ile Glu Leu Glu Glu Arg Ser Gln Gly Asp Ile Ser Glu Tyr Val
        35                  40                  45

Arg Arg Gln Leu Phe Arg Gln Met Glu Gln Glu Asp Thr Leu Glu Met
    50                  55                  60

Ile Leu Gln Arg Leu Asp Gln Arg Pro Gly Gly Asp Gly Gln Pro Thr
65                  70                  75                  80

Ala Gly Ile Asp Arg Gln Ser Met Ala Ile Leu Ile Glu Leu Leu Leu
                85                  90                  95

Leu Leu Arg Thr Ala Ser Lys Pro Asp Ala Lys Arg Glu Ala Gln Ala
            100                 105                 110

Glu Val Glu Arg Leu Gly Phe Asp Val Trp Asp Ser Ser Lys Arg Asp
        115                 120                 125

Ser

```
<210> SEQ ID NO 17
<211> LENGTH: 438
<212> TYPE: DNA
<213> ORGANISM: Pseudomonas CT14

<400> SEQUENCE: 17
atgagcaaaa agacgtacat gctcgatacg aacatctgtt cgttcatcat gcgcgagcgc    60
cccgacgcgg tgctggccaa gctggaacag gcagtcacta atcagcaccg gattgtcgtt   120
tcggccatca cctactccga aatgcgtttc ggggccgcca accccaaggc atcgcccaag   180
gttgcagcga tggtcgatgc cttcatccag cgcctggacg ccatcctgtc ctgggacgcc   240
gccgccgtag atcaaacaac gcagatccgc accgccctcg cccgcctggg tacgcccatt   300
ggcaacaacg atgcagcgat agccggccat gccctggccg ctgggtgtgt tctggtcacg   360
aacaacactc gcgaatttgc tcgcgttcct ggcctagtcc ttgaggactg acccaaccc   420 gccattacca agagttga                                                  438

<210> SEQ ID NO 18
<211> LENGTH: 145
<212> TYPE: PRT
<213> ORGANISM: Pseudomonas CT14

<400> SEQUENCE: 18
```

Met Ser Lys Lys Thr Tyr Met Leu Asp Thr Asn Ile Cys Ser Phe Ile
1               5                   10                  15

Met Arg Glu Arg Pro Asp Ala Val Leu Ala Lys Leu Glu Gln Ala Val
            20                  25                  30

Thr Asn Gln His Arg Ile Val Val Ser Ala Ile Thr Tyr Ser Glu Met
        35                  40                  45

Arg Phe Gly Ala Ala Asn Pro Lys Ala Ser Pro Lys Val Ala Ala Met
    50                  55                  60

Val Asp Ala Phe Ile Gln Arg Leu Asp Ala Ile Leu Ser Trp Asp Ala

```
                65                  70                  75                  80
Ala Ala Val Asp Gln Thr Thr Gln Ile Arg Thr Ala Leu Ala Arg Leu
                        85                  90                  95

Gly Thr Pro Ile Gly Asn Asn Asp Ala Ala Ile Ala Gly His Ala Leu
            100                 105                 110

Ala Ala Gly Cys Val Leu Val Thr Asn Asn Thr Arg Glu Phe Ala Arg
        115                 120                 125

Val Pro Gly Leu Val Leu Glu Asp Trp Thr Gln Pro Ala Ile Thr Lys
    130                 135                 140

Ser
145

<210> SEQ ID NO 19
<211> LENGTH: 237
<212> TYPE: DNA
<213> ORGANISM: Pseudomonas CT14

<400> SEQUENCE: 19
atgcgtaccg tttccatttt catgaacagc cgaaaccagg cgatccgcat ccctcgggat      60
atggagtacc agggcgtttc cgagctggag attatccgcg acggcgaaac gctgatcctg     120
cgccctgtgc gccctcctg  ggcatcgttg cgcgacgtgg cggccgcaga tcctgacttt     180
ctgaccgagc gaaaggatgt gatcgaggaa gaccgtttcc tgggtgactt cacatga       237

<210> SEQ ID NO 20
<211> LENGTH: 78
<212> TYPE: PRT
<213> ORGANISM: Pseudomonas CT14

<400> SEQUENCE: 20

Met Arg Thr Val Ser Ile Phe Met Asn Ser Arg Asn Gln Ala Ile Arg
1               5                   10                  15

Ile Pro Arg Asp Met Glu Tyr Gln Gly Val Ser Glu Leu Glu Ile Ile
            20                  25                  30

Arg Asp Gly Glu Thr Leu Ile Leu Arg Pro Val Arg Pro Ser Trp Ala
        35                  40                  45

Ser Leu Arg Asp Val Ala Ala Ala Asp Pro Asp Phe Leu Thr Glu Arg
    50                  55                  60

Lys Asp Val Ile Glu Glu Asp Arg Phe Leu Gly Asp Phe Thr
65                  70                  75

<210> SEQ ID NO 21
<211> LENGTH: 1137
<212> TYPE: DNA
<213> ORGANISM: Pseudomonas CT14

<400> SEQUENCE: 21
atgtcgtcca atgagttgtt tgatatcgac cccgacgtgg ccaccacccc accaccgaaa      60
cgtcggccag cggccagagg ccccttggtc gggcaggacg caatcaacat cgacaagtgg     120
cgcaagcgca tcgaggctga agcacgacca ggcgaaacct accagcaggc ggcggagcgg     180
ctgaaacgcg aagaggccaa gcaaccgaag gacaaggcac agggcgcgga gcggtgaag     240 acctcagcgg gacgcaaaca gtagtggtg ctcgaaacgc agctcgattt ctggatcgcg     300
accggcctgc cggcgatccc caaagatgag cgacctacga tggagcaccc gatctacgcc     360
gtggaagacg gagataccag gcagatcacc tacgagcaca cgggaacaa  atcgagatc     420 actcccagcg ttgccggtcg ggcgaccag catgacaaag atatcgtgct gttttgcgta    480
```

-continued

```
tcgaagctag tggctgcgat caacgccggc atagccgtat caccgactat cgagacgacc    540
gctcacgaac ttttgagctt cacgcgcagc agtaccagcg agcgcggcta tgagctgctt    600
agcaaggctt tcgacagact caccggtact cgcatgcggg ccacctttga gtcgacgaaa    660
gaccgtgacg gcagccgtcg ctgggttggc ctgctcgatg acgtggagat catcactagg    720
ggcgccaaga accgcatgtg cgccattcgg ataaaggtat ccgacaccac gtttaacgcc    780
gcgaaggcca tggatgtgtt gaccattccg ggcgactatt ttgggctgcg cagcgccatt    840
gccaaacgca tctatgagct ttgccggaaa cattgcggcg atcagggcca atggaagatt    900
ggcctggctc tgctgcaaaa gaaggtcgga agcgcccagg ccgaaaagaa gtttcgcgct    960
aaggtcaagg agctggccga ggccggcagc ttgctcgact acttcatgac ctacctgccc   1020
gacgaagacg ccgtgttgtt cttcaacaag tccgacgccg gcaaagcggc cttgctcaaa   1080
gccacgcgca acgtatcaa gaagccacgc aaggccaagg ccgctcccgc tgcatga      1137
```

<210> SEQ ID NO 22
<211> LENGTH: 378
<212> TYPE: PRT
<213> ORGANISM: Pseudomonas CT14

<400> SEQUENCE: 22

```
Met Ser Ser Asn Glu Leu Phe Asp Ile Asp Pro Asp Val Ala Thr Thr
 1               5                  10                  15

Pro Pro Pro Lys Arg Arg Pro Ala Ala Arg Gly Pro Leu Val Gly Gln
            20                  25                  30

Asp Ala Ile Asn Ile Asp Lys Trp Arg Lys Arg Ile Glu Ala Glu Ala
        35                  40                  45

Arg Pro Gly Glu Thr Tyr Gln Gln Ala Ala Glu Arg Leu Lys Arg Glu
    50                  55                  60

Glu Ala Lys Gln Pro Lys Asp Lys Ala Pro Gly Arg Glu Ala Val Lys
65                  70                  75                  80

Thr Ser Ala Gly Arg Lys Gln Val Val Leu Glu Thr Gln Leu Asp
                85                  90                  95

Phe Trp Ile Ala Thr Gly Leu Pro Ala Ile Pro Lys Asp Glu Arg Pro
            100                 105                 110

Thr Met Glu His Pro Ile Tyr Ala Val Glu Asp Gly Asp Thr Arg Gln
        115                 120                 125

Ile Thr Tyr Glu His Asn Gly Asn Lys Ile Glu Ile Thr Pro Ser Val
    130                 135                 140

Ala Gly Arg Ala Thr Gln His Asp Lys Asp Ile Val Leu Phe Cys Val
145                 150                 155                 160

Ser Lys Leu Val Ala Ala Ile Asn Ala Gly Ile Ala Val Ser Pro Thr
                165                 170                 175

Ile Glu Thr Thr Ala His Glu Leu Leu Ser Phe Thr Arg Ser Ser Thr
            180                 185                 190

Ser Glu Arg Gly Tyr Glu Leu Leu Ser Lys Ala Phe Asp Arg Leu Thr
        195                 200                 205

Gly Thr Arg Met Arg Ala Thr Phe Glu Ser Thr Lys Asp Arg Asp Gly
    210                 215                 220

Ser Arg Arg Trp Val Gly Leu Leu Asp Asp Val Glu Ile Ile Thr Arg
225                 230                 235                 240

Gly Ala Lys Asn Arg Met Cys Ala Ile Arg Ile Lys Val Ser Asp Thr
                245                 250                 255
```

-continued

```
Thr Phe Asn Ala Ala Lys Ala Met Asp Val Leu Thr Ile Pro Gly Asp
        260                 265                 270

Tyr Phe Gly Leu Arg Ser Ala Ile Ala Lys Arg Ile Tyr Glu Leu Cys
    275                 280                 285

Arg Lys His Cys Gly Asp Gln Gly Gln Trp Lys Ile Gly Leu Ala Leu
    290                 295                 300

Leu Gln Lys Lys Val Gly Ser Ala Gln Ala Glu Lys Lys Phe Arg Ala
305                 310                 315                 320

Lys Val Lys Glu Leu Ala Glu Ala Gly Ser Leu Leu Asp Tyr Phe Met
                325                 330                 335

Thr Tyr Leu Pro Asp Glu Asp Ala Val Leu Phe Phe Asn Lys Ser Asp
            340                 345                 350

Ala Gly Lys Ala Ala Leu Leu Lys Ala Thr Arg Asn Gly Ile Lys Lys
        355                 360                 365

Pro Arg Lys Ala Lys Ala Ala Pro Ala Ala
        370                 375
```

<210> SEQ ID NO 23
<211> LENGTH: 55216
<212> TYPE: DNA
<213> ORGANISM: Pseudomonas CT14

<400> SEQUENCE: 23

```
ggtggcaaca gcggttaaca gtggttttgc caacgttgcg aggcagcgct gcgcctgtca    60
ccgccaaaaa cgggtcatac cgaaaaatct cgggcaactg gctttgagaa atcaacccag   120
cagtcccctg tgtgcatgcc tgagacgccc aaacgtgtg ctatacttgt gctcatgcgg   180
ttggatttcc tatccccga cctgccatag ccggcgcgcc ccaccctcaa cctttccagg   240
cggagccccc ccatgaccca gacgcccaac caactcgccg aagcgatctg gccgcccgc    300
caggccggtc ggacactgga gaggcagcgc tgcgcctgtc accgcaaaaa cgggtcata    360
ccgaaaaatc tcgggcaact ggctttgaga atcaaccca gcagtcccct gtgtgcatgc    420
ctgagacgcc caaacgtgt gctatacttg tgctcatgcg gttggatttc ctatccccga    480
agttcctctc cgcagccgac accaaccagc agcgcagtcc tctgttcaag cgggtttgaa    540
ggggaataag catgttcttc gacacccgcc caaggtcag cgtgcatgtc atgcaaaccg    600
gtgaaacctt tccctgcgcc acggatgaga gtctgctgca aggcatgctg cgcctgggcc    660
gcaagggcat cccggtgggc tgcgtcaacg gcggctgtgg ggtctgcaag gtccatgtta    720
ttgagggtca atgccggcct ctgggtcctg ttagccgcgc gcatgtcagt gccgcagagg    780
aagcacgcgg cttcaccctg gcctgccgtg tggcgccggt caccccggtt caactggagg    840
tggtgggcaa gttgaaaag gtttttcaa aagggttcgt tcatcaacg aacgagatta    900
ttaacaaatg aaggagacac acatgagtat tatgagagtt ggccacgtca gcatcaacgt    960
gatggacatg gccgcagcag tgaagcacta cgaaaacgtg ctgggcctaa agacgaccat   1020
gcaggacaat gccgggaacg tgtacctgaa atgttgggac gagtgggata aatattccct   1080
tatcctcacc ccatcggaca gggctggaat gaaccacgtc gcctacaagg ttaccaaaga   1140
cagtgatctg gacgccttcc aagctaggat tgaagccgct ggcaccaaga ccaccatgat   1200
gcccgagggc acgctgccat ccacgggggg catgctggtg tttaaattgc aagcacgca    1260
cgaaatgcgt ctttacgcca tgaaagaaaa cgtcggcacc gaggtgggta gcatcaatcc   1320
cgatccgtgg ccagacagca tcaagggtgc cggggcgcac tggttggatc acgtactact   1380
gatgtgtgag ttcgatccgg gcactggtgt caataggtg ccgacaaca cacggttctt    1440
```

-continued

```
cattgatgtg ctggattttt tcctgaccga gcaattgacc gtcggcccga atggctcatt    1500
ccagtcggca tcgttcctgt cgtgctcgag caagccgcat gacattgcgt ttgttggtgc    1560
gccgactccc ggcctgcacc atatttcgta tttcctggac tcgtggcacg acattctcaa    1620
ggcgggcgat gtcatggcca agaacaaggt acgtattgat gcgtcaccta cacgccatgg    1680
cttcacgcgc ggcgagacga tctatttctt cgacccctagc ggcaaccgca atgagaccct    1740
tgcaggactg gggtaccagg cgcagcggga ccgcccggtg acgacttgga ccgaagatca    1800
agcgggtcgc gcaattttct tccacaccgg cgagatggtg tcgtcgttca cagatgtgta    1860
cacatgatcg attgaatgac cagtgggggc cccaagtctt gattcatcag cttggggcgc    1920
ctttgtttca ataacggata accacccatg caaaagacca tttcaccgca agcccctaac    1980
ccgactcaca gcatcgtcgt gcccacgatt gactggcacg ccgcacacga ggcagttggt    2040
gccgcagtga aggcggcgca ggccatgggt atacgcgtca acgtcgcggt ggtggacgct    2100
tccggtgtgc tggccgcctt cttgcgcatg ccgggggccc cgctgcattc ggtcgaaatc    2160
gccatagaca aagcctacac cgcagtcagt tttggcttgg cgaccagcca gtggcatggg    2220
gcgttgcagc agcattcagt ggccgtgcgc gagggcattg tgttgcggcc ccgcttttgtg    2280 gcgtttggcg gcggcttgcc ggtgctggaa acggacagc gcattggcgg catcggcgtc    2340
tccggtggct ccgagcaaga ggatgaaagc tgcgcccgcg ccgggttggc cgccctgggt    2400
ttggcggcat aacagcaccc gcccaattac cacttcaaga gagagaaaaa tgaaagacat    2460
caggaacttc atcaacggtg aatacgtcac caatgtcagc ggcaagacct acgagaagcg    2520
caacccggtt gataacagcc taatcggcat ggtccatgaa gctggtcagc cgaggtgga    2580 tgcggcggtg gccgccgcgc gcgcggcact gaacgggccc tggggcaagc tctcggtggt    2640
cgaccgctgc gccatgctcg atggtgtggt tgccagatc aaccgccggt ttgatgattt    2700
tctgcaggcc gaaattgccg ataccggcaa gcccgcgcac ctggcatcgc acatcgacat    2760
cccgcgcggt gccgccaact tcaagatatt caccgacacc atcaaaaacg tctcgaccga    2820
atcctttgag atgcgcaccc ccgacggtaa acagcgcgc agctacggcg tgcgcacccc    2880
gcgtggcgtc attgccatca tctgcccatg gaatttgccg ctgctgctga tgacctggaa    2940
atgtggcccg gccatggcct gcggcaacac tgtggtcgtc aagccatcag aggccactcc    3000
cagcaccgcc acgctgttgg gcgaagtcat gaacaaggtc ggcgtaccgc ccggcgtcta    3060
caacgtggtg aacggctttg gcgtcaactc ggcgggctcc ttcctgaccg cgcaccaggg    3120
cgtcaacggc atcaccttca ccggtgaaac caagactggc accgccatca tgaaagccgg    3180
tgccgacggc atccgcccgg tgtcactcga attgggcggc aaaaacgcgg ccgtggtgtt    3240
tgccgactgc gattttgaaa acgctctggc caccgtgacc cgctctgcct tgagaactg    3300 cggccaggtc tgtctgggca ctgagcgcgt gtatgtggag cgaccgattt ttgacaaatt    3360
cgtcagcgcc ctgaaagagc gcgccgcggc catcaagccc ggccgtccgt ttgatgccga    3420
taccaaaatt ggcccgctgg tgagcaaaat ccaccagaaa aagtgctgt cttactacgc    3480 caaagccaaa gcagaaggtg ccaatattgt tcttggtggc ggcgttccca atatgccaga    3540
tgacctgaaa gacggctgct gggtcgaacc caccatctgg actggcctgc cgagagttc    3600 acctattgtt cgtgaagaaa ttttttggccc atgctgccat atccagccgt ttgacaccga    3660
agaagaggtg ctgaatatgg tcaacgacag cccctacggc ctggccactt ctattcacac    3720
ccaggatatc agccgagcca gccgtcttgc aacgcaaatc gaggtgggtc tgtgctggat    3780
```

```
caacagctgg ttcctgcgtg atttgcgcac acccTttggc ggctccaagc agtcgggtat    3840
cgggcgtgaa ggtggcctgc attcgctgga gttctacacc gaactgcgca acgtgatgat    3900
caagtattga gaatattgtg ccccattttt tttataagaa actcctatga agctttatta    3960
ctctcctggc gcttgctcgc tgtcacccca cattgccctg cgcgaagccg gtctggactt    4020
tgacttggtc aaggtcgatc tcaaaaccaa gaaaaccgat gctggtgacg attactttgc    4080
agtgaacccc agcggctatg tgccctgttt gcagatcgac gatggtcgca tgctcaccga    4140
aggcccgcc atcgtgcaat acatcgctga ccaagcggg ggcaaaaaac ttgcgccgct    4200
caacggcacg tttgagcgct atcaactaca gcagtggctt aactttattt ccaccgagat    4260
tcataaaagt ttttccccgc tgttcaaccc cgatgccagc gctgactcca aggctacggc    4320
gcgcaagact ttggatgccc gcttggcgac agcagcagca caactttcca agacaccta    4380
tttgcttgga gagagctact ctgtcgccga catctacctg tttgttacct tgggctgggc    4440
tggctatgtg ggtgtggact tggcgccatg gcctgcgttg caacactttt cggcccgggt    4500
ggcctcccgc gatgccgttc aggccacctt gcgcgcagaa ggtttgattc aggcctgaac    4560
attttgcccg cgcccgctgc gacgactgcg gacacgactt cctggtcgcc ttctcgtgca    4620
aaggcagggg tgtctgcccc tcatgcaaca cccggcgcat ggctgagacg gcggcacacc    4680
tcaccgacca tgtgtttccc cgcctgccgg tgcgccagtg ggtgctgtcg gtgcccaaac    4740
ggctgcggta ctacatgcag cgagagggcc cggtgctggg catggtgctg cgcatcttcc    4800
tacgcgtcat cgcgcaaacg ctgcaagcca acagccctgg tgcggccaat gtggacaagg    4860
cagcactgca cataggcgca gtcgccttca tccaccgctt tggctccagt ctgaacgagc    4920
atgtgcactt ccatgtctgc gcagtcgatg gcgtgtttga ggaagtggcg ggcgaggagg    4980
gcgatgctgc tgatgcagct tctcaaagct caccatcgcg catcatcttc caccccgcca    5040
ccggcgtgac tgcggatgcc gtgggtcagg tgcaggccag cttacgcaaa cgcatcctgc    5100
gcgccttgt cggacggggc ctgctggaga gtttcgaggc caagagatg ctgggctaca    5160
agcacagcgg ttttcggcg gactccagcg tgtgcatagc ggcgcacgac cgcgccgggc    5220
tggagcggct gctgcgctac tgcgcccgcc cgccgtttgc catggagcgg ctgcgcaaag    5280
cgggcagcga gctggtctac cgctgcgcca agcagcacag cgagcccggc agcctgcctc    5340
acaacaagcg cggcgtaaag gccgatgaga tcaccctcac cccgctggag ctgattgaac    5400
gtatcgccaa gctggtgccc cgccgcgca cgcaccgcca ccgctacttt ggcgtgctgg    5460
caccgaactc accccttgagg cctgccgtca cggcgttggc gcgtgatgca gcggtgaaac    5520
cggcgcaggt gcaagccgag ccagccagca cggctgcagg cgagggcgca cttggggtaa    5580
gaagcccact gccaacccag accgagcccg cccagccggt gccacccaag cgcccggcgc    5640
actatttgtg ggcggtgctg atggcccgta tctacgaggt gttcccgctg ctgtgccccca    5700
tctgcggcgg gcaaatgcac atcatcgcct tcatcacaca cagtgccgat atccgccaaa    5760
tactggagca catcggggtg gagacggagc gccgcacat cacccgggca cgcgggccgc    5820
cactgtggga cgagtgcgac gcgcaagccg cagagggcgt ggagccagcc ccagactggg    5880
atgaagcgac ccaaccggcc ccggacttcg aggtcgatca gcgcgtcagt ggtagggtg    5940
gcaacagcgg ttaacagtgg ttttgccaac gttgcgaggc agcgctgcgc ctgtcaccgc    6000
caaaaacggg tcataccgaa aaatctcggg caactggctt tgagaaatca acccagcagt    6060
cccctgtgtg catgcctgag acgccccaaa cgtgtgctat acttgtgctc atgcggttgg    6120
atttcctatc ccccgacctg ccatagccgg cgcgccccac cctcaacctt tccaggcgga    6180
```

```
gccccccat gacccagacg cccaaccaac tcgccgaagc gatctgggcc gcccgccagg   6240
ccggtcggac actggacgcc gcagccacca tcggcacgcc cgacctcgcc accgcctacg   6300
ccatccagcg cgcgctgctc ggcctgcgcc tggccgccgg cgagcgcgtg tcgggtgga    6360
agctgggtta cacgtcggaa gtgatgcgcc gccagatggg catagcccgg cccaacatcg   6420
ggccgctgac cgaccggatg ctgctgaact cgggcgacgc ggtgcacgag cgcctggtgc   6480
agccgcggt cgaacccgag atcgggctgc gcctccaaac cgccctcgac gcgcggcacg    6540
cgcccgtcga ccgccacacc gtggtcgccg ccgtggaggg cgcctacgcc tgcctcgaag   6600
tcgtgcactc cacctggaca ggctaccgct tcaacctcga acagaacacc gccgacaact   6660
cgtccgccgg ccaggtcgtc gtcgggccac gcctgccggt gaccgacctg atggcggcgg   6720
gcaccgtggc ggtgcgcctg cacgacggca gccaccacac gctgggacag ggcgtgggcg   6780
ccgatgccga cggccacccc ctggacgcgg tggcgcggct ggcgcgggag ctggccgcgt   6840
ttggtcagcg gctggaggcg ggtgatctgg tgatcacggg tgggctgaca aaggcttgtg   6900
agctggaggt ggggggagg ttgacgggag tgttttcgtt tggggacgct tggtcggtag    6960
atgtgactgt gcggcgtctg tgaaacgaca cttgataggt gcggatcgcc tgcacatcaa   7020
cccggtcaac gaacggctcc atcaaagacg ccagtgcagc gtgagcggtc gcgtgacacc   7080
ttgaccagtg agcggccggt ggaggcgcct ctacgatggc ctgcagagag gtcgagtgac   7140
agccaccagc cttgtgcgga cttcggccgc gatcaaatga agcgctgcca cgggtcggcg   7200
ccgagccgac cgcgcaagcc cttcctcaag caactgtatg cctgcaaggg gtatccgctt   7260
agctccatca gccccattga cactgtgatt tcatccagca atggtatccg attgcctctc   7320
cccggtgttc ttgctcacga catccccata cgtcactggc ggcgtcacca ccgcttgctg   7380
cagcaagcgt taaaacagca tcccgcgtga gctggatgtg cgccggttga aacgaacac    7440
gaattcatcg agataggcgt ccaggtgttc gggttgcaca gaaccgtggt gcgttcccag   7500
cacccagcgc tgtaccaacg aggcgacccg gtgcactccc gccatggaga catgggtgct   7560
cctcgttttc agtgcaataa gtgacggtac gcaaagctag cactggcgcg ggggtggtct   7620
gggtagaccg ttgatttcat tgactttcct gttcgctttg taaacgggta tggtggcctc   7680
ccactttga ggttcacgat gcagggttgg cacacaacgt ttttggggat gcgtgggctc    7740
ccccgcgata tcagcgactt cgagatgaag gcattttca ccttcgatgg tgccgagcgc     7800
gacgcaatca atgcacgccg aggtgattcc cacaagcttg gtctggcgct ccatattggg   7860
gttgtaagcc ggaaacccag aaatttccgt cagccgatca acatggcttg tctcgcgctt   7920
ggtcgatgag ttcctgcatc gcccgcatga cttcttcgtg ggtgtacgac ttggcgttgg   7980
ggtcgtcggc ctctcggaga gcttcctcga cctcgcgggt catccgcgca tattcttccg   8040
gccacagcgc ttgctccatg cgcagcgacg cctgcccaag caggtgcagc aggccgaaca   8100
gccgcatgtc attggtggcg acgacgtgct ctcgaatccg ctcctggatc acctcgcagg   8160
cccgatgcgc ctctggcgtc gccgtgccct cgtagccggc tgggagttct gcttcttcag   8220
cgattcgcgc ccaagcgata gccagcgcct cgatggtgga caggttcatt tgctcatcca   8280
cttgcgcagc agacgctttt tcagggaggc gcgctcttgc ggattgcgtc ccttgtggtt   8340
ggcaatgcga tccgccgtgg cggcctggcg cttgatgggc cagtaggagc ggccatcctt   8400
acccatcgca cagacgttgc tgacctggtt ttccagtaga ggcagatggg cgcatagagc   8460
ttccggcgac gcgctggcca gcgcggtgcg ctcgtgagtt cgccagcgct gatgccagag   8520
```

-continued

```
tttcttgtcc tcgcgctcgc tacggcaggt cgtgtgccca acgatgggcg ttttgcggcg    8580
gctgcggctc atgatgtggt tgtctccaag aacattcagg acaggctttc tgggtagagc    8640
gccgtcaacc gggacagggt ttcttgcact tgttccagcg aggtcatcag atgatcaacc    8700
tgatcctgaa gatccacggc gagatcaaat agctcagcca ctcggctgcg tgatccctcg    8760
ttgaacgcgg ccattgccag ttgatgcagc ttcaacaggt cggtgcgcag ttgcggaggt    8820
gcgccgtctg cgctgtcatt caaatcgccg cgcagcacgt ccacggcatc gactgcacgc    8880
agcagtgccg tggtatcgaa attctcggga gtcagttcgt cccattcgtc gtcggtgatg    8940
cgggctgcca tcaggagggc tccgattaag cggttgcgag cgttagatgc ccgatcggct    9000
cggctgctgg ccgtaccttg atttcgatgt cgtagccgag gcgattcaga caatccatca    9060
gcttgcgttc ggatagattg gtgaagtcgc cgcgcatcat gcccgacacc ttcggttgcg    9120
ggatgcccat gcgtttggcc gccgcttgtt gagtcagccc aagggcgcgc atggccctcc    9180
tgatctcgac caccaggccg gtcttgatct tgagcttttc agcgtcaggc agtccaaggt    9240
cggcaaagac gttgcccgag ctgcgctgaa cctcgacgcc ttcaatgatt cgttttgca    9300 tttcgtagct cctgtgccaa tacctcggcc accttcagcc gagcgcggat gatgtccatg    9360
tcggcctttg gcgtggcgat tccgctcttg ctcttcttct ggaagcagtg caggacgaac    9420
accgcttccg caaacttgac cgtgtatacc gctcgatagg tgccgccggc atcgtcttcg    9480
acgacctcca gcacgccggc accaccgaac cccttgagca cctttgctgc gtcatcctga    9540
tcgcctatct gcgccaacga gagcgcgtaa ccgaaacggc gacgcacgtc ggacggcaac    9600
gccatcaaat cctgtggct gctcgcgatc cattcgagcg gttttttctt gtttgtcatg    9660
acggaatttt atacctgttc aggtaatgat gtaaacgcgg caacctcaag gaggtgtcgt    9720
aaaacatttg ttttgcgaca ggctgtcagc cgccgctgtg ctacctgtcg ttttcagaag    9780
acgaccgcac catctgactg gatgtaacgc ctggtgtgca tacggctcct gacagcccaa    9840
tatcaggagt cgtctgcacc aatctcgact atgctcaata tcgtgtgca ccaaagcgag    9900 gtttgggcat gacatcagac actccaccga ttgccgcgca aggcgtggcc accctgcccg    9960
acgaggcatg ggcgcaagcc cggcaccgga cggaaatcat cgggccactg cagcgcttg   10020 aggtggtcgg gcatgaagcc gccgatgagg cagcccaagc gctgggcctg tcccggcgac   10080
aggtatatgt cctgatccgt cgcgcccggc agggtactgg cctggtaaca gacctgacgc   10140
ccggccgatc cggcggcggc aaaggcaagg ggcgcttgcc ggaaccggtc gagcgcatca   10200
tccgcgagct gctgcaaaag cgcttcctga ccaagcagaa acgcagcctg cggcgttcc   10260 accgcgaagt cgcgcaggcg tgcaaaaccc agaagctgcc ggtgccggcg cgcaacaccg   10320
tggcccagcg gattgccgga ctacacccgg cgaaaatagc ccgcagccgg ggcgggcagg   10380
acgctgcccg tcccttgcaa ggcgcgggtg gcattccgcc cgaagtcacc atgccgctgg   10440
aacaggtgca gatcgaccac accgtcatcg acctgatcgt ggtcgacgag cgcgaccggc   10500
aaccgattgg ccgcccatat ttgaccctcg ccatcgacgt gttcacgcgc tgcgtactcg   10560
gcatggtggt cacgctggaa gcgccgtccg ccgtctcggt cggcctatgc ctcgcgcatg   10620
ccgcctgcga caagcggccc tggctggaag ggctgaatgt ggaaatggac tggccgatga   10680
gcggcaagcc caggctgctc tatctggaca acgcggccga gttcaaaagc gaagcgctgc   10740
gccgtggctg cgaacagcat ggcatccggc tggactatcg cccaccaggc cagccgcact   10800
acggcggcat cgtggaacgg atcatcggca cggcgatgca gatgatccac gacgaattac   10860
cggggacgac cttctccaat cccggccagc gcggcgagta cgattccgag aagatggcca   10920
```

-continued

```
ccctgacgct gcgcgagctg gagcgctggc tcgcgttggc ggtaggcacc tatcacggct   10980
ccgtgcacaa cggcctgctc cagccgccgg ccgcgcgctg ggccgaggcc gtggagcgcg   11040
ttggcgtccc ggccgtcgtt acccgcccca ccgcgttttt ggtcgatttc ctgccggtga   11100
tccgccgcac cctgacccgc accggctttg tcatcgacca catccactac tacgccgacg   11160
ccctcaagcc gtggattgcc cggcgcgagc gcttgcccgc cttcctgatc cggcgcgatc   11220
cgcgcgacat cagccgcatc tgggtactgg aaccggaagg tcagcactat ctggagatcc   11280
actaccgcac cttgtcccat ccggccgtca ccctctggga caacgccag cgctggcca    11340 aattgcgtca gctcgggcgc gagcaggtgg acgagtcggc gctgttccgc atgatcgggc   11400
agatgcgcga gatcgtgacc accgcccaga aggccacgcg caaggcgcgg cgcgacgctg   11460
atcgccgcca gcacctcaag acgtcggagc caccggccaa gcccataccg ccggatgtgg   11520
acatggctga cccgcaggca gacaacctgc cgccggccaa accgttcgat cagatcgagg   11580
agtggtagcc gtggacgaat atcccgtcat tgacctgtcc cacctgctgc agcggcaca   11640 gggtttggcc aggctgccgg cagacgagcg catccagccg attcgcgccg accgctggat   11700
cggctacccg cgcgcggtcg aggcgctgaa ccggctggaa actctgtatg cgtggccgaa   11760
caagcaacgc atgccaaacc tgctgctggt cggcccacc aacaacggca agtcgatgat    11820
cgtcgagaaa ttccggcggg cgcacccggt cggcaccgac gctgaccaag aacatatccc   11880
ggtgctggtc gtgcagatgc cgtcagagcc atcggtgatc cgcttctatg tcgcgctgct   11940
ggctgcgatg ggcgcgccgc tgcgcccgcg cccacggctg ccggaaatgg agcaactggc   12000
gctggccctg ctgcgcaagg tcggcgtgcg catgctggtg atcgacgaac tgcacaatgt   12060
actggctggc aacagcgtta accggcgcga gttcctcaac ctgctgcgct tcctcggcaa   12120
cgagctgcgt atcccccctgg tcggggtcgg cacgcgcgag gcgtacctgg ccatccgttc   12180
ggacgatcag ttggaaaacc gcttcgagcc gatgctgctg ccgccgtggg aggccaatga   12240
ggactgctgc tcgctgctgg ccagcttcgc ggcgtcactc ccgctacggc ggccatcccc   12300
gattgccacg ctggacatgg cccgctacct gctcacccgg agcgaaggca ccatcggcga   12360
gcttgcacat ctgctggtgg cggcggccgt cgccgccgtg gagagtggcg aggaagcgat   12420
caaccaccgc acgtcagca tggccgacta catcggcccc agtgagcggc ggcgacagtt    12480
cgagcgggaa ctgatgtgaa gtccgcgccg cgctggccgc tgcatccggc acccaaggaa   12540
ggcgaagccc tgtcctcatg gctcaaccgg gtcgccgcct gctaccagat ggacgtgcac   12600
gagctgctgg cccacgatct tggtcacagc caacttgatg acctggatac cgcaccatcc   12660
ttgtcgttgc tgacggcgct ctgccagcgc agtggcgtcg agctggagcg gttgcgcagc   12720
atgagtcttg caggctgggt gccgtggctc ctcgacagtc tcgacgattc ggtaccagca   12780
gccttggaaa cctatacatt ccaatgcgcg gtgctcctgc ccaagcgcac ccgcaaggtg   12840
cggtccatca ctcgctggcg tgcctggcta ccgagccaga cgattcgccg ggcgtgtccg   12900
cagtgtctga acgatccaac gaatcaagct gtgctactcg tctggcagct ccccttgatg   12960
ctgagctgcc cgcagcatgg ctgctggctg gagtcctact ggggcatgcc cggccggtat   13020
cttcagtggg aaatcgccga tgctgcgccg cgccctgccg atgacgcaat cgcctgcatg   13080
gaccggcgca cctggcaggc gctgacgacg ggttttgtgg agctgccgcg tcggcgtgtc   13140
cacgccggct tgtggttccg gctgctgcgc acctgcttg atgagctgaa cacgccgctc    13200
tcgcactgcg gcagttgctc ggcgagcatc cgccatgtct gggagcgctg cggccatccg   13260
```

```
ctgcgcgccg ggcagagtct gtggcgtccc tacgagattc tggccccggc ggtgcagtgg   13320
cagatgctgg aggcggcggc caccgccatc acgctgatcg agtcaaaggc gctgatcccg   13380
cgcggggaac aggccgcgct gtttcagacg gagccgcaca ctggtttcac caacggcctg   13440
ccggcgaagg tgccgaagcc ggaacccatc aaccactggc aacgagcagc ccaggccatc   13500
gatgaggcca tcattgaagc gcgacacaac ccggagacgg cccgcttgct gttcacactg   13560
gcgtcctacg ggcgacgcga ccccgaatcc ctggaacgtt tgcgcgccac gttcaccaag   13620
gagggcatcc cgccggagtt tttgtcacat tacgagcctg aatggccgtt tgcaggtctt   13680
agactaaatg acgggttaag tgacagtttt tgacggcgag aactttctgg ctcacactgt   13740
cacataatcg aacgtatatg tgacaggtac gacatgctga taggctacat gcgggtatcg   13800
aaggcggacg gctcccaggc taccgatttg cagcgcgacg cgctgattgc cgccggggtc   13860
gatccagtac atctttacga ggaccaggca tccggcatgc gcgaggatcg gcccggcttg   13920
acgagctgcc tgaaggcgtt gcgaactggc gacacactgg tcgtgtggaa actggatcgg   13980
ctcggacgcg acctgcgaca tctcatcaac accgtgcacg acctgactgg gcgcggcatc   14040
ggcttgaagg tattaaccgg gcacggcgcg gccatcgaca ccacgaccgc cgccggcaag   14100
ctggtctttg gcatcttcgc cgccctggcc gagttcgagc gcgagttgat cgcggagcgc   14160
acgattgccg gcctagcctc ggcccgcgcg cgcgggcgga aaggcggccg gccgttcaag   14220
atgaccgccg ccaagctgcg gctggcgatg gcggcaatgg gtcagccaga gaccaaggtc   14280
ggcgacctgt gccaggaact tggcgtcacg cggcagaccc tgtatcggca tgtttcaccc   14340
aagggtgagc tacgtccaga tggcgagaag ctactcagcc gaatttgatg ccggcatgag   14400
gcaacgtagc gacagcgtgg tttgtctcaa tgggaagcgc tcatgatcga tctttgaagg   14460
cccgcagcag tcgtgtcaca gacaggacga acaaaccggt cagcgtgagg gctgcgatac   14520
cccagtactc tccgatgaac gcgccggccg tcgtgccggc cagcacaatg gcgagaatcg   14580
gcaaatggca gggacaggtg agcacggcca gcgcgcccca caggtagccg gtgatcggtt   14640
tgtgcgtctc ggacggcaag cgctcggggc tgttcatggc agactctccg cgtgctgtgc   14700
cggctcggtc ggcatggtgg ccaactgcac ctccagatcg gccaacgctt cgcgccgacg   14760
ctcgacgaac tggcgcagaa cggcaagctg cgcggccgct tcatcgccgt ccgcagcatc   14820
cagcgcccgg cacagccgcg ccagcgcgtc caggccgatg cccgcctcga aggccgcccg   14880
cacgaagcac agccgttgca aggcggcatc atcgaacagg ccatagccgc ccggggtgca   14940
cgccaccgga cgcagcaatc cgcgcagcag gtagtcgcgc acgatatgca cgctcacccc   15000
ggcatcaagg gccagccggg acacggtgta ggcgctcatt gaaaacctcc tttttttatc   15060
cagcgcagca ggaaagctgc ttcacgtcct tgttgaaggt ctgcgccgca agcttcaacc   15120
cctcgaccat tgtcaggtag gggaacaact ggtcggccag ttcctgcacc gtcatgcggt   15180
tgcggatggc gagcaccgcc gtctggatca gttcgcccgc ttccggggcc accgcctgca   15240
cgccgatgag ccgtccgcta ccttcctcga tgaccagctt gatgaagccg cgtgtgtcga   15300
agttggcaag cgctcgcgga acgttgtcga gtgtcagcgt gcgactgtcg gtctcgatgc   15360
catcgtggtg cgcttccgcc tcgctgtagc ccacggtggc gacttgcggg tcggtgaaca   15420
ccactgccgg catcgcggtc agattgaggg ctgcgtcgcc gccggtcatg ttgatcgcgg   15480
cacgggtgcc ggcggccgct gccacgtaga cgaactgcgg ctggtcggtg cagtcgccgg   15540
ccgcgtagat gttcgggttg ctcgtgcgca tgccttggtc gataacgatg gcccccttgcg  15600 cattgacagt gaccccgcc gcgtccagcg cgaggctgcg cgtattcggt gcccgaccgg   15660
```

```
tggcaaccag caacttgtca gcgcgcaatt caccgtgtcc ggtggtcagc acgaattcgc   15720
cgttcacatg ggcgacctgg ctggcttgcg tgtgctccag cacctcgatg ccctcggcgc   15780
ggaaagcggc tgtcacggcc tcgccgatgg ccgggtcttc ccggaagaac aaggtgctgc   15840
gtgccaggat cgtgacctgg ctgccagccg gggcaaaggc ttgcgccagt tccaacgcca   15900
ccaccgacga accgatcacg gccaggcgtg cgggaatggt gtcgctgaca agcgcttcgg   15960
tggaagtcca gtagggtgac tctttcaggc ccggaatcgg cggcacggcc ggactggcac   16020
cggtggcgac caggcagcgg tcgaacgtta cctcgcgctc gccaccctcg ttcaaacgga   16080
cgaccaggct ctggtcgtcc ttgaaacgcg cttcaccgtg caaaacggtg atggctggat   16140
tgccgtccag gatgccttcg tatttggcgt gccgcagttc atcgacacgg gcctgctgct   16200
gggccagcag tttgctgcgg tcaatcgcag gcacagttgc cgcaataccg ccgtcgaacg   16260
gactttcccg gcgcagatgg gcaatatggg cagcgcggat catgatcttg gacggcacac   16320
agccgatatt gacgcaggtg ccgccgatgg tgccgcgttc gatcagcgtg accgtcgcgc   16380
cttgctcgac ggccttcagc gccgccgcca tcgcggcccc gccgctgcca atgatggcga   16440
tatgcaaacc ggcgccctca agtgcatcac ggattttttgg ttcatctttg aaatcaccaa   16500
cccggatcga gccttgataa cccaatgcgg cgatggcggc cagcagttgg ttgtggctca   16560
cggcggtgtc tgccatgact tgcgcgcggc tttctggata ggacaccaca gcggcattca   16620
cgccgggaat cttttccaaa gcatctttga catgggtggc gcaggatgtg caggtcatgc   16680
cattcacggt gatttcggtc atttttttac tccattgaat ttcggggtgc agcaggcatc   16740
ggcttggcgt tttcgttgga tggcgtagat ggtcaagccg atgaaaatcg ccagcgcagg   16800
cagcagcaca tagtccagat agccggtcag cgcggacaag ccgaccacac cgagcaaaat   16860
gaccagaaca ggggtgaagc aacacagcgc cacgagggtt gtgccaatga tgctgacccg   16920
cagcagtgtc ttcgggtctt tcatgatcag ttcttgactg atgatgggta gcccgcatcc   16980
tcggtagcct tggtcagttt ctgcacgctg gtcttggcat catcgaaggt gaccaccgct   17040
tcgcgcgtct cgaaggtcac gtcaacttta ctgacgccat cgaccttgga aatcgccttc   17100
ttgacagtga tcggacaggc cgagcaggtc atgcccggta cggacagcgt aacggtctgg   17160
gtggcggccc acacgggggc aacaacggca gcgagggcaa gggcggaaag cagcttttc   17220 atggtgaact cctgtgatca atagaaaaat ggcacgacgt agggaaatcc gagcgcgacc   17280
aaaaccagca cggccacgcc ccagaaaatg agcttgtaag tagctcgcac ttggggaatc   17340
gcgcaaacct cacccggttt gcaggcggct gacggccggt agatgcgccg ccaggcgaag   17400
aacaacgcca ccagcgccac gccgataaag atgggcgat agggttccaa caccgtcaag   17460
ttgccgatcc aagcgccgct gaaccccaag gcgatcagaa ccagcggccc gaggcagcaa   17520
gccgaggcga ggatggcggc cagcccgcca gtgaagagcg cgccgcgccc gttttgaggt   17580
tcagacatac gtttgtcctt tcgaatctga attggatagc ttaagcttac ttccgtagtt   17640
atgtacggag tcaagcgata tggaaaacaa tttggagaac ctgaccattg gcgttttcgc   17700
caggacggcc ggggtcaatg tggagaccat ccggttctat cagcgcaagg gcttgctccc   17760
ggaaccggac aagccttacg gcagcattcg ccgctatggc gagacggatg taacgcgggt   17820
gcgcttcgtg aaatcagccc agcggttggg cttcagcctg gatgagatcg ccgagctgct   17880
gcggctggag gatggcaccc attgcgagga agccagcagc ctggccgagc acaagctcaa   17940
ggacgtgcgc gagaggatgg ctgacctggc gcgcatggag gccgtgctgt ctgatttggt   18000
```

```
gtgcgcctgc catgcgcgga aggggaacgt ttcctgcccg ctgattgcgt cactgcaagg   18060
gaagaaagaa ccgcgcagtg cggacgcggt gtagcccgag ggaactacgc cttagcgtgc   18120
tttattttcc gttttctgag gcgactccaa cgtcagaaaa gaccgtgcgg tcgacttttg   18180
atatttcgtg ctgtcgcctt ctgaaagtga cactacctgt gcaacacccc ctcaaaaatg   18240
tacggaaaac tctatcgcta ttcactatta tgcggaaacc tgttttttga tggttatccgc   18300 ctatgttggt tggctacatg cgcgtgtcgt cggactccga ccgccagagc acggacttgc   18360
agcgcgacgc gctgctcgcc gccggcgtcg atccgcgtca cctgtttgag gatcgtgcct   18420
ctggcgcgaa ggatgaccgt gccggcttgg cgcgggcgct tgagttcgtt cgagccggcg   18480
atgtgctggt ggtgtggaaa ctcgaccggc tcggtcgctc gctgtcgcac ctgctcgcca   18540
ttgtgacttc gctcaaggac aagcgggtgg cgttccgctc gctgacagag aacctggaca   18600
ctacgacgcc ctcgggcgaa ttcctgttcc aggtgttcgg tgcgctcgcg cagtacgagc   18660
gcgccttgat tcaggagcgc gtcgtcgcgg gcttggccgc cgcacgcaaa cgcggccgga   18720
tcggcggccg gccgcaggcg atcactggtg agaagctgga cgccatcgtc gccgcgctcg   18780
atggcggcat gtctaaggcg gcggtgtgcc gcaacttcaa tgtcaagcgc actacgttga   18840
tcgaaacatt gacgcgagca ggttggcgtg gtgcgggaag gacggtcgat gagcaacaag   18900
aataagctac tcaccgtctt ttctgacgca gagcaggaag ccttgtaccg cctaccggac   18960
ttcgacgatg ctcagcggct ggaatacctg gcgttggccg aatctgaact ggcgttcgcc   19020
agcagccggc ctagcctgca ggcccaagtc tattgcgtct tgcagatcgg ctacttcaag   19080
gccaagcatg ctttcttccg cttcgattgg catgaggtcg aggacgattg cgccttcgtg   19140
ctgagtcgct atttccacgg cgaagcgttc gaacgcaagg cgatcaccaa gcatgagcac   19200
tacagccaga ggggtcagat cgccgaactg ttcggctacc ggtcgtgggc ggctagcttc   19260
ctgccgcaac tggcacagca ggctgaacag atcgtgcggc gcgacgtaat gccaggattc   19320
gtggccgccg aactgatcgt ttggctcagc gagcacaaaa tcatccggcc cggccacacc   19380
accttacaag agctggtcag tgaagccctg tccaccgaac gcaggcgctt gggcggcttg   19440
ctggcagaag tgttggacga atcggccaaa gctgcgctgg gccagctcct ggtgcgtgac   19500
gacaccctgt ctcaactggc agcgctcaag caggacgcta aagatttcgg ctggcgtcag   19560
atggcagggg agcgcgagaa gcgcgccacg ctgaagtcct tgcacgggat cgccaaggcg   19620
ctgctgccca agtcgggcat ctcgcagcag aacctgctgt actacgcgag cctggcgaac   19680
ttctataccg tccatgacct gcgccacctg aaggcggagc agacccggct ctacctgctg   19740
tgctatgcct gggtacgtta ccggcagctc accgacaacc tggtcgacgc gatggccttc   19800
cacatgaaaa aacttgagga cgagagccgc acgggtgcga acagtccttt gtcgccgaa   19860 cagctgcgac gccatcagga aacgccgcag gttggccgcc tgctgtcgct gtacgtggac   19920
gacagcgtgg ccgatccgac gccgttcggc gaggtgcgcc aacgcgccta caaatcatg   19980 tccagggaat tgctgcaaaa cacggcgcag cgcatgagcg tcaagccact gaacaaactg   20040
gcgctgcact ggcaggcggt ggacggcctg gccgaacgca ttcgacgcca tctacggccg   20100
ctgtacgtcg cgctcgactt cgccggcacg gcccccgata acccatggct cgcggcgctg   20160
acttgggcca agagcgtgtt cgccaagcag cagcgcctat cacaacggcc actcgacgaa   20220
tgtccggcgg caacgctgcc gaaacgcttg cgtccgtacc tgctgatgtt cgatgccgaa   20280
ggcacgccga caggcctgca tgccgatcgt tacgaattct ggctttaccg tcaggtcagg   20340
aaacgcttcc aggcgggcga gctctacatt gacgacagct gcagcaccg gcatttgtcc   20400
```

-continued

```
gacgagttgg tttcgatgga cgagaaagcc gccgtgctcg cgcagatgga catcccctc    20460 ctgcggcagc cggtcagtgc ccagctcgat gcactggcgg ccgagttgcg tgcgcaatgg   20520
gtggcgttca atcgcgagct gaaacagggc aagctgacgc acctggaata cgacaaggac   20580
acgcagagac tgacctggcg caagcccaag ggggagaacc agaaggcgcg cgagcaagct   20640
ctctacgagc aactgccata ctgcgatgtc gccgacgtgt tcgcttcgt caacggccag    20700 tgccagttcc tgtcggcgct gacaccattg cagccacgct atgcgaagaa ggtagccgac   20760
gccgacagtc tgatggcggt gatcattgcc caagccatga accacggcaa ccaggttatg   20820
gcacgtacca gcgacatccc gtaccacgtc ctggagagta cctaccagca gtacctgcgc   20880
caggcgacgc tacatgtggc caacgattgc atcagcaacg ccatcgccgc actgccgatc   20940
ttcccgcatt actcgttcga cctcgattcg ttgtacggtg ccgttgatgg gcagaaattc   21000
ggcgtcgagc gaccaactgt gaaggcgcgc tactcgcgca aatatttcgg ccgcggcaag   21060
ggcgtcgtcg cctacacgct gctgtgcaat cacgtgccgt tgaacggcta cctgataggc   21120
gcacacgagt acgaggctca ccacgtgttc gacatctggt accgcaacac gtcggacatc   21180
gtgccgagcg cgatcaccgg cgacatgcac agcatcaaca aggccaactt cgccatcctg   21240
cactggttcg gacttcgttt cgagccgcgc ttcaccgacc tcgacgacca gttgcaggag   21300
ctgtattgcg ccgatgatct ggcattgtac gagaaatgcc tgatccggcc ggctggccag   21360
atcgaccggc aactcatcgt cggtgagaag gcgaacatcg accgaatcgt cgccacactg   21420
ggcctgaagg aaatgacgca gggcacgctg atccgcaagc tgtgcaccta tacggcgccg   21480
aacccgacgc ggcgcgcaat cttcgagttc gacaagctca tccgcagtat ctacacactg   21540
cgctacctgc gcgacccgca actggagcgt aatgttcacc gctcgcagaa ccgcattgag   21600
tcctatcacc agctacgctc gaccatcgcc caagtcggtg ggaagaagga attgaccggc   21660
cgcaccgaca tcgaaatcga gatcagcaac cagtgcgcca ggctgatcgg caacgcgatc   21720
atcttctaca actcggcgat cctgtccctg ctgctgacga agtacgaggc agctggcaat   21780
gccaaggcgc tggcgttgat cacgcagatg tcgccagcgg cctggcggca catcctgctg   21840
aacgggcatt acaccttcca gactgacggc aagttcatcg acctggatgc gctcgtggcg   21900
ggactggagc tgggctgacg gaaatttctg ggattccggc gtacaacccc ttattggtgt   21960
ggctcgatgg tacgactgga agctgggcaa gttttccgac cgggacctgg ccaaactggt   22020
cggcaccagc gagggcagca tacgccgccg acgtgttcag ttcggaatcg aggtttactc   22080
ggtcgcggtg gccatcgccc cttaccagca cctgctgggc gtggagtcgg acaggtctgt   22140
ctcggccaaa tgtggtgtat cggtgaagag tgtcaaagct taccgcgagt cccagggcat   22200
caagcccagg tccaaggcca cacggcgcat tcagcgcctt ccgctcgatc atcccgtcag   22260
gccgtacaag agcgcgctgg gcctggttcc cgatgaggac attgcccagg cctcgggcgt   22320
ggccgtagaa gtcgtgcagg cgctgcgcga ggcgttcggc ctggatgctg tggcgccctc   22380
ccctgacctg gccaagccgg cgcctgtcga ggactaccac ggccccggac tcggttacga   22440
atcgctcctg gcaccatgt ctgccgccaa gatcagccgc gaagtgggcg tgcccattgg   22500
ggttgtggaa gctcgccagc agtacctggg cattgcaccc tatcgccggg tgtcgcgtgc   22560
ggagcggtac gcgcacttgt tcggcctggt cccgaataac gtgctggcca aactcgcagg   22620
cgtgtcgcat gagcgcatcg cagacatgcg ccggtcgaga ggcgtctagc gggcagcaaa   22680 aagggggccga agccccttg ctgattacag accgaatgcc ctgccctttt ctttgggctg   22740
```

```
tttggccggc aattgctggc cttgctgttg cttctgcacg gcgtccttct gtttgccagc  22800
ctggtcgtgc cctttgcgct cgagcgcatg ccgctggagc tgcttgatat ccagggcgcc  22860
ggccttggcg ttcaagcggc tgatcgcatc ccccagcttc tgccggttat cggtgaagat  22920
ttccgctgca tgacgggcgc ggctgatagc cacgtagtac acgtccttgg cggtggtgcg  22980
cgattgggtt tcaaggttga tgagcaccct gtcgcaggtg agaccctggg cgctgtgaac  23040
ggtcgaagca taggccaggc cgacgaacat agccgatgct gtgtccagct cgacctggcg  23100
gcctttgtct ccttcgagca ccacgcggtc gctgtggatc tccttcacca caaatcggtc  23160
gccgttggcc aagtcctttt cagcgtcgtt tcgggtgatt ttcacctgat ccccagcgac  23220
aagctctgtt ctctcgacgc tgtagaccga aagctttgta caacgggctg gagtgaattg  23280
cagcgtctcg ccttctggcc cgcgcacggt gagtttgttg ccggggccgg tgtcgagtac  23340
cacgtactgt acgccacgtt gcagcccgtt cttatagtcc acctcgggga cgacaatgct  23400
gcccttgccg tagtatttac tgtgccggcg ctcggcttgg gtcgtatcca gacggttgag  23460
caatggatac tccgcgccct gccctttcag tcccagcgcc tcccgcacgc cttcgttgat  23520
ttggatccga ctggcgttgg taccggtgat aattagagcc tggtcacgct cggccttcgt  23580
cattttggcg taggcgtcga caatcgcctg gtagcgtgcc ccgtcttcct tgatctcgcg  23640
tatctcgttc accagtggca gcgattgctt ggctttaccc tcggcggcca gcttcaccgc  23700
ctccagcaat tgcgggtcct tctgccgctg aatgtcggtc agccgggacg tttccatgcc  23760
ggctttcatc agctgctcga agggtttgcc ggcctcgatg gctttggttt gtgctacgtc  23820
gcccaggaag accacgcggg cgccggcagc ctcgatggtt ttcatggctt cgtgcatctg  23880
ccgcgcaggt attacgccgg cctcgtcgat gaacacgacg gtgttgctgt cgatcttctt  23940
atcgcgggcc ttgaggaacg attgcagagt acgagcctcc agaccctcgg cctggagcgc  24000
cttcacctgg ctaccatagg gcgccaggct ggtgacacgg tatccgttcg cctccagcag  24060
atccttggcc gctacagtca tgtagctttt gccgacgccg gcaaagccct ggacgccgat  24120
gaactggttt tgtgtgcggg cgatccgcat caccgaggcc tgctgttccg ccttcaagcc  24180
ccgatcggca aggaaggctt cggcggcttc tttagagatc cgtggctcaa ccgtaccgcg  24240
ccccattcgc tcgatttgca gcacctcgcg ttcgcgcttc tgcgcgatgt gcgtggtaaa  24300
acggttttca ccctggcgca gccgtccggt gcggatgccc tcatcaacga gcctggcggc  24360
ctctgagcgc gatttgccgg cgcggacaag ggttgccacc cattccttgc ggctgagctg  24420
tggcgcctct tcgcgggcct tctcggcggc cttccccttc tttccatcgg cagggttttg  24480
tgaagagtaa agcggttcct cgcggatcag gtggccagat gcggcacgcc gctcgatgcc  24540
ggcgcgcacg tcgtcgatgg tgagggcgcc gtacccgtgg cgcagcgcgg tatccatcag  24600
ctccttctga ccgataaccg cctggcgctc ggtcagactc ttgatcgcga attcgatcac  24660
ctggtcggca cggtactcca ggggcttctc gatctgcgga gtggcggcgc tgtttcgctc  24720
cctgccgcct tgcgcatcgg cgccgacgcc ggcccactcg cggctgtggt agtcgatacc  24780
caaagccctc gaccgttcaa gccaaacctg gcgcaattct tcgcggtcga ttccaccctg  24840
cttttttgtcg cgggtggcca gcgcggcctg gttcttttca gcatacgacg ctgtgctgcg  24900
gtccaggcct ttcgccgcta gcgctgcctc gatctgctgg ctgcgcgaac tgaattcgcg  24960
gatctgctcg tcggagaaat gcgccaggtc gaatgtaccg ttgcgctcat agcgcaactg  25020
gaagccggcc ttttccagct cgcgggccag ttccgccttg tagacgttgc ccaggaacat  25080
ggacgaattg aacacaccgt cattttttcag tgcccgccat tcgccgtcgc tacgctgggt  25140
```

```
catgttcagc acgaacgcat gggtatgcag gtcggggtcc agggcgcgtg aggtttcgtg   25200
tcggaacttg gccaccacca agttgttggt gttctcggta ccgtcttct tgttgaccgt    25260 tattcgggcc tgggacaacc gttcagcctc gcgaatggct gctgccaccg ccttatcgtg   25320
ggcttcgata tgctggcgt caccgtggac caaggcctgg agcgacacac ctttgggcgc    25380
tgaaaaggtg aggtcatacc caagcctttc cttgctgacc actttgccat cagcctcttt   25440
gacagtgcgc atgagcttcg tgctgtcgct aattcggcca tccaatagct cgcggaatcg   25500
ggcctgctct acttccccgg acaggcccaa tgcctcggcg ccggcacctt gccattgcat   25560
ggcgccgccg tcttttgcgt agtagtcatc cgcaccatcc gcgtagtacg acacgacttt   25620
gcccagtgat tgccgagaaa tggtcgtgat atcgagcatt tagatgatct caaggtttgg   25680
gacgatgccc ggtaccgggt tcgtgcgggt gaagttgatc gggtcgatgg tcacacgcgc   25740
aatcgggatg cttccgggga acgacaggaa gccttcgagg ttgttcaaag ccatgatctc   25800
cgacgacata acgatgcgct cgggtttcac atcctcgttc tcgctgcgag tgccccagtc   25860
accccagcgc gagctgcggc cttccttggt gcgcagtact tcatgctcgc tcaaggcttt   25920
ggacatgcgt tcggcggttg ccgtacccat gcggccaacg gccagggcaa ccattgtccg   25980
gtggttggcc agcatcgttt cagccagttt ctcgccatac acggattcga gctgggtgta   26040
ggactggtag ccagatacca cgcaaccgcc cttcttccgg ccccgagtca acatgtcgcc   26100
cagggtgggc agtcgttgca gcgattccag ctcgtcaagg aagtccaga tccggcgctt    26160 gggattggac ttcatcccaa gaatgctggt gaaaatggta tccacccagc aactaatcaa   26220
tgggcgcagc gcttcgcgca tgttctcgtc ccaagtgata aacaagttgc cgccgttagg   26280
atcttcgcac cactggcgca gcgaaaaatt gcctggtggc atatcaaaat gcgcaggtag   26340
tttattactg aggacaaacc ggacgctgcc tgtagcgcgc tcgttttcag taaacaaaga   26400
tacggctctt gtgccttta caaaagcctg aagagtttcc gagtcgcact cgttagtcca    26460
tcggaatact tcccgcatgc cagggttgcg cgtggtgtta tacagcttct tggccacctc   26520
tgcgaacagc agacggccat actggttcca ttcttccgag tcgttactgt ctgaaacttg   26580
aataatggat tttgcgtagc gctcgaaatc gtagtgacta cggatttcgt tatagaagtt   26640
ccaaccttcc gtcctggcat catatggatt caggatttta tcgcccttgc ggtagaaggt   26700
agataggaac tctccatcgg gatcaaggat taccatgcga tctttccgct gcatgcagcc   26760
atacatcatt tcgcggaaaa tcgtactctt acccgtaccc gtggcccgc caactgagaa    26820 gtgtgtcgcc tcggcagcaa taggaacagg cacccggca atagttattt gttcctcttt    26880
ctcctttgtc agtcgtttaa gctcacgctg ggagacaagt tggctaccac ggaaatactt   26940
atcaaagtga gcgccggcaa aagtggtctt gctcaacttc acgataagca cgcacaacgc   27000
aatcgcgagt atcagcccac caactaaagc aaccgcaagc ggccacaagg tgaacgtgtt   27060
tttcgccagg tagaacaccc tgtctcgggc gccttgcttt tcaattccat acatcagctt   27120
ggcggtaaag aaccacgcga acagtggcac cagcaccatg acggcgaggc agatttgaga   27180
tcgttggcgc tcgttcatca gctatccctc tttgatgaat cccatacgtc gaagcccagg   27240
cgctcgacct cggcctgggc ttccctctta gcatccggtt tggacgcggt gcgcagaagc   27300
aatagcagct cgatcaagat ggccatcgac tggcggtcga ttccagcggt cggctggccg   27360
tcaccgccag gccgttgatc gaggcgctgg aggatcattt ctagcgtgtc ctcctgctcc   27420
atctgccgga aaagctgccg gcgtacatac tccgaaatgt cgccctggga ccgctcttcc   27480
```

```
agctcgattt tctgtgtttc ggtgcatcga aagctcactg tgggcacgga tggtctcctt   27540
gtctgacgtg tgtcagacac aaaatacagc aaaatcaggg cttgcactca cttttgtctt   27600
acgcaggtat tacgcttttt cgcgagtcgt tgaaaatgct ttattttca acgacttagc    27660 gatgcgaagc attgcgtatg gtgtatagct cgttaaggga aaataccgct ctgcttttaa   27720
gggagaaaat agccgtctgc acccctcgga ggccgcaaaa aagcgtcctc ctgatccctc   27780
acgcgcagcg tgagggcttt tcgccgccc aggggtgcca ctgagtacgc attgaagaca    27840
accgagagac gatgtgaaga caccggagag acaaaaaagg gacttgccag agtcaaaagg   27900
gacggctaga gtacggatca gagacaaaga ggggacaaaa gtgcccgagg tcgataacga   27960
ggggtaagcg atgccactat cgcgactaaa accacggagc gattcggccc tggtgcggaa   28020
catgctcggc gagatcgagg ccgcactgac agccggagcc tcacgggagg atgtttggaa   28080
aacgctcaaa gaagagcacg ggatgggaat tggctttaac gggttttgca aggcgctgat   28140
gcgagcgagg gccgcaaggc aggagcgagc tggaacacca gcgacgacca ccccaccgcc   28200
accccgaccg gaaagtgatg gccagggaaa ggatgtggat tgcgcaatcc agaaagacga   28260
accaacgcca cccgaggcgg gcgcacccgt aaagggtcgc atcgtcacca gtagcgattt   28320
cgagaaagtc cactccatgg atttctctga tcttgatgat aaatatacgg gcaaaaggaa   28380
atagcgtatg aaacgagcga tcttgaacta cagcggcagc atcggcaaaa ccactattgc   28440
agcgcacctg ctctaccctc ggatgccagg cgcggcattc tttgccatcg agtcgattaa   28500
ccagtcggcc ctggacttgg gtattgccga agtggttacg atgcgaggcc gcgaagcggg   28560
cgagctgatt gaggatttgg tacttgaaga tatcgccatt attgacattg gcgcttctaa   28620
catcgaatcg ttctttgagg ctggatcgcg ctatcacggt ttcattgacg aaattgaaca   28680
gttcatcatt ccggtaactc ccgagcaaaa ggcctggcag gaaagcttga aaactgttga   28740
ggcgctggcg accatcggcg tttctcctga tcgcatcatt ctgctgccga accgaatccg   28800
tgataatccc gaagctgaaa ttccgtcgat ctacaactat gtaaagaaaa ccaagaaggc   28860
gaccatcaaa ccgggcgcgt tcctgtttga cagcgacgtt tatggttatc tcgcggccaa   28920
caaaatgtcg ttcgatcaac tgattggcga agataccgac tacaaggcaa tggccaaggc   28980
cgaaactgat gttgagaagg ccaaggaata tgcacgcctt caccgttgga caagttacgc   29040
gaagcccgtt cgcgctaact tggacgaatg cttcgccgct ttgacggcct aagtgcaccg   29100
gagtgccagt gatggattct aggaaaccga gagaagaagt attaattgag tggttcctgg   29160
gcgactcgaa agagatcctg gccgatctcc agggcgcggt cgcggcggcc cgtgaggtcc   29220
accagtcgat gcaggaggcc ggcgcaagcc tggcctccac ggtcgaagac gcacgcgccg   29280
agctggtgac ggccaatcgg gagctgaccg ccgcgattcg ggaaaccgag gcacggcatg   29340
acaaggccct ggagaagctg gaccgccagg ccaagagcct gttggccgcg acccagcggc   29400
ggacggtatg ggtggcggcg atctgcgccg gcattgccgg cctggccgga ggcctgggcg   29460
gtgccctgct cttctaccgc ttggttgccg gctagcgccg ggttgtgaca cacgctgagg   29520
ccgcgcaagg cggcctcgcc gtttgtggga gtcgccgcag gcgctcccgt gcggcaagcg   29580
gagcgcgcag cgcctgggaa ccgggcgcgg aggcgagagg gatggaagcc cgaagggggcg   29640 agacgcggcg tagccgtggc tcgatgcgca gcacgacagc ccgcgccgaa ggcctcgccc   29700
tggattgcgc aatccacttc tattaaactg gattgcacaa tccacaagac aggatcgtca   29760
ccatgtcgct actgccgact catgaggtct atgccgagct gcaactggcg tatgaacact   29820
tcaacgtcca gctgttcgac ggccagctac cggactgcct tatcaccctc cagcgtgaac   29880
```

```
gccgaaccta cggctacttc tcgcgcaagc gcttcgcccg tcgtagcggt gaaatgaccg   29940
atgaaatcgc catgaacccc ggctacttcg cgattcgctc attgcgcaaa acgctgtcgg   30000
tgctggccca tgaaatggtg cacctgtggc agttccactt tggcgcgcct ggccggcgtg   30060
gctaccacaa caaggaatgg gccgcccgca tggaagccct gggcctgatg cccagcaata   30120
ccggcgcacc tggtggcaag cgcctgggcg aacaaatgga tcactacatc atcccaggcg   30180
ggcgctttga cgtgagctgc gcggagctgc tgacgcggga cttctcgctg tcgtggtacg   30240
accgtttccc cccggaacga ccgcaaattg acccgccgac cggctcgaac ggtcgcgggt   30300
ttgtcgatga cgtagacggt gaggacgaag gccaggggca agctctggat cagggcggcg   30360
atgaactggg gccgctcggt gagctggtcg agctgccgcc cgaggtgccg ccgaaccggt   30420
caaaccgggt caagtaccgg tgcccgaagt gcgcaacgca ggtgtggggc aagcctgaac   30480
tggcgattct ttgcggcggc gaacactgcg ccgggtcgcc attccagccg gtcgcacgat   30540
gacaaagccc gcgaaagcgg gccttttgga ttgcgcaatc cacatcctca acggtggcca   30600
ggtcctgcgc cctggcctcg atctccggct tcccagcatg cggcggcctt gcgcagcaag   30660
ccggcgctat cgcggtgcgc cagttcgccc ggtttggtga tgaacgtcgc ggcggcctcg   30720
tagaactctg cggccacttc ccaatcgtgt tgcagctcgg ccttgcgcgc agcggcggca   30780
agcgcctggc atgtcctggc ggccttggtc ggcgtggtct ggtgtccgta catatcctgt   30840
tctccagcgg ggagcgccgg ggcgaagccg cggcgctcgg ttgggtagtg gggttaggcc   30900
cgtttaacag cccgtgcgag ggtcagaagg tcggcggact ccattaactg gtcgcgctcg   30960
gccagttgct gcatggacgg caccgggcga gctggggccg ctgcgcggcg cgcagaagcg   31020
gccaggcggg ccaggaagac acggaacgag ggaagggctt gagtagccat aggtaactcc   31080
ttttttcgca gaggaaggcc cggagcggtt gccgccgctg gtatccgggc caggattggt   31140
ttacttggtc aggcgctcgc tgcgcacaaa gccttcgcac atgtcacgga agatcgtggc   31200
gtgcagttcc agcgggaact cggcgatcac ctcgcggcga ccgatgccgc cacgctgggc   31260
aacgatcatg tacatggtga cgttggctgg ggtctggttc gggcgagcct gatgggacac   31320
ttcaacggtg aagccgctga actcgcgcag ggcctcggct tcgctgaaat acaggatgtg   31380
ggtttcgata gtcatgggtt gaatctcctt tcgcagattg ccccggagcg gttgccgccg   31440
ctggtgtccg ggggtgtcga ggcggtattg cttcgacgtg gttagtatct caaaaagcgg   31500
ccctcacgtc aactattcgt caaacaatat ttgacctaaa gtttactgga attccaccga   31560
tcacagggca aaaaaaagcc ccggacgtgt ccagggcggg gaaggcagtc gcgtcactgc   31620
atcatccaag tgaagcggta cggatccatg aacggaatat cgtcgtcgaa gctgtcgaag   31680
tcggcggcgg gctgcgggga gggttgcggc ggctgttgct gcgctggtcg ccgttgggcc   31740
tgctgtggtc gctgtgcctg ctggcggggt gcctgctgct ggccttgatt gtacggatca   31800
ccgccttgct gttggttctg cggacgcccg cccagcagct gcatggtgcc ttgcatgtcc   31860
acgatgatct cggtggtgta acgcttgatg ccgtccttct cccattcgcg ggtctgcaac   31920
ttgccctcga tgtagcactg ggagcctttg cgcaggtact cgccggcaat tccgcgacc   31980 ttgccgaaca gcgaaacgcg gtgccactcg gtgcgctcga ccttctggcc gctctgcttg   32040
tctgtccact gttcgctagt ggccaagctc aggttggtaa cggcgttgcc gttgggcaga   32100
tagcggactt caggtcttg tccgcaagtg ccaacgagga tcactttgtt tacgccacgg   32160
gccatgatga gtctcctttc tcgcgaaagt gcccggtcta gaccgggcac gctgggttaa   32220
```

```
atgaatgcgt cgttgattgc ttcgatcagc aattgctttt cggtttcgct gtgcatgttg    32280
accagcatct cattgaacag gtccacccct ttccgcgaac ccagctcgtc gtcctcgatc    32340
acctccagct cgtaacggat caggtcgatg agatcggcca gaacaatgac cgcgcagacg    32400
ttaaacgggt gttggatcac tgcctgagaa tccatggttg ccgcctccgg tttgcgcatc    32460
cccttagcga acgaaaggaa gtcttctttc gtcaggaaat cgccgtcctc tagaaaggtg    32520
ctggtattca tttttttgtat ctccttcgca gattccccgg agcggttgcc gccgctggta    32580
tccggggtgt cgaggcggta ttgcttcgac gtggttagta tctcaaatcg gggcgctgtc    32640
gtcaactgtt ggtcaaacaa tctttgacga ataattgact tgacgcggcg cgcttttcgg    32700
agctgcttag atgccgaggt gggagcggga ggtaaacata aagcgcgccc gcgaagcgtg    32760 cgcagcccg cttttgccct ggagcgtgag tctcccccgg tggatctgct cgtcagcctt    32820
cggttggtcg cggtaagccc cgactacccg gagctgggcc gccgtcatgg ggaccgtgga    32880
atagcggagc gaccgaaggg agtgagcata tgccgcgaaa gccccttgac ggcataggcc    32940
cagcggaggg taggcgatta gggctgatag cggccagccg gagggtgatg agcacaccca    33000
ggacgcgcag gggcggcaag gtggccagca ggccgccgcg caggccggca ggccggaggg    33060
caagcggagc gcgcagcacc tggcgggcca ggtgcgcagg cgagagggat tgaagcccga    33120 agggggcgaga cgcggcgcag ccgtggctcg atgcgtagca cgaaagcccg ggccgcaggc    33180
ctcgcactag atcttctcgc tggccaggtg gtggaagtac caggccaatt cgggacgccc    33240
cccgcccatt tgttgcttga tggcagtcac cagatcctcg cgaacttggc cggtcgctgt    33300
ttccaggcgc tggcggatct catcaacctc ggcgctggcg acccattcaa ggcaagccag    33360
gtaatcgagc acgcccttttt cctctgttgg tgtaagcatc tgcaaatccc tcagcagtca    33420
aactgtccgt gacagaaagg cgccatctag gcctttttct gtcggttagg tgtcttcttt    33480
gtggtccctg gttgggcctc cttttggctgc tcatgcttgg cggccatctg cttgaccagc    33540
tcggcttcct cgggggtgag ccagaccatg acgggcacaa ggccgactgt ttggcgttcc    33600
agcacgcgcg ttacgcgctt gattgcagcg tgtacaagct gccgcgactg gccgatgttg    33660
ttggccacct cgataggttc cttgccctcc accagcaccg ccctggcaat gtccagggtt    33720
ttggtggaca tgccccggag cgcaggcagg gaaacggtcc attgttcggc ggtgtatttc    33780
ggctgggtgg gctgcattcg cggttcctta ctgttggcta aatgccctgc taccggcagg    33840
gctacgggtc aagcgtgcta ctggttcatt tgctcgatga agccccgcgc atgcgcttcc    33900
aggcggcggg cgtctgtggt gccggcatgg agccggtgcc gtttgacgcc ctgggcggtg    33960
gctttccaga tgacgtaaaa cgtcccctcg ttgttgcgct cgatagtaat ggcaacgccc    34020
tggtcactgg taccaacctt ggcggcgact gccgccacgg tttcgctttc cagtgtctgg    34080
cggtcccata ccagcagggg cacaaactgc gggtcgttga tcgcgtcggc tgtctccagg    34140
ccgcccgcat cgcacaacca cgcttcgtcg tcatcgtccc aggcttcggc ggtgatcgga    34200
aacgtccacg ccagaagtgg ccgaccgccc tgcacctggc aggcgtaaag ctggtcagag    34260
tcgagcagaa acgccacgca atccccaggg atgagcaggc catgcccagg gttggccttg    34320
agtaacgatc ggtaggcttc caacgtcgcgt tcgtaagtca tggtcggttc ctcgatctta    34380
ggccttggcc acgccaggg agtgggtagc gatgcggcgc atgatgagca ggtggggcag    34440
ggtggccagg cccgtcaagg tccagtagcc cccgccccac tgggcaaaaa tggtcgtcat    34500
gttgccgtgg tccaggtcgg ccagcttgaa cgacgcgccc agctcgtcgg cgtggtagtc    34560
gatgacgggc cgctgcgaaa ggttgaactc gaaacgggcg cggtcgtgc gtgccggtgg    34620
```

```
cgtgccatag gcgcgttctt gatcgatcaa aaacgcctct tcgtcgccca ggatggcgcc   34680
ggggtaacgc acgcgcagct cgggcagcat caggccggaa tgctgggcca tccacatgtt   34740
tggcccgatc tggcgggcat agtcgatgat cgcggtatgg ccaggacat agaagacttt    34800 gcacatggtt cgatcctcca agggcggggg aaagccgggc gttaaacgcc cggctcgcca   34860
gttacgcggg ggcttggccg ctgcgcaggg cctgggccag tacccacaag gcgcgattga   34920
gtttcacgtc ttggtcaatg ccgttaacgg cgcgggtagt tgtccggcgt ccttgcttgt   34980
tgcggccacg caagccgccc ttgatggtgt tttcctgcac gcggttgaac gtggtccaga   35040
gatcgcttgc gcggtcttcg gcacggcgtg gcatcagcag ttgcgacggc gtgaccgggg   35100
cagggccttc ggatgggtcg tagcggtagg ccagggccgc catggcgaac gcttcttgct   35160
cttcctggcg caagtggtag tgctgcatgt cgtcaaggtt ggcgtcgatc tgctcgaact   35220
ggcccagcac ctcataggca ccttcgataa cgtcgttaac aacgtcaatg cggccgctgt   35280
ggcgcacttt ctgatccatc gccatgtcgc ccaggaccag cccgttagcg cacacgaaac   35340
ggaacttgcc ggccatcatc tggtagctgc tgctgccgtc gtggctgttc agcagaatga   35400
tttcgttcgc ttccttgctc atgatgttgc tggcatggcg caggcgaatc atgtgcttgg   35460
tgtgctcgcg tttgtcggtg ttgcggacgc gggtctggca cgccatgaac ggctgaaaac   35520
cttctgtgcg cagcgcatcg agcaccttga cggttggaat gtacaggtaa cgttccgaac   35580
ggctgtcgtg cgcttcctcg gcaaagatcg agggcgccac gcgggcaatc tcgtcattgg   35640
tcagaggggc atcgctgcgg atcatgcacg gattacggaa gttgctggaa agacgcattt   35700
ttgtatctcc ttcgcagatt ccccggagcg gttgccgccg ctggtgtccg gggtgtcgag   35760
gcggtattgc ttcgacgtgg ttagtattca aatcggggcg ctgtcgtcaa ctgttggtcc   35820
aacaatcttt gacgaataat tgacttgacg cggcgcgctt ttcggagctg cttagatgcc   35880
gaggtgggag cgggaggtaa acataaagcg cgcccgcgaa gcgggtgcag cccgcttttt   35940
gccctggagc gtgagtctcc cccggtggat ctgctcgtca gccttcggtt ggtcgcggta   36000
agccccgact acccggagct gggccgccgt catgggggacc gtggaatagc ggagcgaccg   36060
aagggagtga gcatatgccg cgaaagcccc ttgacggcat aggcccagcg gagggtaggc   36120
gattagggct gatagcggcc agccggaggg tgatgagcac acccaggacg cgcaggggcg   36180
gcaaggtggc cagcaggccg ccgcgcaggc cggcaggccg gagggcaagc ggagcgcgca   36240
gcgcctggcg ggccaggtgc gcaggcgaga gggattgaag cccgaagggg cgagacgcgg   36300
cgtagctgtg gctcgatgcg tagcacgaaa gcccggggcg caggcctcgc gctatgcctc   36360
ggatgacggc agggcgatca ctcgccggca ccctgctcca gctccagcaa gcgcgctgtg   36420
gcggcctgct cgatcaacaa atacaggcgc tcaacctgct gttgttccag cgctttcaac   36480
aattccaggg cctccaccat gccctcggcg cgggcctggg aaatcaagca attcgccgcg   36540
ctggtggcgg tgttcacttc ggccaggcgc ctgcgcaata caacctgata gctcggcggc   36600
aggatcaggc caggcatcaa ctccggttcg tttcggatac cggcctccct cagttttcgc   36660
cgacgacctg gcgcacttcg gccataacct tgttccactc gtccaccgca tcaaacatcg   36720
cgccgaccgc tgccaaggcg tgctgttgct tggtgtaagt gcggttcatg tgctcgggca   36780
cgatcaccac ggtatccggg ttgccgtagt ccatgaagcc aacggtaacg ctgccatctt   36840
ccatatcgaa catccgcaca acatcgagca ggcggttata gcctttcgac tcccacacca   36900
gcaggtaacg cacagcatct tccttgctta caaccttgaa atcgtaatca ctggacatgt   36960
```

-continued

```
tcagttctcc gcttggtaga aggtttgcgc ccattggtgc gcttgtgcag gtaacgcagc    37020
acgcccaggg tcatgcgtgc gtcggctagg aacggtggg cgccatcctc cagcacgccg     37080
caagctcggc cggcctcgat cagtttgatc cagcgccact gccaagcccc atagcggccc    37140
tcaacccatt ccccatgcca ttcggcatac agcagcatgg cgcaggcggt ggccagtgca    37200
ggcgcgacaa gtccgtgccg ctggtgggtc tgcgacagca ggcgctcgtc aaaggaggcg    37260
ttgtaggcga cgaccgttcg gcccgagacg atagaagcgt attgctctgc gatctccggc    37320
caggccggcg cggtggccac catgtcattg gtgatgcgt gaatccctgt ggcctccgct     37380
ggaattggct gagtagggcg tatcagcgtg ttgagtaggg gcgtgccgct cgcgtcgagg    37440
atcgtgattt cgcacacctc gtcgccatca cccacgcccg ttgtttcagt gtccagcagc    37500
agacaatccc cctcgatcag cgcctgggca cgggcggcca cggccttccg ccgaagctgc    37560
gccgcgctcg gctcccattt ccagggcacg caatcggcgg gatcgtatac atcgtaggcc    37620
ccgcggcctt gccagacgct gccggcaggc cgggtgctat accccggcat tagtcggtgg    37680
cgtgccttga ggtcacggca gcaaagccag ccgttggcct ccgcttccgc tggggtgagg    37740
tgaatacgcg cccttgccat gccggggcct cctgtcagtt gtcgccagtg atgatcgtgt    37800
gacgggcctg ggaaacgtcc agcgtgccgg cgcgaccgtc tgcaaagcga acagccatgg    37860
tcgtttccgg gatgccggcg acagcgtgcg catcggcgcg caaccccttcc tcgctgcggt    37920
gggccagcag ctcgaaaagc acaaaggcgt cattggcggc gtccacgcta tcccgtgcca    37980
aggcttcgtt gaggctctgc ttgagccagt tcgaggcggt gggtcggcc agcgtggcag     38040
cgatgctatc ggcaaactgt gcggtaccgg atggctcgcg gttgctgctg acggcctggg    38100
cggcctcacg gtcaatagcg cgcaactgat cgcgggcggg ctggctaagc ccgctgtgga    38160
actcggcaag ctgggccagg ccggtgagct gccaccaggc tgaggtaaag ccgtcgctac    38220
gttcggggcc attgggcagg gtaagcgcac ctttcaactg agtgaggtgc agttgggcgc    38280
aatcaatgat ggcttgttcc agttcggtca tggcgtatca actcttggta atggcgggtt    38340
gggtccagtc ctcaaggact aggccaggaa cgcgagcaaa ttcgcgagtg ttgttcgtga    38400
ccagaacaca cccagcggcc agggcatggc cggctatcgc tgcatcgttg ttgccaatgg    38460
gcgtacccag gcgggcgagg gcggtgcgga tctgcgttgt ttgatctacg gcggcggcgt    38520
cccaggacag gatggcgtcc aggcgctgga tgaaggcatc gaccatcgct gcaaccttgg    38580
gcgatgcctt ggggttggcg gccccgaaac gcatttcgga gtaggtgatg gccgaaacga    38640
caatccggtg ctgattagtg actgcctgtt ccagcttggc cagcaccgcg tcgggcgct    38700
cgcgcatgat gaacgaacag atgttcgtat cgagcatgta cgtctttttg ctcatgtgaa    38760
gtcacccagg aaacggtctt cctcgatcac atccttcgc tcggtcagaa agtcaggatc      38820
tgcggccgcc acgtcgcgca acgatgccca ggaggggcgc acaggcgca ggatcagcgt      38880
ttcgccgtcg cggataatct ccagctcgga aacgccctgg tactccatat cccgagggat    38940
gcggatcgcc tggtttcggc tgttcatgaa aatggaaacg gtacgcatgg gaacctccta    39000
caagttgaaa cacgttgagg cggtgatggt gctgccgcgc tcgatgccca ggtttgcaag    39060
ctggccgcgt ggcaccctcga taatgccgag ggcgggccgc aatgatgaat gcttggcggt    39120
tgtgtgtggc tccagctctt gtacgctctg gataacccg tctgctccga tccaagccgc    39180
gtctaatggg gcagggtgt tcttcatcca cacaaatcgc actgccggcg tagtccagag     39240
aaacagcatg cctcgccctg gatctggcct accggcgagg ccctgcgcct gtgcggcttc    39300
ggtggtggcc acgggtaggt cgagtgtcgc gccattctgg aacgacaacc ggcaatcatc    39360
```

```
gctataagcc ggtgtggtga gcacggcccc cgaaagcaac gcaggtaagc agcggttgag    39420
catcggcaca tccttcaatc tctaaagaga atcgtagcat atgtcaagca tatgtcaact    39480
gagcaattga gcgttctgtg gtggtcgtta tactgcgggc atgcgatcct tcgcagagca    39540
ctagaagccc gttttgcatt gccgtgcagc gggcttcgcc atttatggcc cccatgtaat    39600
ccctccccaa atatccccaa atcgtcgtag agcatggtgc gcgtggctga ctagcgaggc    39660
ttgcccgagt ctgtccggtg cgagcggctg gccgctgccg gcaggcaaga aaaagcccgc    39720
atcgcgggct tggggaagtg ctgataccga tcaactcatt aagtcgggga tggttcgctt    39780
gtgggttact tgcccttctt agccaggcca agctgttttt ccagagcctc tacctgtcct    39840
tcggcgcgtg ctgcgcggtc cagggcctgg cgttcgttct tgcgtgcctc gatagcttct    39900
gagtcctttt cgttggccct ggtgacagcc cggtggatct cctgggcgct gtgctccttc    39960
tggtgtttca actccagctc ggcgcgttcc tccagagcat ggtatttagc ctgtagctcc    40020
cggtataggg ctgcggtttc ctccaggctg gcgatcttgg cgcgcagctc gttcagttct    40080
gcatccatgc tgtcagccag tgcaatagct tcctcggcct gctcgcggat ctgcgcggca    40140
ttctcttcga tcacccggcg tttcccgtcc agggcctggt cggcagcaac gcgggccaga    40200
ttccagatat cggcgccgaa gttctcaagc aactgggcca gggcagccgg tggtgggtcg    40260
atgagtggtt gggcctcttg ttgcttgcgg ttcttccact cgctcatggc ctcctgaatg    40320
gtcgtaaagc tgccgacgcc acccaggcgc ttgcgcacgt tggccagggt gggcttagtg    40380
ccgtcagcgt ccagttcgtc ggcggctttc cagatcattt ccttcgtgag tgccatgggc    40440
gtgctccgct gtatgttgta gcgtgtagta tctgtcattt tcagaagacg actgcacgga    40500
atatcaggag tcggctgcac tggtggattg cagcgcggtg tacagggccg tcttgctcac    40560
cttgagccgt gtagcggcct ctcggacatt aagcccgttg gcgatgtgct cccgcgctcg    40620
ctgcaacttg tcggcggtga caaccggctt tcgcccgccc ttcctcccac gagcggcggc    40680
ggcagtcaac ccgccttgg tgcgctcgcg gatcaagtcg cgctcgaact ggcccagcgc    40740
gccgaacacg tggaagatga accgcccgcc tggcgtggtg gtgtcgatgg cttccgtcag    40800
agaacggaag ccgacgcctc gcgcttccag cgcgcctatc gtttcgatta ggtgcggcat    40860
agagcgcccg agccgatcca gccgccagac ggccagcacg tcgccgtcgc gcaggtaggc    40920
cagcgcatca gccaagccgg ggcggtcggc cttggcccg gaagccgtgt cctcgaaaac    40980
gcgctcgcag cctgccttgc gtagcgcatc cgtctgcaag gcggtgtcct gttccgccgt    41040
cgatacccgc gcatagccga tcagtgccat ttgccgcctc tcttgtccgt cattccgtcc    41100
gcctatctta atgtccgaca acccgttgtg caataacttt gctggacagt gtccggcatg    41160
gccgactaat gatcgtttga cggacattga cggtaaggca tttttgcatt actatgtgaa    41220
gcatcaacct tgattgcgag ggcaaaccac catgaccaca ttgaccgtta ccgcacgggg    41280
acaagtgacg tttcggaagg acgtactgca acacctcggc atcaggccag gcgacaagat    41340
cgagctggac ttgttgccag acggtcgggg cgtgctcaag gcggcacggc ccgcagggac    41400
gatagccagc tttgtcggcc tgctcgcggg caagacgcag aaggttgcca ccatcgaaga    41460
aatcaacgag gcggcggcgc aaggctgggc aggtaagcaa tgaaggtcgc agtcgatacc    41520
aacgtccttg tgcgtgcggt tgtgcgtgac gatcccgcac aagcggacgt tgccgccgca    41580
gtcttgaccg acgccgagtt gatcgcggtc gcgctgccgt gcctatgcga atttgtttgg    41640
gtgctgctgc gtgtctacgg cttccagcaa gccgacgcgg ccagcgcgat ccgggcacta    41700
```

```
ctggccgccg cgaatgtgga agtgaaccgg cctgccgtgg aggctggctt gctggtgctc   41760
gacgcgggcg gagactttgc cgatggcgtc attgcctacg aaggcaactg gcttggcggg   41820
gaaaccttcg tttccttcga taagaaggcg gtggcacttc tcacggcgca agggcaatca   41880
acgcgccttt tgtgacggac atgagcatga acgaattccg ccgactggcc gcgaagatcg   41940
accaacacat gcagcagctt gccgcccagg gtgtcagcga ggcccatgcc atcatcaatc   42000
gcatgatggg gtacgggcct gacctgcaca ggatttgggt cggcacatcc gatcagcagc   42060
tcatggcgct gtcccgcgag ttcccagggt tctaccgcta cgcccgcatc atggaagagg   42120
catccgaagc cgagcgccgc aaggcttcgc ggccctatga cggcatggcc gagttctccg   42180
aacagcacaa gcaaatgggc gcgcaactgc tgaccacggc ggccacgctt gagcgtggct   42240
accaggcgtt tcgtgcgagc ggcagtctcc aagacttccg gcctcagctc gacgagctgg   42300
gccgcctgca tcggcaatgg ctgtccgacc tggaagcctt caaagactcg ctgcgcacgc   42360
agggcgcaga acccaaggtg ctggaatacg tgaacgaggc tttcggccgc ctggccgagc   42420
gcatcaagca gcttgccggt tgatcgccgg aattttcggc ggttccggct ttgtcgcgcc   42480
gtgcacaaga gttctgagca attccgatct ctcgcggcgc ttcgtgcata gaacttctga   42540
ccgttcccgg tcagaagttc tatgcacaca cggcggccag cccagtgaac tggtgcagtc   42600
gccttctgaa aacgacagta tcatacaaca tactacaaaa tacaatatag gctaacgcgg   42660
ccagttggcc ttgttggctc cgctccagcg cggcgggcga gccacctcac cagagcgcag   42720
cagcagatgg gaagggtgtc gggttggcca ggcgtgccgg ttcggtgtgc gccgtgccgg   42780
cgtcgaacgc tacccgtgag ttatccacaa gccaagccaa accaaggccg ttaaagattt   42840
aagttaaagg gttaatacgc gcgcgcgttg ttagcgtttt gcgaggcctt gatttacctg   42900
ggctggaggg tggttctggt ccccgaagtg acgaaattgg cggtccctgg agtgacgaac   42960
cctagtcccc gaagtgacga accgacggtc cctagagtga cgaatcgtgg tcgccgaagt   43020
ggtggagcgt ttgggcgcg atattcggtg cggtccctgg agtgacgaat gcgcagataa   43080 agccccgaa gggctgcgg tacagttcaa acatatatga atcaatagag aaaaaccctt   43140
acacatcagt ccattgcccc cttccggtcc ctggagtgac gaattgccat gactcatgca   43200
gcgggagcgc ccttggcctt gcgtggcttc ttgataccgt tgcgcgtggc tttgagcaag   43260
gccgctttgc cggcgtcgga cttgttgaag aacaacacgg cgtcttcgtc gggcaggtag   43320
gtcatgaagt agtcgagcaa gctgccggcc tcggccagct ccttgacctt agcgcgaaac   43380
ttcttttcgg cctgggcgct tccgaccttc ttttgcagca gagccaggcc aatcttccat   43440
tggccctgat cgccgcaatg tttccggcaa agctcataga tgcgtttggc aatgcgctg   43500 cgcagcccaa aatagtcgcc cggaatggtc aacacatcca tggccttcgc ggcgttaaac   43560
gtggtgtcga taccttatat ccgaatggcg cacatgcgt tcttggcgcc cctagtgatg   43620
atctccacgt catcgagcag gccaacccag cgacggctgc cgtcacggtc tttcgtcgac   43680
tcaaaggtgg cccgcatgcg agtaccggtg agtctgtcga aagccttgct aagcagctca   43740
tagccgcgct cgctggtact gctgcgcgtg aagctcaaaa gttcgtgagc ggtcgtctcg   43800
atagtcggtg atacggctat gccggcgttg atcgcagcca ctagcttcga tacgcaaaac   43860
agcacgatat ctttgtcatg ctgggtcgcc cgaccggcaa cgctgggagt gatctcgatt   43920
ttgttcccgt tgtgctcgta ggtgatctgc tggtatctc cgtcttccac ggcgtagatc   43980
gggtgctcca tcgtaggtcg ctcatctttg gggatcgccg gcaggccggt cgcgatccag   44040
aaatcgagct gcgtttcgag caccactact tgtttgcgtc ccgctgaggt cttcaccgct   44100
```

```
tcgcgccctg gtgccttgtc cttcggttgc ttggcctctt cgcgtttcag ccgctccgcc   44160
gcctgctggt aggtttcgcc tggtcgtgct tcagcctcga tgcgcttgcg ccacttgtcg   44220
atgttgattg cgtcctgccc gaccaagggg cctctggccg ctggccgacg tttcggtggt   44280
ggggtggtgg ccacgtcggg gtcgatatca acaactcat tggacgacat gctgggcctc    44340
cttgctcaga tacttgtaga tggttgttct gctgaccttg aacctggcgg ccacgtcgct   44400
cacggtcgtc aagggtcggc cagcagtat cttgatatcg cggatctcct tcgcgcctag    44460
cgttggcttt cgaccccctt tgcgtccccg tgcgcgggcg gcctccaggc cggccatggt   44520
tcgctcgcgg tttagttcgc gctcgtactc cgccagggtg gcgaagacgt tcaactgcat   44580
ccgcccgccc gccgtgctgg tgtcgatgtg ttcggtgagc gattcgaagc gaacctgcat   44640
ggtttccagt tgggccatga gctggagcag gtgggagaga cttcgaccga agcgggaaag   44700
ctgccatacg acaacggtgt cccctgggcg aagtgctttt agcatctgct ccagctcggg   44760
tcggttggcc ctggccccgc tgatctgttc ctcatatatc cgcgtgcaac cagcggcaat   44820
aagcgcgtcc cgctgtaggt ccaggttctg gtcctgctta ctggtccgcg catacccgat   44880
gcgcaagcca cccgtcagta tgtctagggt ggacgtgtct ttgctgctac gcatgcagtt   44940
cctccttgtc gggcttgcgg gttcctgttt gcgacacct aatgattaca ctgaaaagtt     45000
tacgggaaag tttacagttt tgtcccaaaa aaacgccct gggtgtcact ttcagaaggc    45060
gacagcacga aatatcaaaa gtcgaccgca cggtctttc tgacgttgga gtcgcctcag    45120
aaaacggaaa ataaagcacg ctaaggcgta gttccctcgg gctacaccgc gtccgcactg   45180
cgcggttctt tcttcccttg cagtgacgca atcagcgggc aggaaacgtt cccccttccgc  45240 gcatggcagg cgcacaccaa atcagacagc acggcctcca tgcgcgccag gtcagccatc   45300
ctctcgcgca cgtccttgag cttgtgctcg gccaggctgc tggcttcctc gcaatgggtg   45360
ccatcctcca gccgcagcag ctcggcgatc tcatccaggc tgaagcccaa ccgctgggct   45420
gatttcacga agcgcacccg cgttacatcc gtctcgccat agcggcgaat gctgccgtaa   45480
ggcttgtccg gttccgggag caagcccttg cgctgataga accggatggt ctccacattg   45540
accccggccg tcctggcgaa aacgccaatg gtcaggttct ccaaattgtt ttccatatcg   45600
cttgactccg tacataacta cggaagtaag cttaagctat ccaattcaga ttcgaaagga   45660
caaacgtatg tctgaacctc aaaacggggcg cggcgcgctc ttcactggcg ggctggccgc   45720
catcctcgcc tcggcttgct gcctcgggcc gctggttctg atcgcttgg ggttcagcgg    45780 cgcttggatc ggcaacttga cggtgttgga accctatcgc cccatcttta tcggcgtggc   45840
gctggtggcg ttgttcttcg cctggcgcg catctaccgg ccgtcagccg cctgcaaacc    45900
gggtgaggtt tgcgcgattc cccaagtgcg agctacttac aagctcattt tctggggcgt   45960
ggccgtgctg gttttggtcg cgctcggatt tccctacgtc gtgccatttt tctattgatc   46020
acaggagttc accatgaaaa agctgctttc cgcccttgcc ctcgctgccg ttgttgcccc   46080
cgtgtgggcc gccacccaga ccgttacgct gtccgtaccg ggcatgacct gctcggcctg   46140
tccgatcact gtcaagaagg cgatttccaa ggtcgatggc gtcagtaaag ttgacgtgac   46200
cttcgagacg cgcgaagcgg tggtcacctt cgatgatgcc aagaccagcg tgcagaaact   46260
gaccaaggct accgaggatg cgggctaccc atcatcagtc aagaactgat catgaaagac   46320
ccgaagacac tgctgcgggt cagcatcatt ggcacaaccc tcgtggcgct gtgttgcttc   46380 accctgttc tggtcatttt gctcggtgtg gtcggcttgt ccgcgctgac cggctatctg    46440
```

```
gactatgtgc tgctgcctgc gctggcgatt ttcatcggct tgaccatcta cgccatccaa    46500
cgaaaacgcc aagccgatgc ctgctgcacc ccgaaattca atggagtaaa aaaatgaccg    46560
aaatcaccgt gaatggcatg acctgcacat cctgcgccac ccatgtcaaa gatgctttgg    46620
aaaagattcc cggcgtgaat gccgctgtgg tgtcctatcc agaaagccgc gcgcaagtca    46680
tggcagacac cgccgtgagc cacaaccaac tgctggccgc catcgccgca ttgggttatc    46740
aaggctcgat ccgggttggt gatttcaaag atgaaccaaa aatccgtgat gcacttgagg    46800
gcgccggttt gcatatcgcc atcattggca cggcggggc cgcgatggcg gcggcgctga    46860
aggccgtcga gcaaggcgcg acggtcacgc tgatcgaacg cggcaccatc ggcggcacct    46920
gcgtcaatat cggctgtgtg ccgtccaaga tcatgatccg cgctgcccat attgcccatc    46980
tgcgccggga agtccgttc gacggcggta ttgcggcaac tgtgcctgcg attgaccgca    47040
gcaaactgct ggcccagcag caggcccgtg tcgatgaact gcggcacgcc aaatacgaag    47100
gcatcctgga cggcaatcca gccatcaccg ttttgcacgg tgaagcgcgt ttcaaggacg    47160
accagagcct ggtcgtccgt ttgaacgagg gtggcgagcg cgaggtaacg ttcgaccgct    47220
gcctggtcgc caccggtgcc agtccggccg tgccgccgat tccgggcctg aaagagtcac    47280
cctactggac ttccaccgaa gcgcttgtca gcgacaccat tcccgcacgc ctggccgtga    47340
tcggttcgtc ggtggtggcg ttggaactgg cgcaagcctt tgcccggctc ggcagccagg    47400
tcacgatcct ggcacgcagc accttgttct tccgggaaga cccggccatc ggcgaggccg    47460
tgacagccgc tttccgcgcc gagggcatcg aggtgctgga gcacacgcaa gccagccagg    47520
tcgcccatgt gaacggcgaa ttcgtgctga ccaccggaca cggtgaattg cgcgctgaca    47580
agttgctggt tgccaccggt cgggcaccga atacgcgcag cctcgcgctg gacgcggcgg    47640
gggtcactgt caatgcgcaa ggggccatcg ttatcgacca aggcatgcgc acgagcaacc    47700
cgaacatcta cgcggccggc gactgcaccg accagccgca gttcgtctac gtggcagcgg    47760
ccgccggcac ccgtgccgcg atcaacatga ccggcggcga cgcagccctc aatctgaccg    47820
cgatgccggc agtggtgttc accgaccgc aagtcgccac cgtgggctac agcgaggcgg    47880
aagcgcacca cgatggcatc gagaccgaca gtcgcacgct gacactcgac aacgttccgc    47940
gagcgcttgc caacttcgac acacgcggct tcatcaagct ggtcatcgag gaaggtagcg    48000
gacggctcat cggcgtgcag gcggtggccc cggaagcggg cgaactgatc cagacggcgg    48060
tgctcgccat ccgcaaccgc atgacggtgc aggaactggc cgaccagttg ttcccctacc    48120
tgacaatggt cgagggggttg aagcttgcgg cgcagacctt caacaaggac gtgaagcagc    48180
tttcctgctg cgctggataa aaaaggagg ttttcaatga gcgcctacac cgtgtcccgg    48240
ctggcccttg atgccggggt gagcgtgcat atcgtgcgcg actacctgct gcgcggattg    48300
ctgcgtccgg tggcgtgcac cccggcggc tatggcctgt tcgatgatgc cgccttgcaa    48360
cggctgtgct tcgtgcgggc ggccttcgag gcgggcatcg gcctggacgc gctggcgcgg    48420
ctgtgccggg cgctggatgc tgcggacggc gatgaagcgg ccgcgcagct tgccgttctg    48480
cgccagttcg tcgagcgtcg gcgcgaagcg ttggccgatc tggaggtgca gttggccacc    48540
atgccgaccg agccggcaca gcacgcggag agtctgccat gaacagcccc gagcgcttgc    48600
cgtccgagac gcacaaaccg atcaccggct acctgtgggg cgcgctggcc gtgctcacct    48660
gtccctgcca tttgccgatt ctcgccattg tgctggccgg cacgacggcc ggcgcgttca    48720
tcggagagta ctgggtatc gcagccctca cgctgaccgg tttgttcgtc ctgtctgtga    48780
cacgactgct gcgggccttc aaagatcgat catgagcgct tcccattgag acaaaccacg    48840
```

```
ctgtcgctac gttgcctcat gccggcatca aattcggctg agtagcttct cgccatctgg    48900
acgtagctca cccttgggtg aaacatgccg atacagggtc tgccgcgtga cgccaagttc    48960
ctggcacagg tcgccgacct tggtctctgg ctgacccatt gccgccatcg ccagccgcag    49020
cttggcggcg gtcatcttga acggccggcc gcctttccgc ccgcgcgcgc gggccgaggc    49080
taggccggca atcgtgcgct ccgcgatcaa ctcgcgctcg aactcggcca gggcggcgaa    49140
gatgccaaag accagcttgc cggcggcggt cgtggtgtcg atggccgcgc cgtgcccggt    49200
taataccttc aagccgatgc cgcgcccagt caggtcgtgc acggtgttga tgagatgtcg    49260
caggtcgcgt ccgagccgat ccagtttcca cacgaccagt gtgtcgccag ttcgcaacgc    49320
cttcaggcag ctcgtcaagc cgggccgatc ctcgcgcatg ccggatgcct ggtcctcgta    49380
aagatgtact ggatcgaccc cggcggcaat cagcgcgtcg cgctgcaaat cggtagcctg    49440
ggagccgtcc gccttcgata cccgcatgta gcctatcagc atgtcgtacc tgtcacatat    49500
acgttcgatt atgtgacagt gtgagccaga aagttctcgc cgtcaaaaac tgtcacttaa    49560
cccgtcattt agtctaagac ctgcaaacgg ccattcaggc tcgtaatgtg acaaaaactc    49620
cggcgggatg ccctccttgg tgaacgtggc gcgcaaacgt tccagggatt cggggtcgcg    49680
tcgcccgtag gacgccagtg tgaacagcaa gcgggccgtc tccgggttgt gtcgcgcttc    49740
aatgatggcc tcatcgatgg cctgggctgc tcgttgccag tggttgatgg gttccggctt    49800
cggcaccttc gccggcaggc cgttggtgaa accagtgtgc ggctccgtct gaaacagcgc    49860
ggcctgttcc ccgcgcggga tcagcgcctt tgactcgatc agcgtgatgg cggtggccgc    49920
cgcctccagc atctgccact gcaccgccgg ggccagaatc tcgtagggac gccacagact    49980
ctgcccggcg cgcagcggat ggccgcagcg ctcccagaca tggcggatgc tcgccgagca    50040
actgccgcag tgcgagagcg gcgtgttcag ctcatcaagc agggtgcgca gcagccggaa    50100
ccacaagccg gcgtggacac gccgacgcgg cagctccaca aaacccgtcg tcagcgcctg    50160
ccaggtgcgc cggtccatgc aggcgattgc gtcatcggca gggcgcggcg cagcatcggc    50220
gatttcccac tgaagatacc ggccgggcat gccccagtag gactccagcc agcagccatg    50280
ctgcgggcag ctcagcatca aggggagctg ccagacgagt agcacagctt gattcgttgg    50340
atcgttcaga cactgcggac acgcccggcg aatcgtctgg ctcggtagcc aggcacgcca    50400
gcgagtgatg gaccgcacct tgcgggtgcg cttgggcagg agcaccgcgc attggaatgt    50460 ataggttttcc aaggctgctg gtaccgaatc gtcgagactg tcgagcagcc acggcaccca    50520
gcctgcaaga ctcatgctgc gcaaccgctc cagctcgacg ccactgcgct ggcagagcgc    50580
cgtcagcaac gacaaggatg gtgcggtatc caggtcatca agttggctgt gaccaagatc    50640
gtgggccagc agctcgtgca cgtccatctg gtagcaggcg gcgacccggt tgagccatga    50700
ggacagggct tcgcttcttg gtgccggatg cagcggccag cgcggcgcgg acttcacatc    50760
agttcccgct cgaactgtcg ccgccgctca ctggggccga tgtagtcggc catgctgagc    50820
gtgcggtggt tgatcgcttc ctcgccactc tccacgcgcg cgacgccgc cgccaccagc    50880 agatgtgcaa gctcgccgat ggtgccttcg ctccgggtga gcaggtagcg ggccatgtcc    50940
agcgtggcaa tcgggatgg ccgccgtagc gggagtgacg ccgcgaagct ggccagcagc    51000
gagcagcagt cctcattggc ctcccacggc ggcagcagca tcggctcgaa gcggttttcc    51060
aactgatcgt ccgaacggat ggccaggtac gcctcgcgcg tgccgacccc gaccagggg    51120 atacgcagct cgttgccgag gaagcgcagc aggttgagga actcgcgccg gttaacgctg    51180
```

```
ttgccagcca gtacattgtg cagttcgtcg atcaccagca tgcgcacgcc gaccttgcgc    51240
agcagggcca gcgccagttg ctccatttcc ggcagccgtg ggcgcgggcg cagcggcgcg    51300
cccatcgcag ccagcagcgc gacatagaag cggatcaccg atggctctga cggcatctgc    51360
acgaccagca ccgggatatg ttcttggtca gcgtcggtgc cgaccgggtg cgcccgccgg    51420
aatttctcga cgatcatcga cttgccgttg ttggtggggc cgaccagcag caggtttggc    51480
atgcgttgct tgttcggcca cgcatacaga gtttccagcc ggttcagcgc ctcgaccgcg    51540
cgcgggtagc cgatccagcg gtcggcgcga atgcgctgga tgcgctcgtc tgccggcagc    51600
ctggccaaac cctgtgccgc tggcagcagg tgggacaggt caatgacggg atattcgtcc    51660
acggctacca ctcctcgatc tgatcgaacg gtttggccgg cggcaggttg tctgcctgcg    51720
ggtcagccat gtccacatcc ggcggtatgg gcttggccgg tggctccgac gtcttgaagt    51780
gctggcggcg atcagcgtcg cgccgcgcct tgcgcgtggc cttctgggcg gtggtcacga    51840
tctcgcgcat ctgcccgatc atgcggaaca gcgccgactc gtccacctgc tcgcgcccga    51900
gctgacgcaa tttggccagc gcctggcgtt gttcccagag ggtgacgcc ggatgggaca    51960 aggtgcggta gtggatctcc agatagtgct gaccttccgg ttccagtacc cagatgcggc    52020
tgatgtcgcg cggatcgcgc cggatcagga aggcgggcaa gcgctcgcgc cgggcaatcc    52080
acggcttgag ggcgtcggcg tagtagtgga tgtggtcgat gacaaagccg gtgcgggtca    52140
gggtgcggcg gatcaccggc aggaaatcga ccaaaaacgc ggtggggcgg gtaacgacgg    52200
ccgggacgcc aacgcgctcc acggcctcgg cccagcgcgc ggccggcggc tggagcaggc    52260
cgttgtgcac ggagccgtga taggtgccta ccgccaacgc gagccagcgc tccagctcgc    52320
gcagcgtcag ggtggccatc ttctcggaat cgtactcgcc gcgctggccg ggattggaga    52380
aggtcgtccc cggtaattcg tcgtggatca tctgcatcgc cgtgccgatg atccgttcca    52440
cgatgccgcc gtagtgcggc tggcctggtg ggcgatagtc cagccggatg ccatgctgtt    52500
cgcagccacg gcgcagcgct tcgcttttga actcggccgc gttgtccaga tagagcagcc    52560
tgggcttgcc gctcatcggc cagtccattt ccacattcag cccttccagc cagggccgct    52620
tgtcgcaggc ggcatgcgcg aggcataggc cgaccgagac ggcggacggc gcttccagcg    52680
tgaccaccat gccgagtacg cagcgcgtga acacgtcgat ggcgagggtc aaatatgggc    52740
ggccaatcgg ttgccggtcg cgctcgtcga ccacgatcag gtcgatgacg gtgtggtcga    52800
tctgcacctg ttccagcggc atggtgactt cgggcggaat gccacccgcg ccttgcaagg    52860
gacgggcagc gtcctgcccg ccccggctgc gggctatttt cgccgggtgt agtccggcaa    52920
tccgctgggc cacggtgttg cgcgccggca ccggcagctt ctgggttttg cacgcctgcg    52980
cgacttcgcg gtggaacgcc gccaggctgc gtttctgctt ggtcaggaag cgcttttgca    53040
gcagctcgcg gatgatgcgc tcgaccggtt ccggcaagcg ccccttgcct ttgccgccgc    53100
cggatcggcc gggcgtcagg tctgttacca ggccagtacc ctgccgggcg cgacggatca    53160
ggacatatac ctgtcgccgg acaggccca gcgcttgggc tgcctcatcg gcggcttcat    53220
gcccgaccac ctcaagcgct gccagtggcc cgatgatttc cgtccggtgc cgggcttgcg    53280
cccatgcctc gtcgggcagg gtggccacgc cttgcgcggc aatcggtgga gtgtctgatg    53340
tcatgcccaa acctcgcttt ggtgcacacg agtattgagc atagtcgaga ttggtgcaga    53400
cgactcctga tattgggctg tcaggagccg tatgcacacc aggcgttaca tccagtcaga    53460
tggtgcggtc gtcttctgaa aacgacacct gatgttcgtt aaagcggttt cataaaacgg    53520
tggttttatc gtactcccca gacagagcgc tggtttgcgg gcaggtactg ggcttaagtg    53580
```

```
cgtttactgt tccattgctc cccgaacccc aatactgtgt atttgcacag tattcatgcc   53640
agccaccgcc aaacccaagc gctacaaccc ccgccacccc gaacgcactc tgctctacca   53700
aaccgtggcc gagcactacg agagctggct ggagctggct tgcgagggtc aatttgaggg   53760
ccagggcgac caccacagcc ccaagcccta cgtgcgcaaa gcgttcgaga aatatctgga   53820
gtgcggcatc ttcgcccacg gctttgcccg cgcccgctgc gacgactgcg gacacgactt   53880
cctggtcgcc ttctcgtgca aaggcagggg tgtctgcccc tcatgcaaca cccggcgcat   53940
ggctgagacg gcggcacacc tcaccgacca tgtgtttccc cgcctgccgg tgcgccagtg   54000
ggtgctgtcg gtgcccaaac ggctgcggta ctacatgcag cgagagggcc cggtgctggg   54060
catggtgctg cgcatcttcc tacgcgtcat cgcgcaaacg ctgcaagcca acagccctgg   54120
tgcggccaat gtggacaagg cagcactgca cataggcgca gtcgccttca tccaccgctt   54180
tggctccagt ctgaacgagc atgtgcactt ccatgtctgc gcagtcgatg gcgtgtttga   54240
ggaagtggcg ggcgaggagg gcgatgctgc tgatgcagct tctcaaagct caccatcgcg   54300
catcatcttc caccccgcca ccggcgtgac tgcggatgcc gtgggtcagg tgcaggccag   54360
cttacgcaaa cgcatcctgc gcgcctttgt cggacggggc ctgctggaga gtttcgaggc   54420
ccaagagatg ctgggctaca agcacagcgg gttttcggcg gacaccagcg tgtgcatagc   54480
ggcgcacgac cgcgccgggc tggagcggct gctgcgctac tgcgcccgcc cgccgtttgc   54540
catggagcgg ctgcgcaaag cgggcagcga gctggtctac cgctgcgcca agcagcacag   54600
cgagcccggc agcctgcctc acaacaagcg cggcgtaaag gccgatgaga tcaccctcac   54660
cccgctggag ctgattgaac gtatcgccaa gctggtgccc ccgccgcgca cgcaccgcca   54720
ccgctacttt ggcgtgctgg caccgaactc acccttgagg cctgccgtca cggcgctggc   54780
gcgtgatgca gcggtgaaac cggcgcaggt gcaagccgag ccagccagca cggctgcagg   54840
cgagggcgca cttggggtaa gaagcccact gccaacccag accgagcccg cccagccggt   54900
gccacccaag cgcccggcgc actatttgtg ggcggtgctg atggcccgta tctacgaggt   54960
gttcccgctg ctgtgcccca tctgcggcgg gcaaatgcac atcatcgcct tcatcacaca   55020
cagtgccgat atccgccaaa tactggagca catcggggtg gagacggagc cgccgcacat   55080 cacccggca cgcgggccgc cactgtggga cgagtgcgac gcgcaagccg cagagggcgt   55140
ggagccagcc ccagactggg atgaagcgac ccaaccggcc ccggacttcg aggtcgatca   55200
gcgcgtcagt tggtag                                                  55216
```

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 24

```
gagtttgatc ctggctcag                                               19
```

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence:primer

```
<400> SEQUENCE: 25
taccttgtta cgactt                                                    16

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 26
gtgccagcag ymgcggt                                                   17
```

BACTERIAL PLASMID HAVING GENES ENCODING ENZYMES FOR THE DEGRADATION OF AROMATIC COMPOUNDS

This application claims the benefit of U.S Provisional Application No. 60/167,062 filed Nov. 23, 1999.

FIELD OF THE INVENTION

This invention is in the field of bacterial plasmids. More specifically, a bacterial plasmid has been isolated which contains genes necessary for plasmid maintenance and for degrading aromatic compounds to small aliphatic molecules.

BACKGROUND OF THE INVENTION

It is well known that bacterial genes are sometimes located on plasmids (Actis et al., *Front. Biosci.* 4:D43–62 (1999); del Solar et al., *Microbiol. Mol. Biol. Rev.* 62:434–464 (1998)). Plasmids are not necessary for routine "housekeeping" functions in bacteria (e.g., DNA synthesis and protein synthesis). However, the genes on plasmids are often important in specialized environments. Antibiotic resistance genes and heavy metal resistance genes are examples of genes commonly found on plasmids. Although plasmids are similar in function to chromosomes as carriers of genes, plasmids can be distinguished from chromosomes. Plasmids are smaller than chromosomes and encode functions that are dedicated to plasmid replication. Each type of plasmid has a distinct ori sequence and rep gene(s) for initiation of replication. These sequences constitute the minimum requirements for a functional, replicating plasmid. Fu et al. (*Mol Gen Genet* 250:699–704 (1996); Plasmid 38:141–147 (1997)) has reported RepA protein that has replication initiation and transcription repression function.

The genetic information for degradation of aromatic chemicals is also frequently located on plasmids in bacteria (Assinder and Williams, *Adv. Microb. Physiol.* 31:2–69 (1990)). The well-characterized TOL plasmid pWWO is typical of many bacterial plasmids that have genes for degradation of aromatic compounds (Assinder and Williams, *Adv. Microb. Physiol.* 31:2–69 (1990)). Plasmid pWWO is 117 kb in size, is transmissible, and belongs to the broad host range IncP-9 incompatibility group of plasmids. The pWWO xyl genes encode enzymes for metabolism of toluene, m-xylene, and p-xylene.

Understanding the make-up of bacterial plasmids derived form species known to participate in degradative reactions is key to the design of more effective degrading species. Because of their ease of transmission, bacterial plasmids are useful tools for moving degradative genes into hosts. Additionally, because they are so promiscuous, many plasmids carry genes that have been adapted for expression in hosts other than the species from which the plasmid has been isolated.

In spite of the utility of bacterial plasmids, few have been fully characterized. There remains a need therefor for bacterial plasmids comprising genes encoding degradative enzymes whose replication and stability functions are understood and may be manipulated for the broad spectrum expression of degradative genes. Applicants have met this need by the discovery and isolation of a plasmid, CT14 from a Pseudomonas sp. carrying genes necessary for replication and stability in a host as well as genes encoding enzymes for the degradation of various aromatic substrates including catechols and other intermediates in the toluene degradative pathway.

SUMMARY OF THE INVENTION

The present invention provides an isolated nucleic acid fragment encoding a bacterial aromatic ring opening enzyme selected from the group consisting of: (a) an isolated nucleic acid fragment encoding all or a substantial portion of the amino acid sequence selected from the group consisting of SEQ ID NO:2, SEQ ID NO:4, SEQ ID NO:6, and SEQ ID NO:10; (b) an isolated nucleic acid fragment that is substantially similar to an isolated nucleic acid fragment encoding all or a substantial portion of the amino acid sequence selected from the group consisting of SEQ ID NO:2, SEQ ID NO:4, SEQ ID NO:6, and SEQ ID NO:10; (c) an isolated nucleic acid molecule that hybridizes with (a) under the following hybridization conditions: 0.1×SSC, 0.1% SDS, 65° C. and washed with 2×SSC, 0.1% SDS followed by 0.1×SSC, 0.1% SDS; and (d) an isolated nucleic acid fragment that is complementary to (a), (b) or (c). Preferred nucleic acid fragments are those that have about 90% identity to the nucleic acid fragment selected from the group consisting of SEQ ID NO:1, SEQ ID NO:3, SEQ ID NO:5, and SEQ ID NO:9. The present invention additionally provides polypeptides encoded by the isolated nucleic acid fragment of the bacterial aromatic ring opening genes.

The invention also provides a method of obtaining a nucleic acid fragment encoding all or a substantial portion of a bacterial aromatic ring opening enzyme comprising: (a) probing a genomic library with the nucleic acid fragment encoding a bacterial aromatic ring opening enzyme; (b) identifying a DNA clone that hybridizes with the nucleic acid fragment encoding a bacterial aromatic ring opening enzyme under the following conditions; 0.1×SSC, 0.1% SDS, 65° C. and washed with 2×SSC, 0.1% SDS followed by 0.1×SSC, 0.1% SDS; and (c) optionally sequencing the genomic fragment that comprises the clone identified in step (b), wherein the sequenced genomic fragment encodes all or substantially all of an amino acid sequence encoding a bacterial aromatic ring opening enzyme.

Alternatively the present invention provides a method of obtaining a nucleic acid fragment encoding all or a substantial portion a bacterial aromatic ring opening enzyme comprising: (a) synthesizing at least one oligonucleotide primer corresponding to a portion of the sequence selected from the group consisting of SEQ ID NO:1, SEQ ID NO:3, SEQ ID NO:5, and SEQ ID NO:7; and (b) amplifying an insert present in a cloning vector using the oligonucleotide primer of step (a); wherein the amplified insert encodes a portion of an amino acid sequence encoding a bacterial aromatic ring opening enzyme.

The present invention additionally provides an isolated nucleic acid fragment encoding a bacterial glutathione-S transferase selected from the group consisting of: (a) an isolated nucleic acid fragment encoding all or a substantial portion of the amino acid sequence set forth in SEQ ID NO:8; (b) an isolated nucleic acid fragment that is substantially similar to an isolated nucleic acid fragment encoding all or a substantial portion of the amino acid sequence set forth SEQ ID NO:8; (c) an isolated nucleic acid molecule that hybridizes with (a) under the following hybridization conditions: 0.1×SSC, 0.1% SDS, 65° C. and washed with 2×SSC, 0.1% SDS followed by 0.1×SSC, 0.1% SDS; (d) an isolated nucleic acid fragment having at least 69% identity with the amino acid as set forth in SEQ ID NO:8; and (e) an isolated nucleic acid fragment that is complementary to (a), (b), (c) or (d). The invention additionally provides methods for the obtaining nucleic acid fragment encoding all or a substantial portion of a bacterial glutathione-S transferase protein by method of hybridization or primer directed amplification. Additionally, the present invention provides polypeptides encoded by the isolated nucleic acid fragment of the GST genes.

In similar fashion the invention provides an isolated nucleic acid fragment encoding a bacterial plasmid maintenance protein selected from the group consisting of: (a) an isolated nucleic acid fragment encoding all or a substantial portion of the amino acid sequence selected from the group consisting of SEQ ID NO:12, SEQ ID NO:14, SEQ ID NO:16, SEQ ID NO:18, SEQ ID NO:20 and SEQ ID NO:22; (b) an isolated nucleic acid fragment that is substantially similar to an isolated nucleic acid fragment encoding all or a substantial portion of the amino acid sequence selected from the group consisting of SEQ ID NO:12, SEQ ID NO:14, SEQ ID NO:16, SEQ ID NO:18, SEQ ID NO:20 and SEQ ID NO:22; (c) an isolated nucleic acid molecule that hybridizes with (a) under the following hybridization conditions: 0.1×SSC, 0.1% SDS, 65° C. and washed with 2×SSC, 0.1% SDS followed by 0.1×SSC, 0.1% SDS; and (d) an isolated nucleic acid fragment that is complementary to (a), (b) or (c). Preferred nucleic acids encoding a bacterial plasmid conjugation protein are those having 90% identity to the nucleic acid fragment selected from the group consisting of SEQ ID NO:11, SEQ ID NO:13, SEQ ID NO:15, SEQ ID NO:17, SEQ ID NO:19, and SEQ ID NO:21. Methods for obtaining a nucleic acid fragment encoding all or a substantial portion of a bacterial plasmid maintenance protein are also provided employing nucleic acid hybridization or primer directed amplification. The present invention additionally provides polypeptides encoded by the isolated nucleic acid fragment of the bacterial plasmid maintenance proteins.

The present invention additionally provides chimeric genes comprising suitable regulatory sequences operably linked to the instant sequences. The chimeric genes may be used of transform suitable host cells including bacteria, yeast, and filamentous fungi.

The invention further provides a method for the degradation of a catechol substrate comprising contacting a transformed host cell under suitable growth conditions with an effective amount of catechol substrate whereby the catechol substrate is degraded, said transformed host cell comprising a nucleic acid fragment encoding a bacterial catechol dioxygenase as set forth in SEQ ID NO:4 under the control of suitable regulatory sequences.

Additionally the invention provides a method for the degradation of a semialdehyde substrate comprising contacting a transformed host cell under suitable growth conditions with an effective amount of catechol substrate whereby the semialdehyde substrate is degraded, said transformed host cell comprising a nucleic acid fragment encoding a dehydrogenase as set forth in SEQ ID NO:6 under the control of suitable regulatory sequences.

In similar fashion the invention provides a method for the degradation of a substrate selected from the group consisting of 2-hydroxypent-2,4-dienoate, methyl-2-hydroxymuconic-semialdehyde and chloro-2-hydroxymuconic-semialdehyde comprising contacting a transformed host cell under suitable growth conditions with an effective amount of said substrate whereby the substrate is degraded, said transformed host cell comprising a nucleic acid fragment encoding a dehydrogenase as set forth in SEQ ID NO:10 under the control of suitable regulatory sequences.

The invention further provides the bacterial strain CT14 comprising the plasmid pCT14. The bacterial strain CT14 is useful in a method for the degradation of aromatic compounds comprising contacting the strain with an aromatic compound under suitable growth conditions wherein the aromatic compounds is degraded. Similarly CT14 is useful in a method of reducing the level of mercury in a mercury contaminated environment comprising a cell containing the plasmid pCT14 under suitable growth conditions whereby the level of mercury in the contaminate environment is reduced.

BRIEF DESCRIPTION OF THE DRAWINGS, SEQUENCE DESCRIPTIONS

FIG. 1 describes a method for shearing DNA with modified Aeromist Treatment set.

Figure 1:
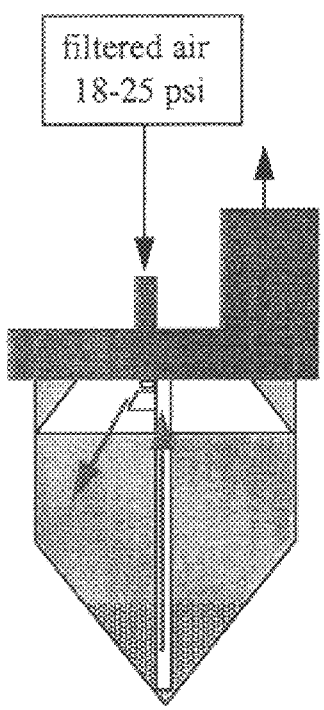

The invention can be more fully understood from the following detailed description and the accompanying sequence descriptions which form a part of this application.

Applicant(s) have provided 26 sequences in conformity with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of ORF 1 encoding a ferredoxin protein.

SEQ ID NO:2 is the deduced amino acid sequence of the ferredoxin protein encoded by ORF 1.

SEQ ID NO:3 is the nucleotide sequence of ORF 2 encoding a dioxygenase protein.

SEQ ID NO:4 is the deduced amino acid sequence of the dioxygenase protein encoded by ORF 2.

SEQ ID NO:5 is the nucleotide sequence of ORF 4 encoding a dehydrogenase protein.

SEQ ID NO:6 is the deduced amino acid sequence of the dehydrogenase protein encoded by ORF 4.

SEQ ID NO:7 is the nucleotide sequence of ORF 5 encoding a glutathione-S transferase protein.

SEQ ID NO:8 is the deduced amino acid sequence of the glutathione-S transferase protein encoded by ORF 5.

SEQ ID NO:9 is the nucleotide sequence of ORF 7 encoding a hydratase protein.

SEQ ID NO:10 is the deduced amino acid sequence of the hydratase protein encoded by ORF 7.

SEQ ID NO:11 is the nucleotide sequence of ORF 23 encoding a traI protein for plasmid site specific recombination.

SEQ ID NO:12 is the deduced amino acid sequence of the traI protein encoded by ORF 23.

SEQ ID NO:13 is the nucleotide sequence of ORF 24 encoding the traJ protein for plasmid site specific recombination.

SEQ ID NO:14 is the deduced amino acid sequence of the traJ protein encoded by ORF 24.

SEQ ID NO:15 is the nucleotide sequence of ORF 25 encoding a traK protein for plasmid site specific recombination.

SEQ ID NO:16 is the deduced amino acid sequence of the traK protein encoded by ORF 25.

SEQ ID NO:17 is the nucleotide sequence of ORF 33 encoding a vagD protein.

SEQ ID NO:18 is the deduced amino acid sequence of the vagD protein encoded by ORF 33.

SEQ ID NO:19 is the nucleotide sequence of ORF 34 encoding the vagC protein.

SEQ ID NO:20 is the deduced amino acid sequence of the vagC protein encoded by QRF 34.

SEQ ID NO:21 is the nucleotide sequence of ORF 38 encoding a rep protein for control of plasmid replication.

SEQ ID NO:22 is the deduced amino acid sequence of the rep protein encoded by ORF 38.

SEQ ID NO:23 is the complete sequence of the CT14 plasmid.

SEQ ID NOs:24–26 correspond to primers used in the isolation of the instant ORF's.

DETAILED DESCRIPTION OF THE INVENTION

The present invention provides nucleotide sequences of genes from a bacterial plasmid and the nucleotide sequence of the plasmid. The bacterial plasmid is designated pCT14 and was isolated from a wastewater bacterial Pseudomonas strain designated CT14. Plasmid pCT14 comprises a set of contiguous genes and regulatory sequences that encode and control several functions including, but not limited to, plasmid replication, partitioning of replicated plasmids to daughter cells during cell division, degradation of aromatic compounds, transposition of insertion sequences and transposons, and resistance to mercury. The functions of pCT14 nucleotide sequences and gene products have been deduced by comparing pCT14 sequences to nucleotide sequences and protein sequences in databases such as GenBank. Some genes included in the pCT14 set of genes, and the protein sequences encoded by those nucleotide sequences have recognizable sequence motifs but have only low homology to any sequence known in the prior art. These specific nucleotide sequences, genes, and gene products comprise unique or novel nucleotide segments, genes and/or gene products.

One group of unique nucleotide sequences, genes, and gene products in this invention includes those that are necessary for replication (orf 38:rep). The ORFs 33 and 34 (vagC and vagD, respectively) encode proteins that contribute to plasmid stability by ensuring that plasmid copies segregate to daughter cells during cell division.

Another group of unique nucleotide sequences, genes, and gene products in this invention include those that are involved in aromatic ring cleavage and degradation of the ring cleavage product to aliphatic compounds (ORFs 1–4, and ORF 7). ORF 1 encodes a chloroplast-type ferredoxin. It is likely that this protein reactivates catechol 2,3-dioxygenase that has been damaged by reactive forms of oxygen (Hugo et al. *J Biol Chem* 273:9622–9629 (1998)). ORF 2 encodes catechol 2,3-dioxygenase. Catechol 2,3-dioxygenase acts upon catechol and/or substituted catechols to form hydroxymuconic semialdehyde or a substituted hydroxymuconic semialdehyde. ORF 4 encodes 2-hydroxymuconic semialdehyde dehydrogenase. 2-Hydroxymuconic semialdehyde dehydrogenase acts upon 2-hydroxymuconic semialdehyde to form 4-oxalocrotonate (enol) ORF 7 encodes 2-hydroxypenta-2,4-dienoate hydratase. 2-Hydroxypenta-2,4-dienoate hydratase acts upon 2-hydroxypenta-2,4-dienoate to form 4-hydroxy-2-oxovalerate.

Other gene sequences in this invention include ORF 5 and ORFs 23–25. ORF 5 encodes a glutathione-S-transferase. ORFs 23–25 encode proteins that are involved in DNA transfer during conjugation.

In this disclosure, a number of terms and abbreviations are used. The following definitions are provided.

"Open reading frame" is abbreviated ORF.

"Polymerase chain reaction" is abbreviated PCR.

The term "bacterial aromatic ring opening enzyme", or "ring cleavage pathway enzyme" refers to an enzyme or set of enzymes acting either singly or in concert to degrade aromatic compounds to small aliphatic molecules. Bacterial aromatic ring opening enzymes of the present invention are particularly useful for the degradation of catechols and catechol degradation intermediates.

As used herein the term "bacterial ferredoxin" or "bacterial ferredoxin protein" refers to an enzyme capable of reactivating other bacterial aromatic ring opening enzymes. The bacterial ferredoxin of the present invention, encoded by ORF 1 (SEQ ID NOs:1 and 2), is particularly suitable for the reactivation of the catechol dioxygenase enzyme encoded by ORF 2 (SEQ ID NOs:3 and 4).

The term "bacterial catechol dioxygenase" refers to a bacterial aromatic ring opening enzyme capable of the bioconversion of a catechol substrate to the corresponding hydroxy-semialdehyde. "Catechol substrates" of the present invention are those substrates that are acted upon by a bacterial catechol dioxygenase and include catechols, methyl catechols, halogen substituted catechols and compounds such as protocatechuate.

The term "bacterial dehydrogenase" or "bacterial hydroxymuconic semialdehyde dehydrogenase" refers to a bacterial aromatic ring opening enzyme capable of the bioconversion of a semialdehyde substrate such as 2-hydroxymuconic semialdehyde to 4-oxalocrotonate (enol). The bacterial dehydrogenase of the present invention is encoded by ORF 4 (SEQ ID NOs:5 and 6). "Semialdehyde substrates" are any substrates that are acted upon by a bacterial dehydrogenase and include for example 2-hydroxymuconic-semialdehyde, methyl-2-hydroxymuconic-semialdehyde and chloro-2-hydroxymuconic-semialdehyde.

There term "bacterial hydratase" or "2-oxopent-4-enoate hydratase" refers to an enzyme capable of the bio conversion of dienoates such as 2-hydroxypent-2,4-dienoate to the corresponding valerates. The bacterial dehydratase of the present invention is encoded by ORF 7 (SEQ ID NOs:9 and 10), and typically act on substrates such as 2-hydroxypent-2,4-dienoate, methyl-2-hydroxymuconic-semialdehyde and chloro-2-hydroxymuconic-semialdehyde.

The term "bacterial of glutathione-S-transferase" or "bacterial GST" refers to a gene of the family of glutathione-S-transferases involved in catalyzing the conjugation of glutathione, homoglutathione and other glutathione-like analog via sulfhydryl group, to a large range of hydrophobic and electrophilic compounds. The bacterial GST of the present invention is encoded by ORF 5 (SEQ ID NOs:7 and 8).

The term "pCT14" refers to a 54 kb bacterial plasmid comprising genes for plasmid maintenance and encoding enzymes involved in aromatic ring opening reactions.

There term "CT14" refers to a wastewater strain of Pseudomonas comprising the bacterial plasmid pCT14.

The term "bacterial plasmid maintenance protein" refers to a variety of proteins necessary for the replication, conjugation and stability of the present bacterial plasmid. For example the rep gene encodes a plasmid origin of replication useful for the replication of the CT14 plasmid. The traI, traJ and traK genes are members of a family of genes involved in plasmid conjugation. These genes are responsible for encoding the corresponding TRA proteins which are referred to herein as "bacterial plasmid conjugation proteins". Similarly the vagD and vagC genes belong to a family of genes known to be involved in maintaining the stability of the plasmid in the bacterial host. These genes encode the corresponding VAG proteins which are referred to herein as "bacterial plasmid stabilization proteins".

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences.

For example, it is well known in the art that alterations in a gene which result in the production of a chemically equivalent amino acid at a given site, but do not effect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product.

In many cases, nucleotide changes which result in alteration of the N-terminal and C-terminal portions of the protein molecule would also not be expected to alter the activity of the protein. The skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Most preferred are nucleic acid fragments that are at least 95% identical to the DNA sequence of the nucleic acid fragments reported herein.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to divergence in the genetic code permitting variation of the nucleotide sequence without affecting the amino acid sequence of an encoded polypeptide. Accordingly, the instant invention relates to any nucleic acid fragment that encodes all or a substantial portion of the amino acid sequence encoding the instant bacterial polypeptides as set forth in SEQ ID NOs:2, 4, 6, 8, 10, 12, 14, 16, 18, 20 and 22. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental and physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res., [Proc. Int. Symp.]* (1994), Meeting Date 1992, 111–20. Editor(s): Suhai, Sandor. Publisher: Plenum, New York, N.Y.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual,* Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions,* Cold Spring Harbor Laboratory Cold Press Spring Harbor, N.Y. (1 984); and by Ausubel, F. M. et al., *Current Protocols in Molecular Biology,* published by Greene Publishing Assoc. and Wiley-Interscience (1987).

Identification of Homologs

A variety of nucleotide sequences have been identified from the sequence of the pCT14 plasmid. These sequences encode enzymes responsible for a number of aromatic ring opening reactions and well as proteins involved in the replication, stabilization and maintenance of the plasmid. ORF 1 for example encodes a ferredoxin enzyme responsible for the reactivation of the dioxygenase enzyme encoded by ORF 2. Similarly ORF 4 encodes a dehydrogenase which performs a ring opening reaction on aromatic semialdehydes. ORF 7 encodes a hydratase useful in the degradation of dienoates, intermediates in the catechol degradation pathway.

Comparison of the sequences of these nucleic acids and there deduced amino acid sequences to public databases reveals that the most similar known sequences range from as distant as about 35% identical at the amino acid level (ORF 7, hydratase) to about 70% identical (ORF 2, dioxygenase). Accordingly preferred polypeptides of the instant invention are those active proteins which are at least 80% identical to the amino acid sequence of reported herein. More preferred amino acid fragments are at least 90% identical to the sequences herein. Most preferred are nucleic acid fragments that are at least 95% identical to the amino acid fragments reported herein. Similarly, preferred nucleic acid sequences corresponding to the instant ORF's are those encoding active proteins and which are at least 80% identical to the nucleic acid sequences of reported herein. More preferred nucleic acid fragments are at least 90% identical to the sequences herein. Most preferred are nucleic acid fragments that are at least 95% identical to the nucleic acid fragments reported herein.

The nucleic acid fragments of the instant invention may be used to isolate genes encoding homologous proteins from the same or other microbial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction (PCR), Mullis et al., U.S. Pat. No. 4,683,202), ligase chain reaction (LCR), Tabor, S. et al., *Proc. Acad. Sci.* USA 82, 1074, (1985)) or strand displacement amplification (SDA, Walker, et al., *Proc. Natl. Acad. Sci. U.S.A.,* 89, 392, (1992)).

For example, genes encoding similar proteins or polypetides to those of the instant invention could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

Generally, two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes. Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)). Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach,* K. E. Davis Ed., (1986) pp. 33–50 IRL Press, Herndon, Va.); Rychlik, W. (1993) In White, B. A. (ed.), *Methods in Molecular Biology,* Vol. 15, pages 31–39, PCR Protocols: Current Methods and Applications. Humania Press, Inc., Totowa, N.J.)

As such it is within the scope of the present invention to provide a method for obtaining a nucleic acid fragment encoding all or a substantial portion a bacterial aromatic ring opening enzyme comprising: (a) synthesizing at least one oligonucleotide primer corresponding to a portion of the sequence of any one of the ORF's encoding bacterial aromatic ring opening enzymes; and (b) amplifying an insert present in a cloning vector using the oligonucleotide primer of step (a); wherein the amplified insert encodes a portion of an amino acid sequence encoding a bacterial aromatic ring opening enzyme.

Alternatively the instant sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature [Van Ness and Chen (1991) *Nucl. Acids Res.* 19:5143–5151]. Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Accordingly it is within the context of the present invention to provide a method for obtaining a nucleic acid fragment encoding all or a substantial portion of a bacterial aromatic ring opening enzyme comprising: (a) probing a genomic library with the nucleic acid fragment encoding a bacterial aromatic ring opening enzyme; (b) identifying a DNA clone that hybridizes with the nucleic acid fragment under the following conditions; 0.1×SSC, 0.1% SDS, 65° C. and washed with 2×SSC, 0.1% SDS followed by 0.1×SSC, 0.1% SDS; and (c) optionally sequencing the genomic fragment that comprises the clone identified in step (b), wherein the sequenced genomic fragment encodes all or substantially all of an amino acid sequence encoding a bacterial aromatic ring opening enzyme.

Availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. *Adv. Immunol.* 36:1 (1984); Maniatis).

Recombinant Expression

The genes and gene products of the instant sequences may be produced in heterologous host cells, particularly in the cells of microbial hosts. Expression in recombinant microbial hosts may be useful for the expression of various pathway intermediates; for the modulation of pathways already existing in the host or for the synthesis of new products heretofore not possible using the host.

For example, the genes that comprise aromatic ring cleavage operons (ORFs 1–4, 7) (Wackett, *Ann. N. Y. Acad. Sci.* 864:142–52 (1998)) are useful for the production of enzyme biocatalysts for synthesis of chemicals. Another potential application of ring opening genes involves construction of bacterial strains that could be used for in situ bioremediation of sites contaminated with aromatic compounds. The types of chemicals that might be synthesized using enzymes encoded by the genes in a ring cleavage operon are varied. Likewise, the conditions under which a bacterial strain designed for bioremediation must function are varied. Accordingly, it is desirable to have a library of unique ring cleavage genes so that several genes can be tested to identify the one most suitable for a particular application.

Preferred heterologous host cells for expression of the instant genes are microbial hosts. Specific suitable hosts include but are not limited Aspergillus, Saccharomyces, Pichia, Candida, Hansenula, Salmonella, Bacillus, Acinetobacter, Rhodococcus, Streptomyces, Escherichia, and Pseudomonas.

Microbial expression systems and expression vectors containing regulatory sequences that direct high level expression of foreign proteins are well known to those skilled in the art. Any of these could be used to construct chimeric genes for production of the any of the gene products of the instant sequences. These chimeric genes could then be introduced into appropriate microorganisms via transformation to provide high level expression of the enzymes.

Additionally, chimeric genes will be effective in altering the properties of the host bacteria. It is expected, for example, that introduction of chimeric genes encoding one or more of the instant bacterial aromatic ring opening enzymes will confer on the host the ability to degrade aromatic compounds. Several pathways for the degradation of various aromatics have been characterized. The TOL pathway typifies the general strategy that is used by many different bacteria to degrade a large variety of other aromatic compounds (Williams and Sayers, *Biodegradation* 5:195–217 (1994)). Degradation of the aromatic substrate is divided into three stages. The aromatic compound is first converted to catechol or a substituted catechol, such as protocatechuate. The aromatic ring of the catechol is opened in the second stage. Opening the aromatic ring is a key reaction because most of the energy that can be obtained from the molecule is available only after this point. During the third stage of degradation, the ring cleavage product is converted to small aliphatic compounds that enter central metabolism.

Two types of ring opening reactions occur with catechol (Scheme 1). The ortho cleavage reaction, catalyzed by enzymes such as catechol 1,2-dioxygenase, opens the aromatic ring of catechol between the two hydroxy groups (Ngai et al., *Meth. Enzymol.* 188:122–126 (1990)). The meta cleavage reaction, catalyzed by enzymes such as catechol 2,3-dioxygenase, opens the aromatic ring of catechol next to the two hydroxy groups (Kataeva and Golovleva, *Meth. Enzymol.* 188:115–121 (1990)). Accordingly, two general types of ring cleavage pathways are possible for mono-substituted, monocyclic aromatic compounds such as toluene or phenol (Williams and Sayers, supra). The ortho cleavage pathways have a catechol 1,2-dioxygenase and the enzymes necessary for further degradation of cis, cis-muconic acid. The meta cleavage pathways have a catechol 2,3-dioxygenase and the enzymes necessary for further degradation of hydroxymuconic semialdehyde.

Scheme 1
ortho and meta cleavage of catechol ortho Cleavage:

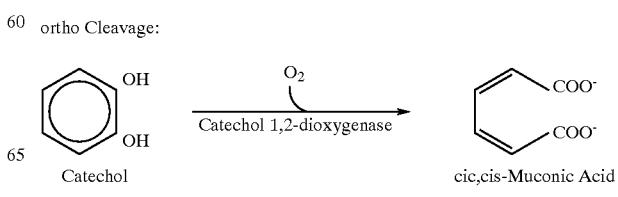

meta Cleavage:

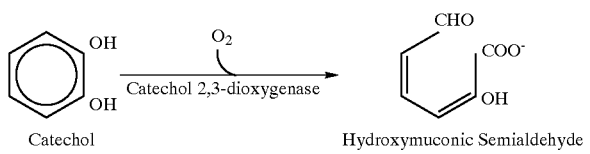

Catechol → Hydroxymuconic Semialdehyde

There are many different aromatic ring cleavage pathways for a large variety of aromatic compounds. Although many of the ring cleavage pathways have similar genetic organization (Williams and Sayers, supra), they tend to differ significantly in exact substrate specificity and other characteristics. As a result, a bacterial strain that degrades a wide range of aromatic compounds is likely to have several distinct ring cleavage operons, each of which is used to degrade a different set of aromatic compounds. Thus, it is not possible to predict from one organism to another whether a plasmid exists, an if so, whether it will contain genes useful for aromatic ring opening reactions.

Within the context of the present invention, several new genes have been identified that encode enzymes having ring-opening degradative activity. In particular, host cells comprising ORF1 and ORF2 (encoding a bacterial dioxygenase and its corresponding ferredoxin) will be expected to effect the bioconversion of a catechol substrate to the corresponding semialdehyde (see FIG. 3). Suitable catechol substrates are those according to formula I:

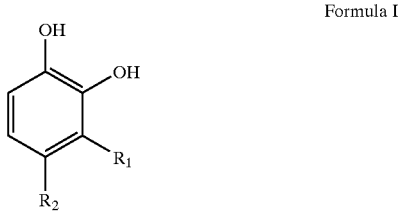

Formula I wherein $R_1$ may be selected from the group H, $CH_3$, and Cl, and $R_2$ may be selected from the group H, $CH_3$ and $COO^-$. Typical catechol substrates include but are not limited to catechol, 3-methylcatechol, 4-methylcatechol, 3-chlorocatechol, 4-chlorocatechol and protocatechuate.

Figure 3:
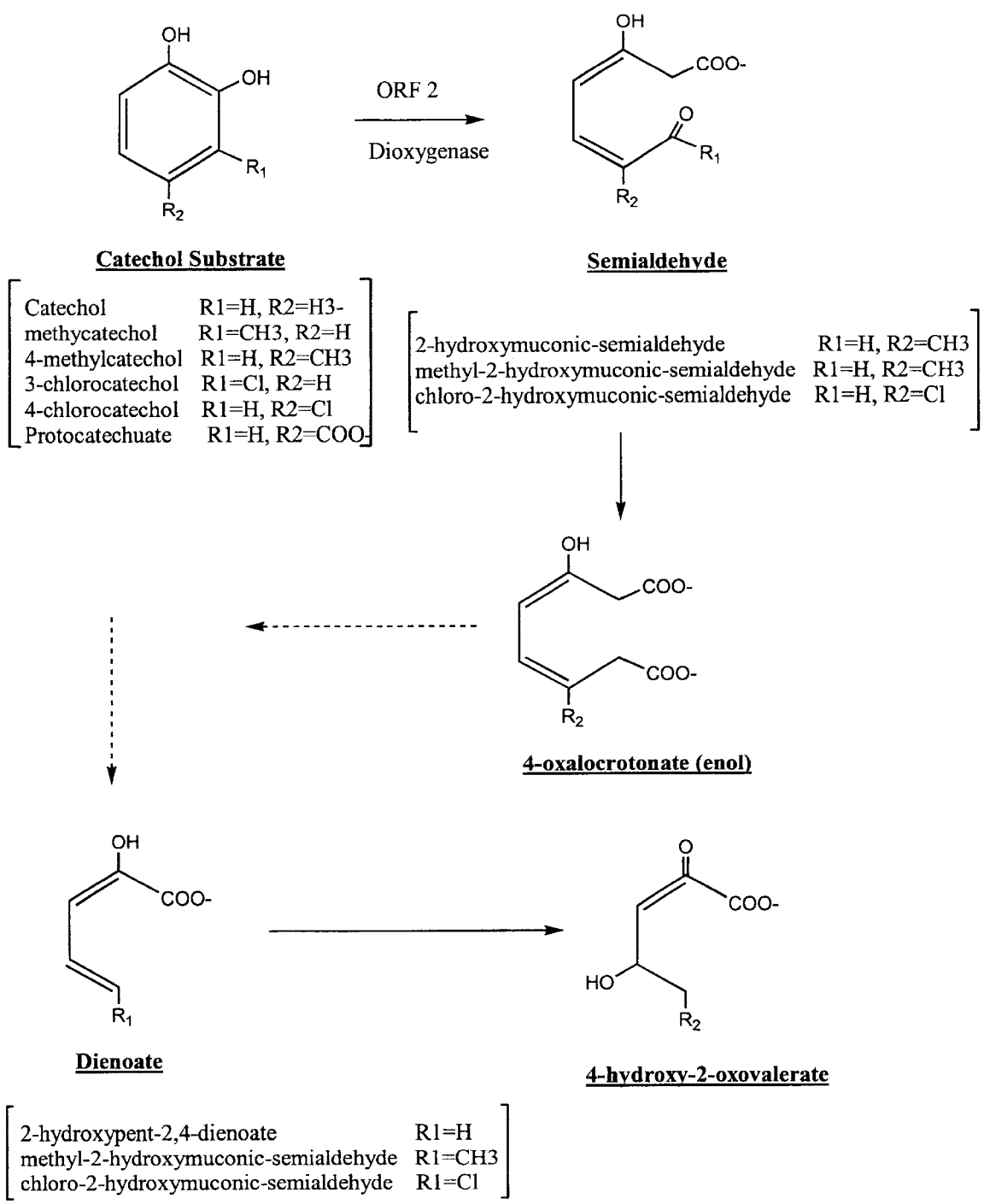
FIG. 3 illustrates the key ring opening reactions effected by enzymes encoded by ORF's 1, 2, 4, and 7.

Similarly a host cell comprising the instant bacterial dehydrogenase as encoded by ORF 4 will be expected to effect the conversion of semialdehyde substrates to 4-oxalocrotonate (enol) (see FIG. 3). Semialdehyde substrates suitable in the present invention are those according to formula II:

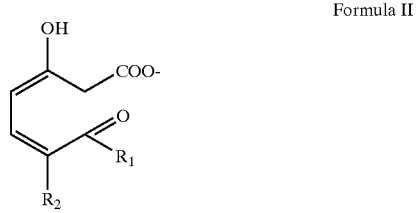

Formula II wherein $R_1$ is H and $R_2$ may be selected from the group $CH_3$ and Cl. Typical semialdehyde substrates include but are not limited to 2-hydroxymuconic-semialdehyde, methyl-2-hydroxymuconic-semialdehyde and chloro-2-hydroxymuconic-semialdehyde.

Additionally a host cell transformed with the instant bacterial hydratase as encoded by ORF 7 will be expected to effect the conversion of dienoate compounds to the corresponding valerates (see FIG. 3). Suitable substrates for the bacterial hydratase are those according to formula III:

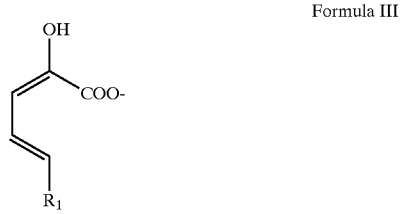

Formula III wherein $R_1$ is selected from the group H, Cl and $CH_3$. Suitable substrates for the bacterial hydratase include dienoates as well as semialdehydes such as, 2-hydroxypent-2,4-dienoate, methyl-2-hydroxymuconic-semialdehyde and chloro-2-hydroxymuconic-semialdehyde.

It will be appreciated that the instant pCT14 plasmid contains a variety of ORF's encoding proteins of many diverse functions, including hydrocarbon degradation, glutathione-S transferase (GST) activity and mercury tolerance. It is contemplated therefore that a host cell transformed with the pCT14 plasmid will demonstrate the ability to degrade a variety of hydrocarbons as well as achieving increased tolerance to mercury. The glutathione-S transferases (GSTs) represent a large group of detoxification enzymes. GSTs catalyze the conjugation of glutathione, homoglutathione and other glutathione-like analog via sulfhydryl group, to a large range of hydrophobic, electrophilic compounds. The conjugation can result in detoxification of these compounds. GST genes are found in both prokaryotic (e.g., *E. coli*) and eukaryotic organisms (e.g., yeast, plant and human). Although the homologies between the GSTs from prokaryotes and eukaryotes were low, many of the residues assigned to be important for the enzymatic function or structure in the eukaryotes were found to be conserved in prokaryotic GSTs (Nishida et al., *J. Biol Chem* 269:32536–32541 (1994)). It has been suggested that bacterial GST may represent a defense against the effects of antibiotics (Piccolomini et al., *J Gen Microbiol* 135:3119–3125 (1989)). Accordingly it is contemplated that a host strain transformed with the CT14 plasmid will have the ability detoxify harmful compounds via conjugation of those compounds to glutathione.

The instant plasmid additionally encodes a variety of maintenance proteins, useful for maintaining, stabilizing and replicating the plasmid. It is contemplated that these genes may be used in conjunction with other bacterial plasmids deficient in these functions for the increased stabilization or robust maintenance of the plasmid. Bacterial maintenance proteins of particular interest on the pCT14 plasmid include the REP origin of replication (encoded by ORF 38) the TRA proteins (TRAI, TRAJ and TRAK, encoded by ORF's 23, 24 and 25 respectively) and the VAG proteins (VAGD and VAGC, encoded by ORF's 33 and 34 respectively). The tra gene family is known to be involved in plasmid conjugation, a process that promotes DNA transfer from a donor to a recipient cell mediated by physical contact (Firth et al, *Escherichia coli* and Salmonella: *Cellular and Molecular Biology*, ASM press (1996)). Among tra gene products, TraI and TraK proteins are reported to be required for efficient plasmid site-specific recombination (Paterson et al. *J. Bacteriol* 181:2572–2583 (1999)). Furthermore, TraI is required for conjugal DNA transfer. Fukuda and Ohtsubo (*Genes Cells* 2:735–751 (1997)) reported that TraI has the activity of site- and strand-specific nicking of the supercoiled plasmid DNA. TraJ, traJ gene product, regulates transcription originating at the tra operon promoter $P_{traY}$. (Firth et al., *Escherichia coli* and Salmonella: *Cellular and Molecular Biology*, ASM press (1996)). The stabilization proteins VAGC and VAGD encoded by vagC and vagD are involved in the maintaining the plasmid as an autonomous replicating unit.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, ara, tet, trp, $IP_L$, $IP_R$, T7, tac, and trc (useful for expression in *Escherichia coli*) as well as the amy, apr, npr promoters and various phage promoters useful for expression in Bacillus.

Termination control regions may also be derived from various genes native to the preferred hosts. Optionally, a termination site may be unnecessary, however, it is most preferred if included.

Protein Evolution

Sections of various naturally occurring homologs or alleles of a particular ring cleavage gene could be combined with each other to form new versions of the gene by means of the technique known as "gene shuffling" (U.S. Pat. Nos. 5,605,793; 5,811,238; 5,830,721; and 5,837,458, incorporated herein by reference). It is contemplated that the present nucleotide may be used to produce gene products having enhanced or altered activity. Various methods are known for mutating a native or wild type gene sequence to produce a gene product with altered or enhanced activity including but not limited to error prone PCR (Melnikov et al., *Nucleic Acids Research*, (Feb. 15, 1999) Vol. 27, No. 4, pp. 1056–1062); site directed mutagenesis (Coombs et al., *Proteins* (1998), 259–311, 1 plate. Editor(s): Angeletti, Ruth Hogue. Publisher: Academic, San Diego, Calif.) and "gene shuffling" (U.S. Pat. Nos. 5,605,793; 5,811,238; 5,830,721; and 5,837,458, incorporated herein by reference).

The method of gene shuffling is particularly attractive due to its facile implementation, and high rate of mutagenesis and ease of screening. The process of gene shuffling involves the restriction of a gene of interest into fragments of specific size in the presence of additional populations of DNA regions of both similarity to or difference to the gene of interest. This pool of fragments is then denatured and then reannealed to create a mutate gene. The mutated gene is then screened for altered activity.

The instant bacterial sequences of the present invention may be mutated and screened for altered or enhanced activity by this method. The sequences should be double stranded and can be of various lengths ranging form 50 bp to 10 kb. The sequences may be randomly digested into fragments ranging from about 10 bp to 1000 bp, using restriction endonucleases well known in the art (Maniatis supra). In addition to the instant bacteria sequences populations of fragments that are hybridizable to all or portions of the bacterial sequence may added. Similarly, a population of fragments which are not hybridizable to the instant sequence may also be added. Typically these additional fragment populations are added in about a 10 to 20 fold excess by weight as compared to the total nucleic acid. Generally if this process is followed the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from 80° C. to 100° C. The nucleic acid fragments may be reannealed by cooling. Preferably the temperature is from 20° C. to 75° C. Renaturation can be accelerated by the addition of polyethylene glycol (PEG) or salt. The salt concentration is preferably from 0 mM to 200 mM. The annealed nucleic acid fragments are next incubated in the presence of a nucleic acid polymerase and dNTP's (i.e. dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from 2 to 50 times, more preferably the sequence is repeated from 10 to 40 times. The resulting nucleic acid is a larger double-stranded polynucleotide of from about 50 bp to about 100 kb and may be screened for expression and altered activity by standard cloning and expression protocol (Maniatis supra).

Construction of Cloning Vectors

The present invention is useful for providing unique plasmid nucleotide sequences, genes, and gene products. These sequences have utility in construction of plasmid cloning vectors for Pseudomonas, degradation of aromatic compounds for bioremediation, production of biocatalysts for transformation of catechol and other chemicals, and development of molecular probes for detecting plasmids. The present invention advances the art related to these utilities by expanding the range of unique nucleotide sequences, genes, and gene products available for direct use and for modification by those familiar with the techniques of molecular biology.

The ori sequence and associated genes for replication (ORF38) and partitioning of a plasmid have potential utility in biotechnology. These sequences are essential in construction of plasmid cloning vectors. The ori and associated sequences could be used alone to make vectors for a specific bacterial species or in combination with ori sequences from an *Escherichia coli* plasmid to make shuttle vectors for moving cloned DNA between *E. coli* and another species.

Description of the Preferred Embodiments

Pseudomonas strain CT14 was isolated on the basis of being able to grow on toluene as the sole source of carbon and energy. At first, a culture was obtained from a wastewater treatment facility. The bacterial cultures were grown in the presence of toluene(100 ppm) to select for the toluene tolerant strains. Bacteria that utilized the toluene as a sole source of carbon and energy were further isolated by spreading samples of the culture mentioned above on the S12 agar plate with toluene placed on the interior of each petri dish lid. The isolates that utilized toluene for growth were then further tested with other aromatic compounds and intermediates from toluene degradation pathways. One of the strains that grew on toluene and m-xylene was named CT14. Analysis of 16s RNA gene sequence confirmed that CT14 belongs to genus Pseudomonas.

A 54 kb plasmid was isolated from CT14 strain and designated pCT14. Entire pCT14 was sequenced and overlapping sequences of the clones were assembled to form a contiguous sequence for pCT14. The gaps between the contigs were closed by using PCR to amplify the regions between various contigs.

The pCT14 contains many long open reading frames (ORFs) that corresponded to genes. The function of each genes on pCT14 was determined by comparing the pCT14 ORFs to the sequences in the GenBank sequence database using BLAST program at the National Center for Biotechnology Information (NCBI). The NCBI-BLAST algorithm was used to translate all six reading frames of pCT14 DNA sequences into amino acid sequences and to compare all ORFs to sequences in the GenBank database. Function was assigned to each ORF based upon homology with GenBank sequences. Table 3 lists ORFs on pCT14 and genes from GenBank database that have homology in comparison to pCT14 ORFs.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual;* Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology,* Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "$\mu$L" means microliters, "L" means liters, "$\mu$M" means micromoles, "mM" means millimoles.

Media and Culture Conditions:

Materials and methods suitable for the maintenance and growth of bacterial cultures were found in *Manual of Methods for General Bacteriology* (Phillip Gerhardt, R. G. E. Murray, Ralph N. Costilow, Eugene W. Nester, Willis A. Wood, Noel R. Krieg and G. Briggs Phillips, eds), pp. 210–213, American Society for Microbiology, Washington, DC. or Thomas D. Brock in *Biotechnology: A Textbook of Industrial Microbiology,* Second Edition (1989) Sinauer Associates, Inc., Sunderland Mass. All reagents and materials used for the growth and maintenance of bacterial cells were obtained from Aldrich Chemicals (Milwaukee, Wis.), DIFCO Laboratories (Detroit, Mich.), Gibco/BRL (Gaithersburg, Md.), or Sigma Chemical Company (St. Louis, Mo.) unless otherwise specified.

Synthetic S12 medium was used to establish enrichment cultures and to culture bacteria for production of terephthalic acid. S12 medium contains: ammonium sulfate, 10 mM; potassium phosphate buffer, pH 7.0, 50 mM; $MgCl_2$, 2 mM; $CaCl_2$, 0.7 mM; $MnCl_2$, 50 $\mu$M; $FeCl_3$, 1 $\mu$M; $ZnCl_3$, 1 $\mu$M; $CuSO_4$, 1.72 $\mu$M; $CoCl_2$, 2.53 $\mu$M; $Na_2MoO_2$, 2.42 $\mu$M; $FeSO_4$, 0.0001% (wt/v); and thiamine hydrochloride, 2 $\mu$M.

S12 agar was used to isolate bacteria from liquid enrichment cultures that grow on p-xylene and to test isolates for growth with p-xylene, p-toluic acid, or terephthalic acid supplied a sole source of carbon and energy. S12 agar was prepared by adding 1.5% (wt/v) Noble agar (Difco) to S12 medium.

Bacteria growing in S12 medium were supplied with toluene by adding the toluene directly to the culture medium. Bacteria growing on S12 agar were supplied with toluene or other volatile aromatic compounds as vapor by placing 10 to 20 $\mu$L of a volatile compound on the interior of the petri dish lid. The petri dish was then sealed with parafilm and incubated with the lid on the bottom.

Molecular Biology Techniques:

Restriction enzyme digestions, ligations, transformations, and methods for agarose gel electrophoresis were performed as described in Sambrook, J., et al., *Molecular Cloning: A Laboratory Manual,* Second Edition, Cold Spring Harbor Laboratory Press (1989). Polymerase Chain Reactions (PCR) techniques were found in White, B., *PCR Protocols: Current Methods and Applications,* Volume 15 (1993) Humana Press Inc.

Example 1

Isolation and Initial Characterization of Strain CT14

Example 1 demonstrated the isolation of strain CT14 on the basis of being able to grow on toluene as the sole source of carbon and energy. The ability of strain CT14 to grow on various substrates of the TOL pathway for degradation of toluene, m-xylene, and p-xylene indicated that strain CT14 utilized the TOL pathway or a similar pathway to degrade toluene. Analysis of a 16s rRNA gene sequence indicated that strain CT14 was related to gamma proteobacteria belonging to the genus Pseudomonas.

Bacteria that grow on toluene were isolated from an enrichment culture. The enrichment culture was established by inoculating I mL of activated sludge into 10 mL of S12 medium in a 125 mL screw cap Erlenmeyer flask. The activated sludge was obtained from a DuPont wastewater treatment facility. The enrichment culture was supplemented with 100 ppm toluene added directly to the culture medium and was incubated at 25° C. with reciprocal shaking. The enrichment culture was maintained by adding 100 ppm of toluene every 2–3 days. The culture was diluted every 10 d by replacing 9 mL of the culture with the same volume of S12 medium. Bacteria that utilize toluene as a sole source of carbon and energy were isolated by spreading samples of the enrichment culture onto S12 agar. Toluene was placed on the interior of each petri dish lid. The petri dishes were sealed with parafilm and incubated upside down at room temperature (approximately 25° C.). Representative bacterial colonies were then tested for the ability to use toluene as a sole source of carbon and energy. Colonies were transferred from the S12 agar plates to S12 agar plates and supplied with toluene on the interior of each petri dish lid. The petri dishes were sealed with parafilm and incubated upside down at room temperature (approximately 25° C.). The isolates that utilized toluene for growth were then tested for growth on S12 agar plates containing other aromatic compounds and intermediates of known pathways for toluene degradation.

The 16s rRNA genes of each isolate were amplified by PCR and analyzed as follows. Each isolate was grown on R2A agar (Difco Laboratories, Detroit, Mich.). Several colonies from each culture plate were suspended in 200 mL of lysis buffer (1% Triton X-100, 20 mM Tris (pH 8.5), 2 mM EDTA). The mixture was heated to 95° C. for 10 min and then centrifuged to remove cellular debris. The 16s rRNA gene sequences in the supernatant were amplified by PCR by using a commercial kit according to the manufacturer's instructions (Perkin Elmer, Norwalk, Conn.) with primers HK12 (GAGTTTGATCCTGGCTCAG) [SEQ ID NO:24] and HK13 (TACCTTGTTACGACTT) [SEQ ID NO:25]. PCR was performed in a Perkin Elmer GeneAMp 9600. The samples were incubated for 5 min at 94° C. and then cycled 35 times at 94° C. for 30 sec, 55° C. for 1 min, and 72° C. for 1 min. The amplified 16s rRNA genes were purified using a commercial kit according to the manufacturer's instructions (QIAquick PCR Purification Kit, Valencia, Calif.) and sequenced on an automated ABI sequencer (Applied Biosystems, Foster City, Calif.). The sequencing reactions were initiated with primers HK12, HK13, and HK14 (GTGCCAGCAGYMGCGGT; Y=C or T, M=A or C) [SEQ ID NO:26]. The 16s rRNA gene sequence of each isolate was used as the query sequence for a BLAST search (Altschul, et al., *Nucleic Acids Res.* 25:3389–3402 (1997)) of GenBank for similar sequences.

The data in Table 1 indicated strain CT14 was able to grow on toluene and m-xylene. Strain CT14 also grew on intermediates of the TOL upper pathway that are predicted for degradation of toluene and m-xylene. Strain CT14 was unable to utilize any of the other compounds that were tested.

A 16s rRNA gene of strain CT14 was sequenced and compared to other 16s rRNA sequences in the GenBank sequence database. The 16s rRNA gene sequence from strain CT14 was at least 99% homologous to the 16s rRNA gene sequences of gamma proteobacteria belonging to the genus Pseudomonas.

TABLE 1

Summary of Carbon Source Utilization for the Strain CT14

| Carbon Source | Growth on Carbon Source |
|---|---|
| toluene | + |
| benzyl alcohol | + |
| benzaldehyde | + |
| benzoate | + |
| m-xylene | + |
| m-toluate | + |
| p-xylene | − |
| p-toluate | − |
| benzene | − |
| phenol | − |
| o-cresol | − |
| m-cresol | − |
| p-cresol | − |
| cumene | − |
| ethylbenzene | − |
| chlorobenzene | − |
| aniline | − |

Example 2

Isolation and Physical Characterization of a Plasmid from Pseudomonas Strain CT14

Many bacteria harbor plasmids that carry genes for degradation of aromatic compounds (Tan, *Appl. Microbiol. Biotechnol.* 51:1–12 (1999)). Example 2 demonstrated by pulse field gel electrophoresis (PFGE) that strain CT14 contained a plasmid that is 54 kb in size. The plasmid was designated pCT14.

Preparation of DNA for PFGE:

Strain CT14 was inoculated into 100 mL of LB medium in a 1 L Erlenmeyer flask. The culture was incubated for 17 h at 37° C. with reciprocal shaking. The culture was transferred to 30 mL Corex centrifuge tubes (25 mL of culture/tube). The cells were collected by centrifugation in a Sorvall RC5C centrifuge using a SS-34 rotor for 10 min at 5000 rpm at 4° C. The cell pellet in each tube was resuspended in 2 mL of Solution 1 (50 mM Tris-HCl, pH 7.5, 10 mM EDTA, 100 mg/mL RNase A). The cells were lysed by adding 2 mL of Solution 2 (0.2 M NaOH, 1% SDS), sealing the tubes with Parafilm, and gently rocking the tubes until the cell suspensions cleared. The cell lysates were neutralized by adding 2 mL of Solution 3 (1.32 M potassium acetate, pH 4.8) to each tube, sealing the tubes with Parafilm, and gently inverting the tubes until a white precipitate formed. The tubes were centrifuged in a Sorvall RC5C centrifuge using a SS-34 rotor for 30 min at 12000 rpm. The supernatant was gently poured into a fresh 30 mL Corex tube. The DNA was precipitated by adding 4 M NaCl to the supernatant to a final concentration of 0.4 M, 2.5 volumes of 100% ethanol, and placing the tubes at −20° C. for 17 h. The precipitated DNA was recovered by centrifugation in a Sorvall RC5C centrifuge using a SS-34 rotor for 45 min at 12000 rpm. The supernatant was removed. The white pellet was washed with cold (approximately −20° C.) 70% ethanol and dried by rotary evaporation. The dried pellet was dissolved in 250 μL of deionized water and stored at −20° C. until used for PFGE (Pulse Field Gel Electrophoresis).

Plasmid DNA was separated from chromosome DNA by Pulse Field Gel Electrophoresis (PFGE) in a 1% low melting point agarose gel in 0.5×TBE buffer. PFGE was performed with a Hoeffer SuperSub gel box, PC500 Switchback Pulse Controller, PS500XT DC Power Supply, and RCB-300 Refrigerated Circulating Bath (Hoeffer Scientific Instruments, San Francisco, Calif.). Samples of DNA (75 μL) were subjected to electrophoresis for 18–28 h (5–7.7 V/cm, 3:1 switch, and 50–80 sec pulse times at 12° C.). Plasmid DNA was detected as a single band.

The bands containing plasmid DNA were excised from the pulse field gel. The gel slices were placed into 1.5 mL polypropylene microfuge tubes and melted at 70° C. The melted agarose was transferred to new microfuge tubes in 500 mL aliquots. An equal volume of Tris-saturated Phenol was added to the agarose in each tube. The aqueous layer from each tube was transferred to a fresh microfuge tube and extracted two times with chloroform:isoamyl alcohol (24:1). The DNA was precipitated by adding 3 M ammonium acetate (pH 5.2) to a final concentration of 0.3 M and 2.5 volumes of 100% ethanol. The samples were placed at –70° C. overnight. The precipitated DNA was recovered by centrifugation in a microfuge for 30 min at 14,000 rpm at 4° C. The DNA pellet was washed with 70% ethanol and dried by rotary evaporation for 10 min. The DNA was dissolved in 50 μL of sterile deionized $H_2O$.

Size Determination:

PFGE purified pCT14 DNA was digested with restriction enzyme EcoRI. The restriction fragments were separated on a 1% 1X TAE agarose gel. The gel was stained with ethidium bromide, and the DNA bands were visualized under ultraviolet light. A digital image of the gel was generated using the Eagle Eye (Stratagene, La Jolla, Calif.). The sizes of the restriction fragments were determined from the gel image using Advanced Quantifier gel analysis software (Bio Image Systems Corp., Ann Arbor, Mich.). EcoRI digestion of pCT14 resulted in 7 restriction fragments (Table 2). The combined lengths of the restriction fragments indicated that pCT14 was approximately 50 Kb in size.

TABLE 2

EcoRI Restriction Fragments of pCT14

| Fragment No. | Length (bp) |
| --- | --- |
| 1 | 13,688 |
| 2 | 9,922 |
| 3 | 8,106 |
| 4 | 6,505 |
| 5 | 5,600 |
| 6 | 4,710 |
| 7 | 2,972 |
| Total Length | 51,503 |

Example 3

Nucleotide Sequence of Plasmid pCT14

Characterization of the types and arrangement of genes on a plasmid can be accomplished by sequencing the entire plasmid. Two strategies were used to create libraries of cloned pCT14 DNA for sequencing. One strategy involved cloning overlapping restriction fragments that were generated by combinations of different restriction nucleases having 6-base pair recognition sequences. The other strategy involved cloning restriction fragments from a semirandom array of restriction fragments that was generated by partial digestion of pCT14 DNA with a restriction nuclease having a 4-base pair recognition sequence. Numerous clones from the libraries were sequenced. The overlapping sequences of the clones were assembled to form a contiguous sequence for pCT14. Example 3 demonstrated the entire nucleotide sequence of pCT14.

PFGE-purified pCT14 DNA was cut with combination of 2 restriction enzymes. They are EcoRI and BamHI, EcoRI and HindIII, or EcoRI and SalI. Each preparation of cut DNA was ligated to the cloning vector pIBI31 (IBI Biosystems, New Haven, Conn.) that had been cut with the same combination of restriction enzymes. The ligated DNA was transformed into sub-cloning efficiency competent DH5α (Gibco-BRL, Gaithersburg, Md.). The transformed bacteria were plated onto LB agar containing ampicillin (100 μg/mL) and 20 mM X-gal (5-bromo-4-chloro-galactopyranosidase). The plates were incubated at 37° C. overnight.

White colonies contained vector plasmids with cloned inserts. Each white colony was replica plated onto fresh LB agar containing ampicillin (100 μg/mL) and 20 mM X-gal, and also inoculated into 2 mL of LB liquid media containing Ampicillin (100 μg/μL) in 15 mL Falcon tubes. The tubes were incubated at 37° C. in a rotary shaker. After overnight incubation, the bacteria in each culture were collected by centrifugation for 3 min at 4000 rpm in an RC5C centrifuge using a SM-24 rotor. The cell pellets were resuspended in 200 μL of Solution 1. The bacteria were lysed by adding 200 μL of Solution 2. The cell lysates were neutralized by adding 200 μL of Solution 3 to each tube. The samples were centrifuged at room temperature for 10 min at 10,000 rpm in a table top centrifuge (Microspin 24S, Sorvall). The supernatants was transferred to Centricon-100 concentrators (Amicon, Beverly, Mass.), 2 mL of deionized $H_2O$ was added to each sample, and the concentrators were centrifuged in a SM-24 rotor for 1 h at 2,840 rpm. The concentrates were transferred to 1.5 mL microfuge tubes.

The samples of concentrated DNA were sequenced on an automated ABI sequencer. Each clone was initially sequenced using the universal forward and reverse priming sites present on the pIBI31 vector. The sequence obtained from a particular cloned insert was used to design new primers to initiate additional sequencing reactions for that clone. This process was repeated until sequencing of the insert on both strands was completed.

Plasmid pCT14 was partially digested with MboI restriction enzyme generating a majority of fragments approximately 1–2 kb in size which were ligated into pIBI31 (Integrated Biosystems Inc., Benecia, Calif.) digested with BamHI restriction enzyme. The ligations were transformed into DH5α competent cells (Gibco-BRL, Gaithersburg, Md.). The transformed bacteria were plated onto LB agar containing 100 μg/mL Ampicillin and 20 mM X-gal in large square plates (Genetix, United Kingdom). The blue-white colorimetric screen was used to identify colonies containing inserts. The colonies were picked using a Q Bot robotic colony picker (Genetix) and sequenced using an ABI sequencer.

A combination of computer applications were used to assemble the sequences. Sequences were imported into Sequencher 3.0 (GeneCodes, Ann Arbor, Mich.) and also assembled using Phred (Ewing et al, Genome Research 8: 175–185 (1998)) to do the reads from the ABI sequence chromatographs, Cross-match (Rieder et al., *Nucleic Acids Research* 26:967–973 (1998)) to remove vector sequences and Phrap (Rieder et al., *Nucleic Acids Research* 26: 967–973 (1998)) for the sequence assembly. Both methods were used and then compared against each other to determine the correct assembly.

The gaps between the contigs that were generated using Sequencher or Phrap were closed by using PCR to amplify the regions between various contigs. Regions approximately 150–200 bp from the end of each contig with a G+C content of 50–70% were used as priming sites for gap closure sequencing. PCR reactions were done using pCT14 as a template under standard PCR protocols. The PCR reactions were run on 1% 1X TEA agarose gels to verify the presence of a product. In the cases where a single PCR product was obtained, the reaction was purified using the Qiagen PCR Cleanup Kit (Qiagen, Valencia, Calif.). Multiple products were excised and purified using the Qiagen Gel Purification Kit separately. The purified products were sequenced using the original PCR primers as sequencing primers. The resulting sequences were then added to the assembly to join the contig fragments.

Primers were designed that would yield PCR products spanning the repeat regions. A commercial long range PCR kit (Perkin-Elmer) was used to amplify the repeat regions. The conditions for long range PCR were 25 cycles at 94° C. for 30 sec and 68° C. for 15 min. This resulted in two 10 Kb PCR products using primers CT14–35+CT14–40 and primers CT14–39+CT14–40. Each of the fragments was nebulized using a modified Aeromist Treatment Set w/Reservoir (IPI Medical Products, Chicago, Ill.) (FIG. 1). The mouth piece and flexible tube were discarded. The inner splash guard was removed and the outer lip was cut away with a pair of scissors and then reinserted upside down. The long rubber tubing was attached to a filtered air line at 18 psi. The fragments were nebulized for 30 to 60 sec and concentrated using a Qiagen PCR Cleanup Kit. Nebulized fragments were polished using pfu DNA polymerase (Stratagene, address). Approximately 100 ng of nebulized DNA in 20 µL of $dH_2O$ was ligated to SmaI digested pUC18 (Ready-to-go Kit, Stratagene). The ligation was precipitated by adding 7.5 µL of 4 M NaCl (final concentration of 1.5 M) and 2 volumes of cold ethanol. The sample was incubated at −70° C. overnight. The DNA was pelleted by centrifugation (Brinkmann 5415, Westbury, N.Y., 30 min at 14000 rpm at 4° C.). The DNA pellets were washed twice with 70% ethanol, air dried, and resuspended in 100 µL of deionized $H_2O$. The ligated DNA was electrotransformed in DH10b ElectroMax Competent Cells (Gibco-BRL) at 25 kV/cm. The transformation was plated onto LB agar containing 100 µg/mL of ampicillin and 20 mM X-gal. Positive clones were sequenced using universal primers and assembled to reconstruct the PCR fragments. The resulting PCR product sequences were included in assembly of the pCT14 sequence. The complete pCT14 sequence contained 55,216 bp.

Example 4

Characterization of Open Reading Frames on pCT14

The assembled pCT14 nucleotide sequence contained many long open reading frames (ORFs) that corresponded to genes. The function of each pCT14 gene was determined by comparing the pCT14 ORFs to the sequences in the GenBank sequence database using the BLAST program at the National Center for Biotechnology Information (NCBI). The parameter for the BLAST program was set on the default setting. Example 4 demonstrated that pCT14 contains a set of novel genes for cleavage of an aromatic ring and conversion of the ring cleavage product to small aliphatic compounds.

Figure 2:
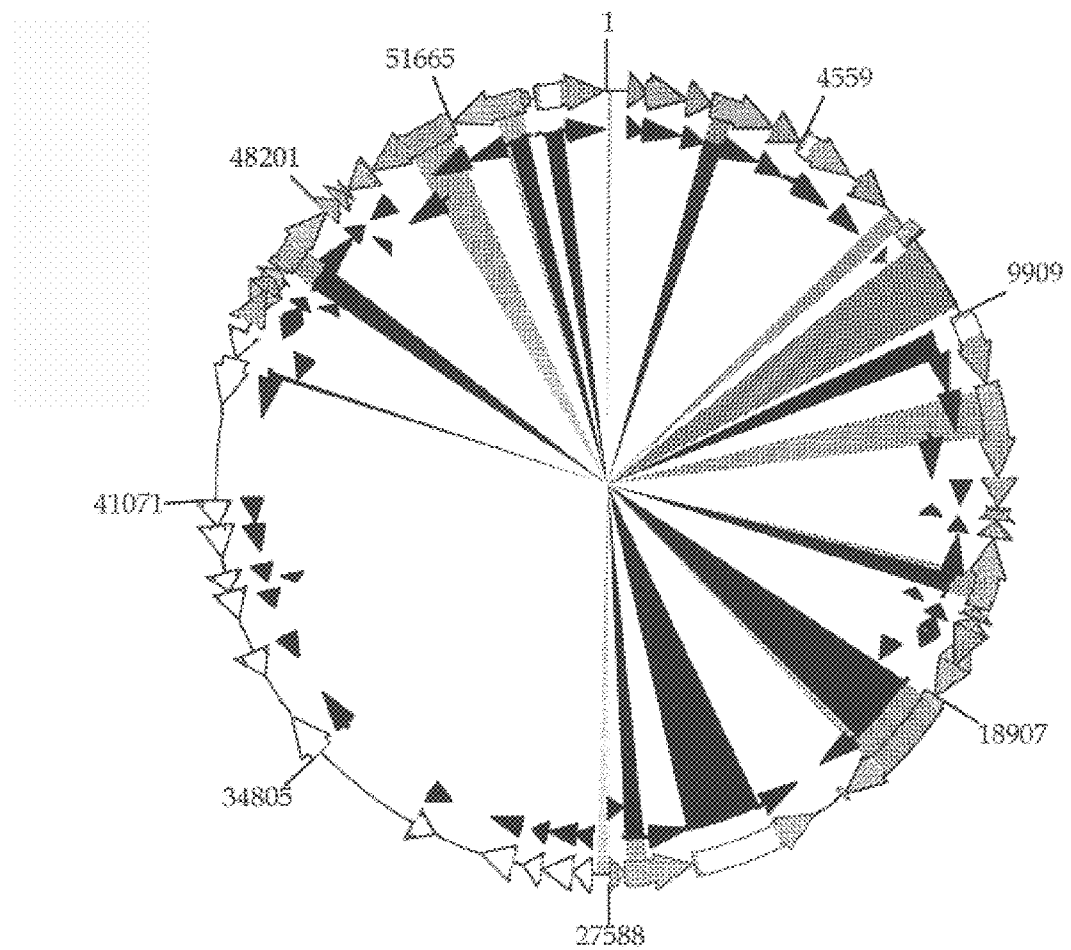
FIG. 2 is a plasmid map showing all ORFs in pCT14.

Identification of ORFs:

The NCBI-Blast algorithm was used to translate all six reading frames of the pCT14 DNA sequence into amino acid sequences and to compare all ORFs to sequences in the GenBank database. The parameters were set on the default setting. Function was assigned to each ORF based upon homology with GenBank sequences. The start site of translation for each open reading frame was determined by the alignment to a homologous GenBank sequence. Gene Construction Kit (Textco, West Lebanon, N.H.) was used to prepare a list of ORFs (Table 3) and to draw a plasmid map that illustrates the orientation of each ORF (FIG. 2).

Most of the genes on pCT14 had high degrees of homology with GenBank sequences that are involved in plasmid replication, plasmid conjugation, transposition, or mercury resistance (Table 3). In addition to these genes, plasmid pCT14 has several ORFs (ORF 1, ORF 2, ORF 3, ORF 4, ORF 5, ORF 7) that encode an aromatic ring cleavage pathway (Table 5 and FIG. 3). The organization of the pCT14 ring cleavage genes is the same as other ring cleavage pathways (Williams and Sayers, *Biodegradation* 5:195–217 (1994)). However, adjacent to each other but are only 35% to 84% homologous at the amino acid level with the corresponding lower pathway genes of the well characterized TOL plasmid pWWO. Comparison of the pCT14 ring cleavage genes to sequences in GenBank suggests that the pCT14 ring cleavage genes have been assembled from several sources through recombination and transposition.

TABLE 3

List of ORFs for pCT14

| Open-reading frame | Range | | Direction | GenBank Sequence with Highest Homology |
| --- | --- | --- | --- | --- |
| ORF 1 | 552 | 911 | → | U20258: chloroplast-type ferredoxin |
| ORF 2 | 923 | 1867 | → | X59790: 3-methylcatechol 2,3-dioxygenase |
| ORF 3 | 1948 | 2411 | | AF109307: unknown *Pseudomonas putida* ORF |
| ORF 4 | 2450 | 3910 | → | (AB001722) 2-hydroxymuconic semialdehyde dehydrogenase |
| ORF 5 | 3947 | 4558 | → | (X76500) glutathione S-transferase |
| Transposase | 4560 | 5936 | → | (AF028594) transposase |
| ORF 7 | 6189 | 6983 | → | S24418 dmpE protein |
| Transposase | 7554 | 7698 | → | Alcaligenes sp. putative transposase (IS1071) gene |
| Transposase (partial) | 7699 | 7929 | → | sp|Q04222|TRA1_ALCSP |
| | 7930 | 9768 | — | PPY09450 *P. putida* plasmid pPGH1 DNA (DNA homology, no ORFs) |
| tniA | 9909 | 11588 | → | S70152 transposase |
| tniB | 11591 | 12499 | → | S70151 tnsC protein homolog |
| tniQ | 12496 | 13713 | → | S70150 tniQ protein |

TABLE 3-continued

List of ORFs for pCT14

| Open-reading frame | Range | | Direction | GenBank Sequence with Highest Homology |
|---|---|---|---|---|
| tniR | 13774 | 14388 | → | S70149 resolvase |
| merE | 14441 | 14677 | ← | S70148 merE protein |
| merD | 14673 | 15039 | ← | S70147 merD protein |
| merA | 15056 | 16702 | ← | MERA_PSEFL MERCURIC REDUCTASE |
| ORFF | 16699 | 16944 | ← | (X73112) ORF F potential protein |
| merP | 16947 | 17222 | ← | (U80214) MerP [*Pseudomonas stutzeri*] |
| merT | 17238 | 17588 | ← | MERCURIC TRANSPORT PROTEIN |
| merR | 17660 | 18094 | → | S32798 merR protein |
| tnpR | 18270 | 18906 | → | (AF028594) Tn5501 resolvase |
| tnpA | 18889 | 21918 | → | (Y09450) transposase |
|  | 21919 | 21950 | — | *P. putida* plasmid pPGH1 DNA (DNA homology, no ORFs) |
| ORF 23 | 22704 | 25659 | ← | (U43676) TraI [*Salmonella typhimurium*] |
| ORF 24 | 25660 | 27198 | ← | (AF000361) TraJ [*Salmonella typhimurium*] |
| ORF 25 | 27198 | 27587 | ← | (AF000361) TraK [*Salmonella typhimurium*] |
| ORFA | 27971 | 28387 | → | (U72482) PsiB-like protein [Plasmid pKM101] |
| ORFB | 28388 | 29092 | → | (U72482) unknown [Plasmid pKM101] |
| ORFC | 29112 | 29496 | → | (U72482) unknown [Plasmid pKM101] |
| ORFD | 29763 | 30542 | → | YMUC_SALTY HYPOTHETICAL |
| ORFE | 31614 | 32165 | ← | SINGLE-STRAND BINDING PROTEIN |
| ORFF | 34805 | 35839 | → | HYPOTHETICAL 31.3 KD PROTEIN |
| ORFG | 36948 | 37541 | ← | HYPOTHETICAL 21.5 KD PROTEIN IN GPA 5' REGION |
| ORF 33 | 38318 | 38755 | ← | VagD protein - *Salmonella dublin* virulence plasmid |
| ORF 34 | 38752 | 38988 | ← | VagC protein - *Salmonella dublin* virulence plasmid |
| ORFH | 38998 | 39423 | ← | (AE001167) *B. burgdorferi* predicted coding region BB0663 |
| ORFI | 39786 | 40436 | ← | HYPOTHETICAL 23.2 KD PROTEIN IN NUC 5' RFGION |
| pin | 40503 | 41070 | ← | (U73041) invertase/recombinase like protein |
| ORF 38 | 43194 | 44330 | ← | (L42524) rep: replication initiator and transcription repressor |
| rmin | 44317 | 44934 | ← | (AF015307) DNA invertase [*Acetobacter pasteurianus*] |
| merR | 45162 | 45596 | ← | merR protein |
| merT | 45668 | 46018 | → | S70143 mercury ion transport protein |
| merP | 46034 | 46310 | → | MERP_PSEFL |
| ORFF | 46312 | 46557 | → | S70145 mercuric ion transport protein |
| merA | 46554 | 48200 | → | S70146 mercuric ion reductase |
| merD | 48217 | 48582 | → | S70147 merD protein |
| merE | 48579 | 48815 | → | S70148 merE protein |
| tniR | 48868 | 49482 | ← | (L40585) resolvase |
| tniQ | 49543 | 50757 | ← | S70150 tniQ protein |
| tniB | 50754 | 51662 | ← | tnsC protein homolog - Xanthomonas sp |
| tniA | 51665 | 53344 | ← | (L40585) transposase |
|  | 53488 | 53610 | — | AF020724 *Pseudomonas fluorescens* plasmid pAM10.6 insertion sequence |
| transposase | 53636 | 55216 | → | (AF028594) transposase |

TABLE 4

| ORF Name | Gene Name | Similarity Identified | SEQ ID base | SEQ ID Peptide | % Identity[a] | E-value[b] | Citation |
|---|---|---|---|---|---|---|---|
| ORF1 | ferredoxin | ferredoxin (*Pseudomonas putida*) | 1 | 2 | 62 | 5.0E − 20 | Unpublished; GI4160463 |
| ORF2 | dioxygenase | Catechol 2,3-dioxygenase (*Pseudomonas putida*) | 3 | 4 | 70 | 2.2E − 165 | Unpublished; GI4160464 |
| ORF4 | dehydrogenase | Hydroxymuconic semialdehyde dehydrogenase (*Pseudomonas stutzeri*) | 5 | 6 | 63 | 9.3E − 214 | Bosch, R., et al., unpublished GI4104767 |
| ORF5 | glutathione-S transferase | glutathione-S transferase (*Pseudomonas stutzeri*) | 7 | 8 | 69 | 1.3E − 86 | Hofer et al., Gene 144 (1), 9–16 (1994) |
| ORF7 | hydratase | 2-oxopent-4-enoate hydratase (*Pseudomonas stutzeri*) | 9 | 10 | 34 | 2.0E − 27 | Bosch et al., unpublished GI4104769 |
| ORF23 | traI | TraI (*Salmonella typhimurium*) | 11 | 12 | 53 | 0.0E + 0.0 | Winans, S.C., Submitted GI1163228 |

TABLE 4-continued

| ORF Name | Gene Name | Similarity Identified | SEQ ID base | SEQ ID Peptide | % Identity[a] | E-value[b] | Citation |
|---|---|---|---|---|---|---|---|
| ORF24 | traJ | AF109305_2 mobilization protein TraJ (Salmonella typhimurium | 13 | 14 | 46 | E − 127 | Paterson et al., J Bacteriol 181:2572–2583, 1999 |
| ORF25 | traK | traK (*Salmonella typhimurium* | 15 | 16 | 36 | 3.0E − 0.3 | Woodgate, R. Unpublished GI2145308 |
| ORF33 | vagD | vagD-*Salmonella dublin* virulence plasmid | 17 | 18 | 73 | 3.0E − 26 | Pullinger and Lax Mol Microbiol 6:1631–1543 (1992) |
| ORF34 | vagC | vagC-*Salmonella dublin* virulence plasmid | 19 | 20 | 61 | 8.0E − 22 | Pullinger and Lax Mol Microbiol 6:1631–1543 (1992) |
| ORF38 | rep | Replication initiator and trascription repressor | 21 | 22 | 34 | 8.0E − 34 | Fu et al., Plasmid 34:75–84 (1995) |

[a] % Identity is defined as percentage of amino acids that are identical between the two proteins.
[b] Expect value. The Expect value estimates the statistical significance of the match, specifying the number of matches, with a given score, that are expected in a search of a database of this size absolutely by chance

TABLE 5

Comparison of pCT14 Lower Pathway Against GenBank Database

|  | tbuW ORF1 | tdnC ORF2 | dmpC ORF4 | bhpX0 ORF5 | dmpE ORF7 |
|---|---|---|---|---|---|
| DNA | 80% | 74% | 68% | 64% | 54% |
| Amino Acid | 62% | 70% | 63% | 69% | 34% |

---

What is claimed is:

1. An isolated bacterial plasmid having the nucleotide sequence as set forth in SEQ ID NO:23.

2. An isolated bacterial strain comprising the plasmid of claim 1.

3. A method for the degradation of aromatic compounds comprising contacting the strain of claim 2 with an aromatic compound under suitable growth conditions wherein the aromatic compound is degraded.

4. A method according to claim 3 wherein the aromatic compound is selected from the group consisting of catechol, methylcatechol, 4-methylcatechol, 3-chlorocatechol, 4-chlorocatechol, protocatechuate, 2-hydroxymuconic-semialdehyde, methyl-2-hydroxymuconic-semialdehyde, chloro-2-hydroxymuconic-semialdehyde and 2-hydroxypent-2,4-dienoate.

* * * * *